US010858704B2

(12) United States Patent
Lambert et al.

(10) Patent No.: US 10,858,704 B2
(45) Date of Patent: Dec. 8, 2020

(54) METHODS FOR MEASURING VIRULENCE IN SOYBEAN CYST NEMATODE

(71) Applicant: THE BOARD OF TRUSTEES OF THE UNIVERSITY OF ILLINOIS, Urbana, IL (US)

(72) Inventors: Kris Lambert, Urbana, IL (US); Sadia Bekal, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 939 days.

(21) Appl. No.: 14/939,854

(22) Filed: Nov. 12, 2015

(65) Prior Publication Data
US 2016/0177392 A1 Jun. 23, 2016

Related U.S. Application Data

(60) Provisional application No. 62/078,570, filed on Nov. 12, 2014, provisional application No. 62/094,367, filed on Dec. 19, 2014, provisional application No. 62/239,046, filed on Oct. 8, 2015.

(51) Int. Cl.
*C12P 19/34* (2006.01)
*C12Q 1/6883* (2018.01)

(52) U.S. Cl.
CPC ..... *C12Q 1/6883* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS

2007/0250947 A1* 10/2007 Boukharov ........... A23L 33/105 800/278
2007/0271630 A1* 11/2007 Boukharov ........ C12N 15/8241 800/279

OTHER PUBLICATIONS

Cook et al. Distinct copy number, coding sequence, and locus methylation patterns underlie Rhg1-mediated soybean resistance to soyabean nematode. Plant Physiol., vol. 165, p. 630-647, 2014.*
Craig et al. Evidence for horizontally transferred genes involved in the biosynthesis of vitamin B, B5 and B7 in Heterodera Glycines. J. Nematology, vol. 41(4), p. 281-290, 2009.*
Li et al. Quantitative field testing Heterodera Glycines from metagenomic DNA samples isolated directly from soil under agronomic production. PLOS One, vol. 9(2), e89887, p. 1-8,2014.*
Wang et al. Dual roles for the variable doman in protein trafficking and host-specific recognition of heterodera glycines CLE effector proteins. New Phytologist, vol. 187, p. 1003-1017, 2010.*
Atibalentja et al., "A genetic linkage map of the soybean cyst nematode *Heterodera glycines.*" *Mol Genet Genomics* 273: 273-281, 2005.
Bekal et al., "A SNARE-Like Protein and Biotin Are Implicated in Soybean Cyst Nematode Virulence." *PLoS One* 10:e0145601 2015; 25 pages (doi: 10.1371/journal.pone.0145601).
Cook et al., "Copy number variation of multiple genes at Rhg1 mediates nematode resistance in soybean." *Science* 338: 1206-1209, 2012.
Craig et al., "Analysis of a horizontally transferred pathway involved in vitamin B6 biosynthesis from the soybean cyst nematode *Heterodera glycines.*" *Mol Biol Evol* 25: 2085-2098, 2008.
Craig et al., "Evidence for horizontally transferred genes involved in the biosynthesis of vitamin B(1), B(5), and B(7) in *Heterodera glycines.*" *J Nematol* 41: 281-290, 2009.
Dong & Opperman, "Genetic analysis of parasitism in the soybean cyst nematode *Heterodera glycines.*" *Genetics* 146: 1311-1318, 1997.
Feng et al., "A Francisella virulence factor catalyses an essential reaction of biotin synthesis." *Molecular Microbiology* 91: 300-314, 2014.
Matsye et al., "The expression of a naturally occurring, truncated allele of an α-SNAP gene suppresses plant parasitic nematode infection." *Plant Mol Biol* 80: 131-155, 2012.
Niblack et al., "Distribution, Density, and Diversity of *Heterodera glycines* in Missouri," *Supplement to Journal of Nematology* 25(45):880-886, 1993.
Niblack et al., "A Revised Classification Scheme for Genetically Diverse Populations of *Heterodera glycines,*" *Journal of Nematology* 34(4):279-288, 2002.

(Continued)

*Primary Examiner* — Kenneth R Horlick
(74) *Attorney, Agent, or Firm* — Klarquist Sparkman, LLP

(57) ABSTRACT

Phytoparasitic nematodes that are able to infect and reproduce on plants that are considered resistant are referred to as virulent. The mechanism(s) that virulent nematodes employ to evade or suppress host plant defenses are not well understood. Described herein is the discovery of three single nucleotide polymorphisms (SNPs) that reproducibly show allele imbalances between soybean cyst nematode (SCN) grown on resistant and susceptible soybean (*Heterodera glycines*) plants. Two candidate SCN virulence genes, biotin synthase (HgBioB) and a bacterial-like protein containing a putative SNARE domain (HgSLP-1), were tightly linked to the SNPs. Methods, kits, and compositions are provided for using these discoveries to detect and quantify SCN virulence in field samples. Also provided are methods for planting fields in accordance with the results of detecting (or not detecting) virulent SCN in the fields.

9 Claims, 9 Drawing Sheets
(2 of 9 Drawing Sheet(s) Filed in Color)
Specification includes a Sequence Listing.

(56) References Cited

OTHER PUBLICATIONS

Smant et al., "Endogenous cellulases in animals: isolation of beta-1,4-endoglucanase genes from two species of plant-parasitic cyst nematodes." *Proc Natl Acad Sci U S A* 95: 4906-4911, 1998.
Zempleni et al., "Biotin." *BioFactors* 35: 36-46, 2009.
Zempleni et al., "Repression of transposable elements by histone biotinylation." *The Journal of Nutrition* 139: 2389-2392, 2009.
"Exonuclease I—Shrimp Alkaline Phosphatase Clean Up of PCR Products," www.nucleics.com/DNA_sequencing_support/exonucleaseI-SAP-PCR-protocol.html, 5 pages, downloaded Oct. 31, 2015.

\* cited by examiner

FIG. 9D vesicle membrane target membrane

● v-SNARE ● t-SNARE ● HgSLP-1 ● alternate form of HgSLP-1 ● soybean alpha SNAP

SEQUENCE LISTING

```
<160> NUMBER OF SEQ ID NOS: 51

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 1
gcggcagatt gaagaagcat tt                                          22

<210> SEQ ID NO 2
<211> LENGTH: 19
<212> TYPE: DNA
```

```
<213> ORGANISM: Artificial sequence
<220> FEATURE:
<223> OTHER INFORMATION: Synthetic oligonucleotide

<400> SEQUENCE: 2
gcacggcact gatcagaca                                                   19

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: variation
<222> LOCATION: (10)..(10)
<223> OTHER INFORMATION: SNP location

<400> SEQUENCE: 3
cctctccatg cggacc                                                      16

<210> SEQ ID NO 4
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: variation
<222> LOCATION: (12)..(12)
<223> OTHER INFORMATION: SNP location

<400> SEQUENCE: 4
agcctctcca tacggacc                                                    18

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
gccattggag cgccagatgc                                                  20

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
ggctcatcgg cggcacaa                                                    18

<210> SEQ ID NO 7
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 7
ucuaauagug auaacagccu gcuacuu                                          27

<210> SEQ ID NO 8
<211> LENGTH: 25
```

```
<212> TYPE: RNA
<213> ORGANISM: Artificial sequence
<220> FEATURE:
<223> OTHER INFORMATION: Synthetic oligonucleotide

<400> SEQUENCE: 8
agauuaucac uauugucgga cgaug                                              25

<210> SEQ ID NO 9
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 9
agacaauaug agaacaucgu gccacau                                            27

<210> SEQ ID NO 10
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 10
ucuguuauac ucuuguagca cggug                                              25

<210> SEQ ID NO 11
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 11
guucauuuca ucucgaagcu cgucgau                                            27

<210> SEQ ID NO 12
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 12
caaguaaagu agagcuucga gcagc                                              25

<210> SEQ ID NO 13
<211> LENGTH: 27
<212> TYPE: RNA
<213> ORGANISM: Artificial sequence
<220> FEATURE:
<223> OTHER INFORMATION: Synthetic oligonucleotide

<400> SEQUENCE: 13
uggucgaguc guuggucugu ucggucc                                            27

<210> SEQ ID NO 14
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 14
```
accagcucag caaccagaca agcca                                              25

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
aggtgaccaa attctacc                                                      18

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
gggtgtccat ttatttgc                                                      18

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
ctgaccgagg atggacaa                                                      18

<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
cgagatgaaa tgaaccaaa                                                     19

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
gagtcgtttg tccatttg                                                      18

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
aacacgagat tggac                                                         15

<210> SEQ ID NO 21
<211> LENGTH: 15
<212> TYPE: PRT
<213> ORGANISM: Artificial sequence

```
<220> FEATURE:
<223> OTHER INFORMATION: Synthetic peptide

<400> SEQUENCE: 21

Cys Arg His Leu Phe Glu Ser Gly Glu Ala Ser Glu Thr Ala Ser
1               5                   10                  15

<210> SEQ ID NO 22
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 22
aaacccggga atggccgatc agttatcgaa gg                              32

<210> SEQ ID NO 23
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 23
aaaactcgag tcaagtaata acctcatact cc                              32

<210> SEQ ID NO 24
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 24
ggtcttgagc ggatatctta accgg                                      25

<210> SEQ ID NO 25
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 25
ctcgacatct cagatctatg gcacc                                      25

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gaaaaagcag caccgaatgc                                            20

<210> SEQ ID NO 27
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 27
cggtgctgct ttttccatag atctgccata tgtatatctc ct                   42
```

<210> SEQ ID NO 28
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 28
tcgcgaatgc gaattcatgg ccgat         25

<210> SEQ ID NO 29
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 29
cgtcgagcat gtcgactcaa tggtg         25

<210> SEQ ID NO 30
<211> LENGTH: 71
<212> TYPE: PRT
<213> ORGANISM: Rattus norvegicus

<400> SEQUENCE: 30

Gly Ser Met Arg Glu Thr Ala Ile Gln Gln Leu Glu Ala Asp Ile Leu
1               5                   10                  15

Asp Val Asn Gln Ile Phe Lys Asp Leu Ala Met Met Ile His Asp Gln
            20                  25                  30

Gly Asp Leu Ile Asp Ser Ile Glu Ala Asn Val Glu Ser Ser Glu Val
        35                  40                  45

His Val Glu Arg Ala Ser Asp Gln Leu Gln Arg Ala Ala Tyr Tyr Gln
    50                  55                  60

Lys Lys Ser Arg Lys Lys Met
65                  70

<210> SEQ ID NO 31
<211> LENGTH: 326
<212> TYPE: PRT
<213> ORGANISM: Heterodera glycines

<400> SEQUENCE: 31

Met Ala Pro Lys Cys Leu Pro Leu Glu Leu Leu Phe Glu Ile Val Pro
1               5                   10                  15

Phe Ile Pro Ala Glu Lys Ala Ala Pro Asn Ala Leu Ser Ser Cys Leu
            20                  25                  30

Leu Leu His Asn Leu Leu Leu Pro Arg Val Ile Lys Trp Lys Glu Leu
        35                  40                  45

Lys Lys Met Ile Lys Glu Leu Arg Asp Glu Val Phe Gly Lys Ile Asp
    50                  55                  60

Glu Leu Arg Asp Glu Met Asn Gln Lys Phe Gly Gln Ile Asn Thr Arg
65                  70                  75                  80

Leu Asp Arg Thr Asp Gln Arg Leu Asp Gln Met Asp Lys Arg Leu Asp
            85                  90                  95

Arg Met Asp Gln Arg Leu Asp Gln Phe Glu Gln Tyr Gly Pro Val Pro
        100                 105                 110

Pro Pro Met Pro Leu Gln Ser Gly His Tyr Ser Gly Ile Glu Ser Thr
    115                 120                 125

-continued

```
Ser Glu Phe Ser Glu Leu Arg Gln Ile Gly Thr Ser Ala Ala Phe Asp
            130                 135                 140

Thr Arg Gln Asn Thr Gly Ser Glu Leu Gln Arg Pro Pro Phe Leu
145                 150                 155                 160

His His Val Ser Glu Thr Gly Asn Pro Val Pro Ile Leu Ser Ser Ile
                165                 170                 175

Gly Leu Asn Ala Leu Phe Thr Pro Leu Ser His Phe Tyr Phe Gly Asn
                180                 185                 190

Cys Val Pro Ser Met Thr Ser Pro Ile Cys Pro Lys Asp Lys Pro Asn
            195                 200                 205

Val Glu Phe Asp Val Asp Leu Gly His Asp Leu Ser Thr Gln Asn Val
            210                 215                 220

Gly Asp Leu Leu Lys Gly Gln Arg Ser Val Leu Ala Asp Pro Pro Met
225                 230                 235                 240

Gln Leu Phe Pro Arg His Leu Phe Glu Ser Gly Glu Ala Ser Glu Thr
                245                 250                 255

Ala Ser Asp Arg Lys Glu Ser Met Gly Lys Gly Arg Lys Lys Pro Ser
            260                 265                 270

Lys Glu Val Ala Asp Ala Gly Leu Thr Pro Ser Asp Glu Leu Asn Lys
            275                 280                 285

Thr Ala Ser Ile Val Pro Thr Ser Val Gln Thr Phe Arg Arg His Leu
290                 295                 300

Ser Glu Thr Gly Asn Arg Met Arg Asn Leu Phe Arg Thr Asn Thr Leu
305                 310                 315                 320

Ser Tyr Ser Phe Lys Lys
                325
```

<210> SEQ ID NO 32
<211> LENGTH: 416
<212> TYPE: PRT
<213> ORGANISM: Arabidopsis thaliana

<400> SEQUENCE: 32

```
Met Val Arg Ser Asn Asp Val Lys Phe Gln Val Tyr Asp Ala Glu Leu
1               5                   10                  15

Thr His Phe Asp Leu Glu Ser Asn Asn Asn Leu Gln Tyr Ser Leu Ser
                20                  25                  30

Leu Asn Leu Ser Ile Arg Asn Ser Lys Ser Ser Ile Gly Ile His Tyr
            35                  40                  45

Asp Arg Phe Glu Ala Thr Val Tyr Tyr Met Asn Gln Arg Leu Gly Ala
        50                  55                  60

Val Pro Met Pro Leu Phe Tyr Leu Gly Ser Lys Asn Thr Met Leu Leu
65                  70                  75                  80

Arg Ala Leu Phe Glu Gly Gln Thr Leu Val Leu Leu Lys Gly Asn Glu
                85                  90                  95

Arg Lys Lys Phe Glu Asp Asp Gln Lys Thr Gly Val Tyr Arg Ile Asp
            100                 105                 110

Val Lys Leu Ser Ile Asn Phe Arg Val Met Val Leu His Leu Val Thr
        115                 120                 125

Trp Pro Met Lys Pro Val Val Arg Cys His Leu Lys Ile Pro Leu Ala
    130                 135                 140

Leu Gly Ser Ser Asn Ser Thr Gly Gly His Lys Lys Met Leu Leu Ile
145                 150                 155                 160

Gly Gln Leu Val Lys Asp Thr Ser Ala Asn Leu Arg Glu Ala Ser Glu
```

```
                165                 170                 175
Thr Asp His Arg Arg Asp Val Ala Gln Ser Lys Lys Ile Ala Asp Ala
            180                 185                 190

Lys Leu Ala Lys Asp Phe Glu Ala Ala Leu Lys Glu Phe Gln Lys Ala
        195                 200                 205

Gln His Ile Thr Val Glu Arg Glu Thr Ser Tyr Ile Pro Phe Asp Pro
    210                 215                 220

Lys Gly Ser Phe Ser Ser Glu Val Asp Ile Gly Tyr Asp Arg Ser
225                 230                 235                 240

Gln Glu Gln Arg Val Leu Met Glu Ser Arg Gln Glu Ile Val Leu
            245                 250                 255

Leu Asp Asn Glu Ile Ser Leu Asn Glu Ala Arg Ile Glu Ala Arg Glu
        260                 265                 270

Gln Gly Ile Gln Glu Val Lys His Gln Ile Ser Glu Val Met Glu Met
    275                 280                 285

Phe Lys Asp Leu Ala Val Met Val Asp His Gln Gly Thr Ile Asp Asp
290                 295                 300

Ile Asp Glu Lys Ile Asp Asn Leu Arg Ser Ala Ala Ala Gln Gly Lys
305                 310                 315                 320

Ser His Leu Val Lys Ala Ser Asn Thr Gln Gly Ser Asn Ser Ser Leu
            325                 330                 335

Leu Phe Ser Cys Ser Leu Leu Leu Phe Phe Phe Leu Ser Gly Asp Leu
        340                 345                 350

Cys Arg Cys Val Cys Val Gly Ser Glu Asn Pro Arg Leu Asn Pro Thr
    355                 360                 365

Arg Arg Lys Ala Trp Cys Glu Glu Glu Asp Glu Glu Gln Arg Lys Lys
        370                 375                 380

Gln Gln Lys Lys Lys Thr Met Ser Glu Lys Arg Arg Glu Glu Lys
385                 390                 395                 400

Lys Val Asn Lys Pro Asn Gly Phe Val Phe Cys Val Leu Gly His Lys
                405                 410                 415

<210> SEQ ID NO 33
<211> LENGTH: 311
<212> TYPE: PRT
<213> ORGANISM: Capsicum annuum

<400> SEQUENCE: 33

Met Asn Asp Leu Met Thr Lys Ser Phe Thr Ser Tyr Val Asp Leu Lys
1               5                   10                  15

Lys Ala Ala Met Lys Asp Ala Glu Ser Gly Pro Asp Leu Glu Met Gly
            20                  25                  30

Met Thr Gln Met Asp Gln Asn Leu Thr Ala Phe Leu Glu Glu Ala Glu
        35                  40                  45

Lys Val Lys Val Glu Met Asn Ser Ile Lys Asp Ile Leu Arg Arg Leu
    50                  55                  60

Gln Asp Thr Asn Glu Glu Ser Lys Ser Leu Thr Lys Pro Glu Ala Leu
65                  70                  75                  80

Lys Ser Met Arg Asn Leu Ile Asn Ser Asp Ile Leu Ala Val Leu Thr
                85                  90                  95

Lys Ala Arg Ala Ile Arg Ser Gln Leu Glu Glu Met Asp Arg Ser Asn
            100                 105                 110

Ala Ile Asn Arg Arg Leu Ser Gly Cys Lys Glu Gly Thr Pro Val Asp
        115                 120                 125
```

```
Arg Thr Arg Phe Ala Val Thr Asn Gly Leu Arg Lys Lys Leu Lys Glu
            130                 135                 140

Leu Met Met Asp Phe Gln Gly Leu Arg Gln Arg Met Met Ser Glu Tyr
145                 150                 155                 160

Lys Glu Thr Val Gly Arg Arg Tyr Phe Thr Val Thr Gly Glu Gln Pro
                165                 170                 175

Asp Glu Glu Val Ile Asp Lys Ile Ile Ser Gly Asn Gly Gln Gly
            180                 185                 190

Gly Glu Glu Phe Leu Ser Arg Ala Ile Gln Glu His Gly Arg Gly Lys
                195                 200                 205

Val Leu Glu Thr Val Val Glu Ile Gln Asp Arg His Asp Ala Ala Lys
210                 215                 220

Glu Ile Glu Lys Ser Leu Leu Glu Leu His Gln Ile Phe Leu Asp Met
225                 230                 235                 240

Ala Val Met Val Glu Ala Gln Gly Glu Lys Met Asp Asp Ile Glu His
                245                 250                 255

His Val Val Asn Ala Ala Gln Tyr Val Asn Asp Gly Thr Lys Asn Leu
            260                 265                 270

Lys Thr Ala Lys Glu Tyr Gln Lys Ser Ser Arg Thr Trp Met Cys Ile
                275                 280                 285

Gly Ile Ile Ile Leu Leu Ile Leu Ile Leu Val Val Ile Ile Pro Ile
290                 295                 300

Ala Thr Ser Phe Thr Lys Ser
305                 310

<210> SEQ ID NO 34
<211> LENGTH: 346
<212> TYPE: PRT
<213> ORGANISM: Pyropia yezoensis

<400> SEQUENCE: 34

Met Val Lys Asp His Phe Ala Glu Leu Thr Ala Gly Leu Ala Pro Glu
1               5                   10                  15

Pro Asp Val Glu Val Gly Asp Gly Gly Ala Ala Ala Gly Ala
            20                  25                  30

Gly Pro Gly Phe Glu Lys Phe Arg Arg Glu Ile Asp Ala Met Asp Lys
                35                  40                  45

Ala Val Val Trp Val Ala Thr Gln Thr Ser Ala Val Asn Asn Gly Glu
50                  55                  60

Val Pro Pro Pro Ser Ile Pro Val Leu Leu Asn Thr Cys Lys Asp Lys
65                  70                  75                  80

Leu Ser Ala Val Arg Arg Arg Leu Asp Arg Val Ala Lys Glu Asn Arg
                85                  90                  95

Ala Phe Ala Ala Ala Asn Pro Asn Ser Thr Gly Glu Ser Lys Leu Arg
            100                 105                 110

Val Asn Thr His Thr Gly Leu Val Gln Arg Phe Ile Thr Ala Ala Gly
            115                 120                 125

Ser Leu Gln Ser Thr Ser Ala Ala His Ala Ser Thr Ala Ser Thr Ser
130                 135                 140

Val Ala Ser Ser Met Arg Ala Leu Ala Pro Gly Ala Ala Glu Ala Asp
145                 150                 155                 160

Val Gln Ala Ala Leu Gly Ser Gly Arg Gly Asp Ala Ala Val Asp
                165                 170                 175

Arg Leu Val Ser Thr Ala Asp Ala Ala Arg Arg Val Glu Leu Arg Gly
            180                 185                 190
```

Gln Ile Glu Asp Leu Arg Ala Arg Asn Ala Asp Ile Gly Lys Leu Ala
            195                 200                 205

Gly Ser Leu Thr Glu Leu His Ala Met Phe Val Asp Met Gly Leu Leu
        210                 215                 220

Val Asn Gln Gln Thr Glu Leu Leu Asn Asn Ile Glu Ala Asn Val Glu
225                 230                 235                 240

Lys Thr Lys Val Glu Thr Val Lys Ala Asn Glu Glu Leu Val Ser Ala
                245                 250                 255

Arg Ala Tyr Gln Lys Lys Arg Lys Lys Ile Cys Cys Val Val Ile
            260                 265                 270

Leu Val Ile Ala Ile Ile Ala Ala Ile Leu Ile Pro Val Leu Ile Thr
        275                 280                 285

Gln Leu Pro Lys Trp Thr Ala Ser Val Ser Glu Ala Ala Ser Ser Val
        290                 295                 300

Ser Asp Ala Phe Thr Gly Gly Ser Ser Thr Pro Ser Cys His Arg
305                 310                 315                 320

Arg Gln Pro Arg Arg Leu Cys Val Trp Arg Gly Lys Glu Ser Thr Ala
                325                 330                 335

Gly Thr Gly Gly Ser Arg Pro Arg Ser Asp
            340                 345

<210> SEQ ID NO 35
<211> LENGTH: 267
<212> TYPE: PRT
<213> ORGANISM: Arabidopsis thaliana

<400> SEQUENCE: 35

Met Pro Val Ile Asp Ile Ile Phe Arg Val Asp Glu Ile Cys Lys Lys
1               5                   10                  15

Tyr Asp Lys Tyr Asp Ile Asp Lys His Arg Glu Ile Gly Ala Ser Gly
            20                  25                  30

Asp Asp Ala Phe Ser Arg Leu Phe Thr Ser Ile Asp Ser Asp Ile Glu
        35                  40                  45

Ala Val Leu Arg Lys Ala Glu Leu Ala Ser Thr Glu Lys Asn Arg Ala
50                  55                  60

Ala Ala Val Ala Met Asn Ala Glu Val Arg Arg Thr Lys Ala Arg Leu
65                  70                  75                  80

Ala Glu Asp Val Val Lys Leu Gln Lys Leu Ala Val Lys Lys Ile Lys
                85                  90                  95

Gly Leu Thr Arg Glu Glu Arg Glu Ser Arg Cys Asp Leu Val Ile Ala
            100                 105                 110

Leu Ala Asp Arg Leu Gln Ala Ile Pro Asp Gly Asn Glu His Gly Ala
        115                 120                 125

Lys Gln Ala Asn Ser Asp Trp Gly Gly Ala Ser Ala Pro Asn Lys Asn
130                 135                 140

Ile Lys Phe Asp Met Ser Glu Glu Asp Met Asp Gly Phe Phe Gln
145                 150                 155                 160

Gln Ser Glu Glu Ser Ser Gln Phe Arg Gln Glu Tyr Glu Met Arg Arg
                165                 170                 175

Lys Lys Gln Asp Glu Gly Leu Asp Ile Ile Ser Glu Gly Leu Asp Ala
            180                 185                 190

Leu Lys Asn Leu Ala Arg Asp Met Asn Glu Glu Leu Asp Lys Gln Val
        195                 200                 205

Pro Leu Met Glu Glu Met Glu Thr Lys Val Asp Gly Ala Thr Ser Asp

```
                210                 215                 220
Leu Lys Asn Thr Asn Val Arg Leu Lys Lys Gln Leu Val Gln Met Arg
225                 230                 235                 240

Ser Ser Arg Asn Phe Cys Ile Asp Ile Ile Leu Leu Cys Val Ile Leu
                245                 250                 255

Gly Ile Val Ser Tyr Ile Tyr Asn Ala Leu Asn
            260                 265

<210> SEQ ID NO 36
<211> LENGTH: 111
<212> TYPE: PRT
<213> ORGANISM: Rattus norvegicus

<400> SEQUENCE: 36

Met Ala Asp Trp Thr Arg Ala Gln Ser Ser Gly Ala Val Glu Glu Ile
1               5                   10                  15

Val Asp Arg Glu Asn Lys Arg Met Ala Asp Ser Leu Ala Ser Lys Val
            20                  25                  30

Thr Arg Leu Lys Ser Leu Ala Leu Asp Ile Asp Arg Asp Thr Glu Asp
        35                  40                  45

Gln Asn Arg Tyr Leu Asp Gly Met Asp Ser Asp Phe Thr Ser Val Thr
    50                  55                  60

Gly Leu Leu Thr Gly Ser Val Lys Arg Phe Ser Thr Val Ala Arg Ser
65                  70                  75                  80

Gly Arg Asp Thr Arg Lys Leu Leu Cys Gly Met Ala Val Val Leu Ile
                85                  90                  95

Val Ala Phe Phe Ile Leu Ser Tyr Leu Phe Ser Arg Thr Arg Thr
            100                 105                 110

<210> SEQ ID NO 37
<211> LENGTH: 263
<212> TYPE: PRT
<213> ORGANISM: Arabidopsis thaliana

<400> SEQUENCE: 37

Met Phe Gly Phe Phe Lys Ser Pro Gly Asn Asn Lys Leu Pro Asn Glu
1               5                   10                  15

Ser Ser Asn Asn Lys Gly Gly Thr Ile Thr Ala Gly Arg Arg Thr Ser
            20                  25                  30

Ser Glu Pro Ile Leu Ile Thr Pro Asp Phe Asp Asp Asp Lys Tyr
        35                  40                  45

Lys Asn Gly Phe Asn Asp Ser Gly Gly Leu Gln Ser Gln Thr Thr Glu
    50                  55                  60

Glu Leu Glu Lys Tyr Ala Val Tyr Lys Ala Glu Glu Thr Thr Lys Gly
65                  70                  75                  80

Val Asn Asn Cys Leu Lys Ile Ala Glu Asp Ile Arg Ser Asp Gly Ala
                85                  90                  95

Arg Thr Leu Glu Met Leu His Gln Gln Gly Glu Gln Ile Asn Arg Thr
            100                 105                 110

His Glu Met Ala Val Asp Met Asp Lys Asp Leu Ser Arg Gly Glu Lys
        115                 120                 125

Leu Leu Asn Asn Leu Gly Gly Met Phe Ser Lys Pro Trp Lys Pro Lys
    130                 135                 140

Lys Thr Lys Asn Ile Thr Gly Pro Met Ile Thr Pro Asp Lys Pro Ser
145                 150                 155                 160

Lys Lys Ser Glu Asn His Lys Glu Glu Arg Glu Lys Leu Gly Leu Gly
```

```
            165                 170                 175
Ala Lys Gly Arg Ser Ser Gln Pro Ala Leu Asp Gln Pro Thr Asn
        180                 185                 190

Ala Leu Gln Lys Val Glu Gln Glu Lys Ala Lys Gln Asp Asp Gly Leu
    195                 200                 205

Ser Asp Leu Ser Asp Ile Leu Gly Asp Leu Lys Ser Met Ala Val Asp
210                 215                 220

Met Gly Ser Glu Ile Asp Lys Gln Asn Lys Ala Leu Asp His Leu Gly
225                 230                 235                 240

Asp Asp Val Asp Glu Leu Asn Ser Arg Val Gln Gly Ala Asn Gln Arg
                245                 250                 255

Ala Arg His Leu Leu Ser Lys
            260

<210> SEQ ID NO 38
<211> LENGTH: 212
<212> TYPE: PRT
<213> ORGANISM: Strongylocentrotus purpuratus

<400> SEQUENCE: 38

Met Glu Asp Gln Asn Asp Met Asn Met Arg Ser Glu Leu Glu Glu Ile
1               5                   10                  15

Gln Met Gln Ser Asn Met Gln Thr Asp Glu Ser Leu Glu Ser Thr Arg
            20                  25                  30

Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
    50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210

<210> SEQ ID NO 39
<211> LENGTH: 212
<212> TYPE: PRT
<213> ORGANISM: Hirudo medicinalis

<400> SEQUENCE: 39

Met Ala Lys Asp Ile Lys Pro Lys Pro Ala Asn Gly Arg Asp Ser Pro
```

```
1               5                   10                  15
Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80
Asp Ala Glu Lys Asn Leu Glu Gly Met Glu Lys Cys Cys Gly Leu Cys
                85                  90                  95
Ile Leu Pro Trp Lys Arg Thr Lys Asn Phe Asp Lys Gly Ala Glu Trp
            100                 105                 110

Asn Lys Gly Asp Glu Gly Lys Val Asn Thr Asp Gly Pro Arg Leu Val
        115                 120                 125

Val Gly Asp Gly Asn Met Gly Pro Ser Gly Gly Phe Ile Thr Lys Ile
    130                 135                 140

Thr Asn Asp Ala Arg Glu Glu Glu Met Glu Gln Asn Met Gly Glu Val
145                 150                 155                 160
Ser Asn Met Ile Ser Asn Leu Arg Asn Met Ala Val Asp Met Gly Ser
                165                 170                 175
Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210
```

<210> SEQ ID NO 40
<211> LENGTH: 3633
<212> TYPE: DNA
<213> ORGANISM: Heterodera glycines

<400> SEQUENCE: 40

```
atggccccca aatgccttcc gctcgaactg ttgttcgaaa ttgtgccttt catccctgcc     60
gaaaaggccg ccccaaatgc gctctcgtca tgtctgctgc tgcacaacct tttgctgcca    120
cgtgtcatca aatggaaaga ggtaggccct gccatatttg ggacaccaag gaatgggctc    180
aaaattcaat tgttcacttc cggtcaccca cttgaaaaca cacaggaatg tggcacgatg    240
ttctcatatt gtctctcttt aaaagaaatt tcatttaaat tgcttaactt ccttaaatct    300
tttttctatt tccatcaagt agcaggctgt tatcactatt agagcccgga cacaaaaagg    360
caacaaaatt gtaaattttt agtttaaatc ttaaagatat tgggccaaaa attttccatg    420
tatccatagg cgactatcgg caccgccggc gctcccaaat tcgcgttaat tttttaaatt    480
tattatgaat tgacaaaaat tttttgattt caaatatatc gagcttcgaa atttcgggtt    540
tttgggtttg aacttgcgtt agccatcagt ttcgagtgct aagccgagct tcgcccgtcc    600
ctgtctcaga ccagcaggag gccccatttc ttatgctgga ctagaactga ttttttttaaa    660 aactcccagg aaccagacgc taacattcga tagcgcaaag ttttttctat tagcctgcaa    720
aatcagggct aatagagcat ttgaagggct taagaatgat accaagatta ttagaattgg    780
ttaacaaaga aaaaagttgt aatcaaaaat ttgggctggc accgaaacgc caaaacggcc    840
aatccctttt tttagattta aatgtttggc cttctatttc ctaataataa tttcttattt    900
```

```
tttacttttta ttgtaatcgt tttcaagaaa ttgcttgaat ttagataatt tgattcacat      960
gaaaaattta gattattctt ttatttattt aagttgaaaa aaatgataaa agagcttcga     1020
gatgaagtgt tcggaaagat cgacgagctt cgagatgaaa tgaaccaaaa atttggccaa     1080
atcaacacga gattggaccg aacagaccaa cgactcgacc aaatggacaa acgactcgac     1140
cgaatggacc aacgactcga ccaatttgag gtaattttga cagatctaag cttagttgtc     1200
ggtagttctg cttttgggct tacatttatt gttgctgggt ttgtttatgg acccattgta     1260
ctttatttct caatgtttgg acagaccata catttaatct cattgaaacc caattcgggg     1320
caggcgcttt tggttagcgg cgttcgttcc ccaaaaaatg accaggattc agtatcgcgt     1380
ttgaataatt tccctcccct ccactgatca gcagtatggc cctgtgccgc caccgatgcc     1440
gcttcagtcc ggccactaca gtggtattga ggtatattcc caaattttaa ttttcgggag     1500
gaaacgacgc agaccgcagg ttgggaaaac gaactgctcc gcttgttttt tggcgttttg     1560
tcggggccaa aatttgaaaa tgcaattcct tgaattacaa atacacaatt cacagtctac     1620
ctccgagttt tccgagttgc gccagattgg gacttctgcc gcatttgaca cccgccaaaa     1680
caccggcagc gaattgcaac gccgccctcc atttcttcac cacgtgtccg agaccggcaa     1740
ccctgtgcca atattggtgc ggagcttaac taaaaacctt tcctattgat aaattttttca    1800
aaaattttca gactaggctg attaactata aattttgtg atatcagact ttcagagttc      1860
gatcgggctc aacgctctgt tcactcctct ttcccatttt tattttggca actgtgttcc     1920
gtcaatgacg tcgccgatct gcccaaagga caaagtatat atttggtcgc tggtttaatt     1980
cactacggct taggcttaat tgggccgccc cccactctcc gtaccccata ttcagttttt     2040
caaaaaaaaa aaaatcaaa atggcgtcta ttttacaaaa tttgtagccg ataaattact      2100
gttttttgcca tttggtcact atttttcaaa aatgataaaa tgtgggtatc gcagctttac    2160
gttgtacagg tcaggcagtg ccgtcaggca ccgtcgggaa aattaaataa agcaatttgt     2220
taagaagaat tgcttaaaat ttaaaatgaa attttttagtt tttttgggct tagggggggg    2280
gctttagccc ctcaatccct cctgtgaatc ttttcaagga ttaggcagcc atttgctttt     2340
ggtcatcccc agtagttttt tgcataagat atttttttcac gttttctctt tgaaatattt    2400
ttagttttcg ggaggaaata aaacggcggt gaatatcatg ggccggtttt ttgacatttt     2460
ctgtaccaaa atttgaaact gcacttcctt gaatacaaat gtacaattca cagcccaacg    2520
tcgagttcga cgtggacctc ggccacgact tgagcaccca aaatgtgggc gatcttttga    2580
aagggcaacg cagcgttttg gccgatccgc cgatgcaatt gtttcctcgc catttgttcg    2640
aggtttgcaa cagagcgcca aaattggtgt ggagcttaac tatagtaaga acccatccca    2700
gggataattt ttttcaaaa acttgaaatt aaaaaaaaag ttttttgaaaa agatgaaatg    2760
ttactgacac aaactttgtg aatttcggaa aaaacttacg cctgccaatt tttaatgtaa     2820
aattgttgaa gagtggcgaa gcttccgaga cggcgtccga ccgcaaagaa agcatgggaa    2880
aaggacggaa aaaaccgagc aaagaagtcg ctgatgctgg gctcacggtg ataatatttt    2940
ggctgattac gttagtcaat acctagacta gaatttcaac tattttttttt tgaaaatgta    3000
attattcata ttaaaataca aaaaaaattt agaaaaaaat tccattttcc ttgaaaattt    3060
cttttaaatat tttttctaaa atctcaaagt ttgacaaaaa aaagaagtta ttttttgatat   3120
ggaggaggga aacggagagg gggggggggg ggaaacgttg agcacccata aatacaacaa    3180
atgcacaaat cacagccctc cgacgagctg aacaaaaccg cctcaattgt gccaacgtcg    3240
gtgcaaactt ttcgtcgcca cttgtccgag accggcaaca gaatgcgaaa tttggtgcgg    3300
```

```
agcttaacaa agaatccagc ccagggaatt tgaaaatcat aaattttaag gacagcaaaa    3360
attattggga ttcaaaattg gaaacacaat ttgcaaaaat aatgactaaa aaatgttaaa    3420
ttttgacggt ttttaaaggg aaaaaaacta aaatccggaa attttttcaag attattccct   3480 gatgagaaat tccatgggat gtgccaagtt caaattcaga gcaagtggcg aatttggggc    3540
ggagttttta agattttttgg actttctttc catttttccat gatatgtttt tcagttccgt   3600
acgaatacac tcagctattc ctttaagaag tga                                 3633
```

```
<210> SEQ ID NO 41
<211> LENGTH: 981
<212> TYPE: DNA
<213> ORGANISM: Heterodera glycines
<220> FEATURE:
<221> NAME/KEY: CDS
<222> LOCATION: (1)..(981)

<400> SEQUENCE: 41
```

```
atg gcc ccc aaa tgc ctt ccg ctc gaa ctg ttg ttc gaa att gtg cct      48
Met Ala Pro Lys Cys Leu Pro Leu Glu Leu Leu Phe Glu Ile Val Pro
1               5                   10                  15 ttc atc cct gcc gaa aag gcc gcc cca aat gcg ctc tcg tca tgt ctg      96
Phe Ile Pro Ala Glu Lys Ala Ala Pro Asn Ala Leu Ser Ser Cys Leu
                20                  25                  30 ctg ctg cac aac ctt ttg ctg cca cgt gtc atc aaa tgg aaa gag ttg     144
Leu Leu His Asn Leu Leu Leu Pro Arg Val Ile Lys Trp Lys Glu Leu
            35                  40                  45 aaa aaa atg ata aaa gag ctt cga gat gaa gtg ttc gga aag atc gac     192
Lys Lys Met Ile Lys Glu Leu Arg Asp Glu Val Phe Gly Lys Ile Asp
    50                  55                  60 gag ctt cga gat gaa atg aac caa aaa ttt ggc caa atc aac acg aga     240
Glu Leu Arg Asp Glu Met Asn Gln Lys Phe Gly Gln Ile Asn Thr Arg
65                  70                  75                  80 ttg gac cga aca gac caa cga ctc gac caa atg gac aaa cga ctc gac     288
Leu Asp Arg Thr Asp Gln Arg Leu Asp Gln Met Asp Lys Arg Leu Asp
                85                  90                  95 cga atg gac caa cga ctc gac caa ttt gag cag tat ggc cct gtg ccg     336
Arg Met Asp Gln Arg Leu Asp Gln Phe Glu Gln Tyr Gly Pro Val Pro
                100                 105                 110 cca ccg atg ccg ctt cag tcc ggc cac tac agt ggt att gag tct acc     384
Pro Pro Met Pro Leu Gln Ser Gly His Tyr Ser Gly Ile Glu Ser Thr
            115                 120                 125 tcc gag ttt tcc gag ttg cgc cag att ggg act tct gcc gca ttt gac     432
Ser Glu Phe Ser Glu Leu Arg Gln Ile Gly Thr Ser Ala Ala Phe Asp
    130                 135                 140 acc cgc caa aac acc ggc agc gaa ttg caa cgc cgc cct cca ttt ctt     480
Thr Arg Gln Asn Thr Gly Ser Glu Leu Gln Arg Arg Pro Pro Phe Leu
145                 150                 155                 160 cac cac gtg tcc gag acc ggc aac cct gtg cca ata ttg agt tcg atc     528
His His Val Ser Glu Thr Gly Asn Pro Val Pro Ile Leu Ser Ser Ile
                165                 170                 175 ggg ctc aac gct ctg ttc act cct ctt tcc cat ttt tat ttt ggc aac     576
Gly Leu Asn Ala Leu Phe Thr Pro Leu Ser His Phe Tyr Phe Gly Asn
            180                 185                 190 tgt gtt ccg tca atg acg tcg ccg atc tgc cca aag gac aaa ccc aac     624
Cys Val Pro Ser Met Thr Ser Pro Ile Cys Pro Lys Asp Lys Pro Asn
    195                 200                 205 gtc gag ttc gac gtg gac ctc ggc cac gac ttg agc acc caa aat gtg     672
Val Glu Phe Asp Val Asp Leu Gly His Asp Leu Ser Thr Gln Asn Val
    210                 215                 220
```

```
ggc gat ctt ttg aaa ggg caa cgc agc gtt ttg gcc gat ccg ccg atg       720
Gly Asp Leu Leu Lys Gly Gln Arg Ser Val Leu Ala Asp Pro Pro Met
225                 230                 235                 240 caa ttg ttt cct cgc cat ttg ttc gag agt ggc gaa gct tcc gag acg       768
Gln Leu Phe Pro Arg His Leu Phe Glu Ser Gly Glu Ala Ser Glu Thr
                245                 250                 255 gcg tcc gac cgc aaa gaa agc atg gga aaa gga cgg aaa aaa ccg agc       816
Ala Ser Asp Arg Lys Glu Ser Met Gly Lys Gly Arg Lys Lys Pro Ser
            260                 265                 270 aaa gaa gtc gct gat gct ggg ctc acg ccc tcc gac gag ctg aac aaa       864
Lys Glu Val Ala Asp Ala Gly Leu Thr Pro Ser Asp Glu Leu Asn Lys
        275                 280                 285 acc gcc tca att gtg cca acg tcg gtg caa act ttt cgt cgc cac ttg       912
Thr Ala Ser Ile Val Pro Thr Ser Val Gln Thr Phe Arg Arg His Leu
    290                 295                 300 tcc gag acc ggc aac aga atg cga aat ttg ttc cgt acg aat aca ctc       960
Ser Glu Thr Gly Asn Arg Met Arg Asn Leu Phe Arg Thr Asn Thr Leu
305                 310                 315                 320 agc tat tcc ttt aag aag tga                                           981
Ser Tyr Ser Phe Lys Lys
                325
```

<210> SEQ ID NO 42
<211> LENGTH: 326
<212> TYPE: PRT
<213> ORGANISM: Heterodera glycines

<400> SEQUENCE: 42

```
Met Ala Pro Lys Cys Leu Pro Leu Glu Leu Phe Glu Ile Val Pro
1               5                   10                  15

Phe Ile Pro Ala Glu Lys Ala Ala Pro Asn Ala Leu Ser Ser Cys Leu
                20                  25                  30

Leu Leu His Asn Leu Leu Leu Pro Arg Val Ile Lys Trp Lys Glu Leu
            35                  40                  45

Lys Lys Met Ile Lys Glu Leu Arg Asp Glu Val Phe Gly Lys Ile Asp
        50                  55                  60

Glu Leu Arg Asp Glu Met Asn Gln Lys Phe Gly Gln Ile Asn Thr Arg
65                  70                  75                  80

Leu Asp Arg Thr Asp Gln Arg Leu Asp Gln Met Asp Lys Arg Leu Asp
                85                  90                  95

Arg Met Asp Gln Arg Leu Asp Gln Phe Glu Gln Tyr Gly Pro Val Pro
            100                 105                 110

Pro Pro Met Pro Leu Gln Ser Gly His Tyr Ser Gly Ile Glu Ser Thr
        115                 120                 125

Ser Glu Phe Ser Glu Leu Arg Gln Ile Gly Thr Ser Ala Ala Phe Asp
    130                 135                 140

Thr Arg Gln Asn Thr Gly Ser Glu Leu Gln Arg Arg Pro Pro Phe Leu
145                 150                 155                 160

His His Val Ser Glu Thr Gly Asn Pro Val Pro Ile Leu Ser Ser Ile
                165                 170                 175

Gly Leu Asn Ala Leu Phe Thr Pro Leu Ser His Phe Tyr Phe Gly Asn
            180                 185                 190

Cys Val Pro Ser Met Thr Ser Pro Ile Cys Pro Lys Asp Lys Pro Asn
        195                 200                 205

Val Glu Phe Asp Val Asp Leu Gly His Asp Leu Ser Thr Gln Asn Val
    210                 215                 220
```

```
Gly Asp Leu Leu Lys Gly Gln Arg Ser Val Leu Ala Asp Pro Pro Met
225                 230                 235                 240

Gln Leu Phe Pro Arg His Leu Phe Glu Ser Gly Glu Ala Ser Glu Thr
                245                 250                 255

Ala Ser Asp Arg Lys Glu Ser Met Gly Lys Gly Arg Lys Lys Pro Ser
            260                 265                 270

Lys Glu Val Ala Asp Ala Gly Leu Thr Pro Ser Asp Glu Leu Asn Lys
        275                 280                 285

Thr Ala Ser Ile Val Pro Thr Ser Val Gln Thr Phe Arg Arg His Leu
    290                 295                 300

Ser Glu Thr Gly Asn Arg Met Arg Asn Leu Phe Arg Thr Asn Thr Leu
305                 310                 315                 320

Ser Tyr Ser Phe Lys Lys
                325
```

<210> SEQ ID NO 43
<211> LENGTH: 40259
<212> TYPE: DNA
<213> ORGANISM: Heterodera glycines
<220> FEATURE:
<221> NAME/KEY: misc_feature
<222> LOCATION: (17816)..(21448)
<223> OTHER INFORMATION: Portion of the Super 385 scaffold that encodes
HgSLP-1

<400> SEQUENCE: 43

```
aaaaaagcgt tttattgatt tttaaagttg gaataaaatt taaaaaaatg atttttgctt      60
tatgatttta actattaaaa agttgtagaa aaaatttcgc ttttcgcatt tcgcttttcg     120
cattttcgca tattttggct tttcgcattt cgcttttttt catttcgcat ttttcagttt     180
cgcaaatttc gcttttcgca tttcgctttt tatttttcaa tttggcccat ccctgatata     240
tatggtgagc tgaagttaca ttatttaatg gttaattatt taaataccaa ataacttttc     300
atattttcgt tcattttatt tctaaaaact gaaatacctc gatttcgaga ttccgttttt     360
gtagccaaaa tttattaaac ttctgctcac cacgtataag atataaattt ttaattatgt     420
agcgaatatt ttaaataata aataattaat taattaaaat aattattttg ctcttttaat     480
ttgatcactt aaacactttt tcgtactttg ctcaactttg cactttcgta cttcgtctca     540
gcactttatt aaattcaatt ttcgctcact ttttctgttg ctggtggcca aaacggttcc     600
ggcccgtact gctgttgaaa ctgaacatct tcatctttgt acgtgctgtt gttgttgtcc     660
gggtccaaat tgagtatcag ctgggccagt cggactcgta ataattcctc cttggcctcg     720
gcttgggctt ttgacacggg ttcataaaaa catattaatt aatcattttt taaatattca     780
ataccaatta ccatcggccg tctcagtccc tccgaaatgg cgagaatggc acgctcaatg     840
cgttccgctt cggcacaatg gaaccgcttg ctatacgctc gtgccgcggc ctgctcccgt     900
tgcacgtccg ttagtgtatc gcgtaatgcg ttttgcgcgt cgtcctgcct tcgacgccat     960
tgtgctgtct ctaacgccgc gcggtcggca ctttgtgtgc gatgcatcga aggcgtggga    1020
ccgtatctgc tgggctggga tttagtgcga agggatgcgg tagcattgtt ttcaatggca    1080
ttttgagaag cggaggcgga ggagtagcag aaattgtcaa cggatggacg acgggggaca    1140
gtttgaaggc gactgattgg cattttgttg gccgagttaa aagtgccgga aaaggcctat    1200
aaaaattgga aataataaat caaaaggaaa aggtgctact tcggtcactc ggcatgtttg    1260
actccgtact gtcaccatcg ctgcaaattc cacactttcc tccgacggca ctcgtgccaa    1320
cctccactct tgagtgacgt cggacacacg cgagaaattg cactgggaag agctgtgcac    1380
```

```
caaatatggc acattgatat gctaaaggga acggggggaga ggggggggaa tgccaattaa    1440
atgtccttaa ggagggctta aatcattatt ttaacggaca aataataata aactaaaaat    1500
ttagctttca tttttcgtg tgtcattaaa ctcacttgga gtgaagcttt ccttccgctg     1560
gttgtgttct gttgttgctc aatattgttg tcaattaggc ccacaaaggc ttcatttttc    1620
tcgggcgctt ctgaaataaa tttgcattta attgatttaa ttttcaaac attgatttgt     1680
atttattagc tgcgcctatt agtgtttaat tgggcttaat tagtatctta attacctgcg    1740
ttctcttcgc tgttttctgc cacttctctc ttctgctgct gctgtcggc ccttcgaatg     1800
tttccggtcg gtgtcagcac aaaactcggc tgatgattct gtgccctcag agattggcca    1860
atttccgtaa aaattggtcc caaatcgcac acactgtcaa tgtatcgctc aacgggcggt    1920
gaaattgtca ttttgtcgcg tcgttcgctg cgattgtcac ccatttcgtt ttttctgttt    1980
ttaaaatatt ttaattacat tattatttaa ataaaatatt ctgtttattt tacgcacttt    2040
tccccgatt cactcattga attgtaaatg tttcgattgt ttgtcacatt taaatttgtc     2100
gcgtgcaaaa aattgacggg tccgctgaat tccactctca ccaattgccg atctgaccaa    2160
atttaaaatt gttgtatttc tggtaatatt tgaatcactt tgtgtctctg gcgaagtgtg    2220
catttgtgcc ggaggggaaa cggtccccga ggcacccatt aaattgcgca cttcgtcatt    2280
agcttgatgc tcggaaaaag ttgccgactc gttcaaagtg ggtcgtatcc tttgatttcc    2340
taaagtaaaa aaaaattaa tttttatgagt catccataca attttttatta aataattagg   2400
gaagcgccct tcggggttgg gttgcgaaaa gtcagtgttt ggtcccatttt gatgtcatga   2460
aaactcgtaa aatggcaact cgtacaatgt tgtacaaagg caactcgtac agttgcttag    2520
gttaggcgca ggcgttaggc ttacaaagga gaggtaccca agtgaccatg ggacttccga    2580
atgaaacttt cagggtaggt agattacccc ccctttgtat tataaatttt tttttatttt    2640
tgctaaatga agcttctggc cgagatatga agcttttcct ttttgccttt tatacgagtt    2700
gccattttga cccaccattt tgggtttagg cgggacgaaa ccaaatacta attattataa    2760
tactaatttt cactaattat aatactaatt acaatactaa ttataaacta attattattt    2820
aattccctct catttccttt gctttaccct caacgctcac aacactttgg aacatttccg    2880
cttgtgaatc actcattggc catatgcttt ttgcggccaa ttgtcgtgaa tatgcgtgga    2940
atttgcacag attgacggag cattggacgg actcggcaaa aggcgcggca caaaacgatg    3000
ggaaagagga ggactaaaaa gtatcacttt tgaaatttaa acagcaatat tttttaccaa    3060
atcttgttgt ggctttggtg ccgtttctgg cggcatcttt ggcatttgct ttgtccattg    3120
cggcaaacat tcatacgccg attgccattc atctccactg cttgatgtca ttggtggggg    3180
cagaaaatgg gtggactgtt cttgttgttg ttttggcaat ttgtcaaaaa tgggcatcta    3240
aaagccgaaa aaaaagatag gggtaataaa gatactttaa aatgtgcgaa aagattaggg    3300
gtaattaagg gtaattaaaa ttttattaat tgaaaataac ttatttaatt agtcctcccc    3360
aactttcccc ttgtgaactg actctgtgct gcgacgtcgt catggacact gacatttcct    3420
ccttcggcgg tgccattgcc cagggctttg tgccgttgta cgtcgcctgt ggaggcacac    3480
ttttctgccg cgactgcggt gccatcgtcg caccgctgcc tccgcttatg ctgtcggtga    3540
tgaacgggcc gaacaccggg aacggactga agccgcgcga gttggcgctg cggtcgtacc    3600
gacgctctac cgcgtccgcc agctgatgaa cactttggac gagttggggc ggaaagcggt    3660
ccaacaccaa ctcgtgcggc atctgttgct gcgcctgcaa caggcggagg cgttccaacg    3720
```

```
gaggcatcga cgagtgttgc ctgaagcaaa gtgccaattg cacgcagtct cgatttcgcg    3780
aagcgactcg tgcgatttct tttccaaata ttaaattttt tcccgacagt gccagcgaat    3840
caccgatttt tatttcctaa aagttgactc gctcgaatat cttaaaatta gcattttttg    3900
gcaaaatcta ttaataaatc cttcaaaaac caatcgggga ctcttccctt actgtgccgg    3960
gctctgtttt ttgcttactg atattcgctt tgcataactc tgaaggggag ggcattaaac    4020
aaagaaagaa ccacgtgaca caaatgaggt aaaaacgcat cattattaaa ataaaaatgt    4080
tattaattcg aaggctcaaa atcccaaatc gtacaattaa aagttgtcat tgttcagcta    4140
aactaaacgc atttgctttt tcatcattgc ctccgtgaag gattcacaaa acgaaaagcg    4200
ttaccaactg agccacgaaa aggcacgaag acaaaaaaga ataaaatgca aaataaatgt    4260
tttatttttt gtggtcaaat ccccggaagg tccgtgccgt attagtgctt ttgagttttg    4320
agccgagtcg gggggggggg gggggggcgt ttcagcgaca ataaatattt taaaaaataa    4380
taagttaaaa tacgcaaatt tagaaaataa aaggttaata aaaaaaagga aaagtattaa    4440
atcaaaaaaa cttattaact aaaaaaaaca ttttaacaaa aaaagcaaaa aaagaaacag    4500
aaaatacaca attttaaatt ccatcactat tgaaagcgtg ttcaatggag ctttcaaggt    4560
cgttaagctc aaatctggca ttcattttgg caaaaaaaaa gttttttcaaa aattgttttt    4620 ttcgctcaaa aataaaaact tagaatatgg ctctaataac ttgaaaaata gcttaacaac    4680
cagaaaaaaa aacttgttttt tcgtgtgttt cacaccactg gtagcccaag ggcctatttc    4740
aatttccgtc aaatcattga ttagacgtca aatcaaacaa cctgtttcaa tttaaaatca    4800
aaggaaacgt ttgattatca aagatttctg tttcaatttc ctagaaaata atttagactt    4860
tttatgtact gccttcagaa ttttttttgag atttgcaagc gcgtttatga aaatatttaa    4920
tattcgaaaa gtcgaaaaaa aaccaaccgc gccgatctct gcttccacac ccattagtaa    4980
attgggaata tttttcggtta aaaaatggat acattgaaca catttttgat accaacgaaa    5040
aaaattgatt taaaggcaaa agtttaaatt gaaacagaat gacatcaaat cgttgatttg    5100
atgcccaagc ggcgtcaatt cgttgacgct attatttgat gtcaattctt tgatgttttg    5160
gaaattgaaa cagaaaaata cggtatttgg catcaaatca atgatttgac ggaaattgaa    5220
ataggcccca gaaaaaaagg caccgagatt cgcgacgcgt tgtccgcaac cgcgcgagat    5280
tttctgtccg cgctccaccc cctgttttac accttttttac accgcatata ttaaatttttt    5340 taaactccaa ttatttaaaa aattacttta taaaaaaaat ttactatttt cacaattttc    5400
ttagtaagcc aaaaatttaa aattatttaa cacaattatg tgtatttatt tgcccagttt    5460
tttacaatat ttaacaacaa ttccacactt ataattattt actaaatttt aaactgtccg    5520
caaatgtccg gacgcgatat ttattgtaag tataggttaa caaatgaaaa caataattgt    5580
cttacgataa atctgatgtc agattatgtt cagcaccaca gaaaacccca tatactaact    5640
ttaaactaga gtagagcggt accggtactg gtactgaaaa aaacggtaca actgagtacc    5700
tagtaccggt tttgaccggt accggtacta gtaccgattt tttaccggtt tcccagcca     5760 aaaagtaccg gttttttcaac ccgaaaatta ccggtaccgg ttttttttac aattaccgat    5820
taccgctcta ccctactttta aaccaaaaga aaaaagttcc cccttcttca ggattgcctt    5880 ttttcgtttta attttacgta atttgttaat tttaatttta tatatttaaa gcactaatac    5940
ggcacggaac tgtccccgtg cgaatacgca cgaattccgg ggatttgaca ataaataata    6000
aatgattatt atttattctt tttgtctttg tgcattttcg tggctatagg ctacgtggga    6060 attttttgaaa ttttagtccg ttctttgtta atacataggt tttgcgccat aatggtcaat    6120
```

```
tgtctgtgtt ttttaacatg acttttgat ggtttgatag gcgccgtcgg agggaaaaat    6180
taattatttt aaataaagtt gctttagaga tttaaaaata actgaatatt tttaagaatt    6240
tcaagaataa gaataaataa tgttaacatt cccaaattat taccctctg caagggcgta    6300 gccaggacct tcgtttcggg ggggcccaac tcaaaaagtc ggctcttagg ggtgtatttt    6360 ttcgttttg taaacctcaa tatttagagg tgtattttcg tgttttttt aaattgaatt    6420 gattgcatta gacgcgttca attgtaaatg atatgttttt tttagctacg cccttgcccc    6480
tctgtttaca aaaaaatta atataatatt taaaaataa ataatttt tttaatttcc       6540 ttttttattc ctcccctga ctctttcttt cccctctttc tccctttt cctaccattt      6600 tcgttccaca aattgttgct gccgttcgct tgtccgtttc attgccatca ttctgctata    6660
ttgccgttgt tgttgctgtt gctcttcccc ctctttggt tgtgttgctg gtactgcttc    6720
gtctccctcc cccaaggttt ttttttgcgg ttggcattgt cctcccccat tttcaccatt    6780
taaattaaac tgttcccgaa attcgaatag cttttgttga tgagttcgaa caaatttgtc    6840
gtcctcaaat tgttcagaaa actcctgaat aaaaattgaa attaaattaa attccttaaa    6900
agcttaacac tttttgctcc tctcggatat ttctcggctg atattgccga ggctcgcgtt    6960
gcagcggggg aaattcgttg gaaagctgaa gaaggtgctg ctgatggtca tccattaaat    7020
tgggatgaaa agcatcctaa accaagcaaa attgatttt aattaataat taattgacaa     7080
taattagcgg aatgggcatt tattaaccca aaaaaacacc tgcaaagatt gtgtgaaacg    7140
caatgacttt ggctttccat tttcatttc accataaaat tgttcttcat gctgctcact     7200
gctgctgctg aactcttccc ggtgtctgct cgaaaatctg acaaaaatca aaattcaata    7260 ataattaat ttatttaatt tctaaattct ttctattact ttttgtattc tgttgttgtg     7320
gttgtccgtg ttgttgtcgt cctttcatgg cgtcgttctt ttttaatttt ttgaaagaac    7380
ggtttctcag tgaatcgttt cattatcgtt tataaaatct tagcatttat tttaataaaa    7440
tatataaaag catattggaa atttattcag ccataacggc gatgtttaag ttgttttaaa    7500
atgaaatggc catcaaaaaa ttaattggtg gttggatttg tttaaccaat ttaattaccc    7560
ttccttttaa caaatacact cattagttaa tgagcacatg ctcctcaccc caatgatggg    7620 ctatttttg cgaaatttgt gagaaagtgc tgagaaaaat ggccggggac aaatgctctc     7680
ccaccaaata ataagcaaag tgaaagccca ggggcatttg gccgattttt ccggaggcat    7740
ttcggaattc tcccggggat ttttcagtca gtcgatgtgg ccaaaagaaa cgaatcatcc    7800
gcctttggcc atccggacca aggaatacg aggtaaagct ggatgatcat tgagtaacaa     7860
acagacgggc agatgggcgg aaggaatgat cagagcaaaa gtgagaggga ctaaagtgat    7920
cggacgaggt gagaaaagtg atcagaggga agagagagtg atcggaagaa agagagagag    7980
agtgatggaa atggcgagag aattaggaaa aaaatgtatg ccaatccagt gatgaatgga    8040
gttgaatgcg ttgattccga cacaaaacta attgtttaaa tgaaaattcg aaagaatttt    8100 aaatttatc taataataat tgaattaaag cataaatcaa ttgttccttt attcaaagat     8160
ctctttttaa gcttgatgag aagtgctatt tttactgacg tgacaatcgg gaaacgaat    8220 tgaatttta attatttat atatatttga atgcttcgtt ttattgttta cgtttaaata     8280
aggcataatt aaaattaatt cgttttcaaa tgtttaaatg ggtcctccct tttgctaatt    8340
ggatttgtta gagcgataat tttgcttatt taaatagaca aataatttgt taaattgcat    8400
tcaaattttc catccattca tcatttacca atgtttcccc aggttttct ttttcccata     8460
```

```
attcttttt    gcgtttcatt   gtcagtgagt   ttttcatata   aattaattttt  acttttaatt   8520
taatttaatt   ttttaattt    tatttttttc   agaatgtttc   gtcgtcccat   cggcgatttg   8580
gacatttatc   tgaaaaaatc   gaagtgaatt   ttttaacttg   aactatcaaa   atgggttttt   8640
ccaattagca   tcacgccaaa   atacccacca   ttttttttc    tttgcaggat   tcgcaatatg   8700
atttccacgc   tttgaaagag   cgaaaaagat   tgggtcggat   ggatgaggaa   aaggtaaatg   8760
aacattccat   taaataatag   attaattatt   attttttcata  gcttttttgct  gcttctgaag   8820
agggacgaga   aatggaaacg   aaagtttcgg   aaatgaaaag   catcagaatt   gggcaagaat   8880
acgaaatgca   attggcaaaa   tggctggacg   cgtgcgacat   gcgaccgctg   agaaagccaa   8940
ttacggtgag   agaagcgaaa   ggaattgaca   caaaatgacc   ctaattggca   tcaattgcaa   9000
tttagtccct   gaatgcctat   gaaattgccg   cgttaagcat   ccatggaatt   caagaactga   9060
tcagcgaagc   actggccaaa   attggtgtcg   atgttgacaa   ggtgaaatta   aaatatttaa   9120
ttaattaatt   attttaatt   taatttaatt   tttaggaatc   ggtcaaatgc   gcttcaaaag   9180
cagtggcaaa   ttacaaaaaa   gtgattatgg   cgaaatatga   gatgagcgaa   aaaagtgaac   9240
gaaacactc   gcgtttcggt   gccaaatcaa   ttttgagag   tgccgaaaaa   tgaacgaatg   9300
aatggaaatg   gaaaagcata   ttaaaactaa   ttttgtgat   ttttggggtt   attccttact   9360
aaattgtaaa   aaaattaaaa   aattcgcttc   tctccccctt   ttaatatttt   tgaggaaaaa   9420
taattataaa   aaattgaaaa   aatattttta   aatataaaaa   ataacttaaa   acagcaatcg   9480
cattttatcc   aacagaaaat   ttgtccaaac   aaataaaaaa   tgaatgaata   aataaaaatg   9540
actagggatg   gaattgttga   caaaaaattg   tcagcacata   taggcttcga   aaaagccccg   9600
aaaatagcga   aaatgacttc   gaatttctga   ggaaaaattg   gtttacaaaa   cggagcatca   9660
attaaatgct   aaatccagta   attagcaaaa   ttttaaaatt   aaataacttt   ttgtacaaaa   9720
atcgtattga   taaaaatgaa   tttaacaatt   gaggtaagaa   ttttttgttct  gaaattgtct   9780
gttctgtttt   atatttcgtc   gcattgtaaa   gccaaaaatt   ttccattttc   ttttctctag   9840
gaggtgggga   aaaggtcaaa   aattctatcc   ctagtgattc   aaattccgta   ttttgtcaaa   9900
aatttccata   aaaatgccag   aatacggaac   cacccctacc   cctttctgct   ggtgatttgt   9960
ttgctatttt   tagtgcacgt   gcactcccgt   gtgctcaata   acaaatttgc   tcagaatatc   10020
gtcatcctcc   ttctgttggt   ccttcccatt   cgcatactgt   acatatttgt   ttacggtagc   10080
gacgtcgatg   acggcccaat   tgccacccaa   caattcgttg   acgtggccaa   tgacgtcacg   10140
gtgggagacc   agcacaatat   gttcggctga   acaaaagcaa   agtccaaaaa   aagtataatt   10200
aaacgattgt   cctaattggc   aattaattgg   cttattaccc   aaatagttcc   ataaaaaaca   10260
attaaatggg   ccaaattggt   caaatgggtg   gctgagttaa   agcaatgttt   gttaatccct   10320
gctgagtact   gttttggccg   gtgactaatt   atccgagtca   aaaaaatgca   ttaattttcg   10380
taccattttt   gttttccgtc   aaaatgcgtc   gcagtgtttg   ctccaccaca   aaatggcagt   10440
cgctttcttc   cttccgctta   ctctcttctc   gttccgcctt   aatcagcttg   agtgctctaa   10500
aaaggcaatt   aaaatataat   taaaattaat   tagaaaaagc   aatgaaattt   aaaaacatttt  10560
ccatttaaat   aataaattaa   ttcgatttgc   tcacttttcg   ctgtacatag   gccaatagtt   10620
tgggtttgtg   tgcggaaagg   ctttgtcttt   gtgcagctcc   gtcagttttt   tatgtccaat   10680
tttcaaatcg   catggcttct   cgaactgaaa   attcggattt   tatcaaatgt   attaaaatat   10740
tttcacactt   cgctaagtcc   gggctcaatg   tgaacgaacg   cgcgatggcc   ttcgcccagc   10800
agagaagcgg   cggtttgcat   tgtccgttgg   aatggcgacg   cgaacacttt   ggtgatgggc   10860
```

```
actgttttga acctaacgcg aggaacgggc atagttttt gtaaatttgg gctgatcact    10920
cgctgatcag gaaaaccaat ttgaatttt gttaattttg agactttgaa attttattt    10980
tgaaaacagc aaagtcttct ggctttaatt tttaaaaagc gagatacttg acttttgttg    11040
gaatttaaat tttgtgaaag tggccacata aaattaaatg ttccaaaaag tggccaaact    11100
tttgaaattt aaattctatt tttcaaatta aatagtcatt tcttaccatt tgcccagttc    11160
tttcgcctgc tcttcgcctt tctctgtcag cgtttcgtct tccgttccgc catttctttt    11220
ttccgcgtgt cggaccaccc acacaatttg tcggattgcc ggacgatcac ctgcaaaaag    11280
tgacaagata atttaataat tagaggcgac atttccgct tctgtttctg tgataaaaaa    11340
attttcatt tataaataaa atttaaaaag aaaggcattt aaatgagccc tttgaactcg    11400
taaatatttt gattgtcgca tatttttaaa aatagaaaat attattatta ttattatttt    11460
tgtttaattt ttttactaat tgtccatctt ttctcctgat tatgccacca aacgaattca    11520
aatttgttta attcgtcctc aattgcttta agtcccttca aatattgttc atttgtgtat    11580
gtctttgttt tgcctttgtc ggcatagatt ttttcaaagg aatttggctt ttttgccagg    11640
aattcttcta aaaacggaag ttttttctca atttgccttt tgttgctttt taaaatctgc    11700
tcgaattgct ctcttttccg catatatctt tcgaggtcca acactttccg ttcttttttgc    11760
aaatttctca ttatctaaat cccaataaaa ttaaaaaatt aaatggaatt ggcaatttaa    11820
tattattaat attagtattt attgtataat gtctgtacca ttccaatttg ttttctgttt    11880
ttctcattgt cttcaaggaa tttgtcaagg aaaaacagac aaattgtggt catttgggtg    11940
tcaaaaatgc gctcaattat gtcaaatttc tcatacggaa gatcatattc gaattctgtg    12000
atatcacctt cctgaaaaag tccaaagttt agaaaattt agcaatttct tctctcctcc    12060
caccaaaagt ttttcttct ttatttgtcc ttaggctata gacaaaatta gtcattttct    12120
cattaaccca ttaattagtt ttaggcatgt taaatgtttg ttttatcata aaaacagtta    12180
tccgaagttt acatattttc tttttgtttc gtaaaatgcc attctctgga gggtgtgcat    12240
cagtgtggca cggaattcag acttccgatg ttttaaggtc tcggaatgcc tgccatctct    12300
gatgtgttgt cttaacacag ggctctcatt cgtacttgaa tggcaagtac gtacttgaaa    12360
attggattca tgcgggaaaa tttgaaattt gcttatttc aagtttgtac ttgaaaattg    12420
cggcgcctat tggcaccgcc ggctaatttc ttaaaaaaaa cttgcttaaa ctcgaaaatt    12480
tgtcttttg gggaaaaatc tgttaacaaa aaatgacagt ggaaacaaaa aaaatattgg    12540
aaaaatccaa cctggcggaa aatatgacct tctgaattaa atatttacca ttctttcgca    12600
tttttttcgcg tacttgaatt ttgtgttttt atctgtgcag ttaattaatt gtaataagta    12660
gggatacgat ttttaaatca cccctaagaa aggacctaaa aaaatttcaa aaaattcacc    12720
cctaagaaat gaaaaatttc tcaaaaattc atatccaaaa tttatttttt tgacaaaaat    12780
tgtgatttta aaaaatattt agtctcaata ctgatttggc ttaatttgtt aatttttgga    12840
gaaaattta gattttacac ccctaaattt gaaacttttt gggacctatt tgccatttt    12900
tagcacttat ttgggggggtt tttagaacct aaaaatcgta tccttattaa taaacatcgg    12960
attttgaaaa atcttttat tataaattat gattattttt ccgtgtgaat ttttccaacg    13020
gtgaagaaat tttaacgaag ctattatatt tgcttggccc attaaagtat taatcgctga    13080
aatttgctgc catttccatc cctatttcg tactttacgt tattttattt ttactttcgt    13140
acattaaatc gaacggccgc ttggtcaatt tcaatgctgg caatatgtct cgcttttgac    13200
```

-continued

```
aaagactcgt tcaatttgtc aattttttgt tgaagttcgc gcatatattt aacgaaaatg    13260
tcttaaaagt cagactaatt agttaatcac ggcaattcaa ttttgggctc caagtacaat    13320
taagttggtt ttttcgtctt agtggtctgt gagttagtca ccaaaagggg ggtcccaggt    13380
tcaagtcctc cctatgttgt gtgttaattt caatttcttc ttttaaaaaa ggcagaatta    13440
ttttttcgtt aataaaagtt ttcgtggcaa taaaaaatca tattcaaaaa gcgttggtta    13500
cgtccaacat cgacaatttt atgaaatttt tttagcttat aacttggtga atactagagc    13560
aaataaaacc attttatgct cattttgaag ggaaaattct ggagaatatt gtaaatttta    13620
tttgttttgg ccttaaattg tggactcggc taaaaaagaa ttaaaattat tgaaaacttc    13680
acctagttga aaaattttc cctatgttca aattttcttt aaatttcgca taggccaata    13740
ttttgactcc ctctatcgga tccctgttta ttttatggaa cttaagtttt taactcgaga    13800
tcggctcttc tattttaca agggaaaatc taaaaaaaat caagttttgc aaagttttgg    13860
cgttctgatt actaaagaat aataagctta tttgcactgg gagcccaaaa ttgaatcgcc    13920
gtgtaattaa ttaattggtt ttatttaatt tgctcacctt cgtatccttt attagcagcc    13980
atgttgaaaa tcagatcgat tttgtttgct tccttctgat agcccaccgg tgtgttggca    14040
cttttggttt gaattgaacg ggaaaggtgg tcaaagctt ggacaaatgt gacggcatcc      14100
gccattccga tgaacataaa atgtgtgaat tttaatgga aattaattat tattcattta      14160
ttatttattt tcctacaatt tttcaaaatt tgacgatgat aattgtccgc tgctactggc    14220
cgaactttgg gcagaatctg tgggatggac gggcagaagt ccaacaaaaa ggcaaacgga    14280
gaggaggagg aaaagcataa tgctaaaatg aaaaagggga aataaaataa aacaaaataa    14340
atatttgcat aaatgaataa ttgtaattgt gcaaatcgaa atttatagac aaaaaaagag    14400
aaaagatgga agtaaagcag tagatagagg gtggcaaaag aacgtggata ttggataaat    14460
ggcaagaaaa tggcgattca tcgatcattg tttgacgtaa atgccatcct ttttctata      14520 ttttcattat tatattacgc tgggactaac attagcattg aaaagggcg ttatttaaaa      14580 aaccatcaaa tggaaatttt caacaaaaaa ctgctcaaaa cttttgtcaa tgtcaaccaa    14640
attagacatt cttggtatca ttcgatagcc ctaacatttc tctacaagtc atctaaattt    14700 caaaaattt ggttaagttg agaaaagtta tggccaaaag tacgcaagat aacaagtttt      14760
cacacatttt tgaccataac ttttttttaaa ctcaataaaa ttttttgaaa ttttgcaggc    14820
taatagagga cacgtagggt tatcgattaa tagcaaaaaa ataaaaaaca aaataatttt    14880
ctaacagaaa ttttttaatt aaaaataaaa ttattttgat cataaaaaat tctgatcaaa    14940
actttctcag aaccaacaaa attaataaag cttgctatta tccgatagcc ctacgtgtcc    15000
tctattagcc tgcaaaattt caaaaaattt tattgagttt aaaaaagtt atggccaaaa      15060 atctgtgaaa acatgttacc ttgcgtactt ttggccatag ctttgctcaa acttgaccaa    15120 atttttgaa atttagatga cttgtagaga atgttaggg ctatcgaatg ataccaagaa      15180
tgtctaattt ggttgacatt gacaaaagtt ttgagcagtt ttttgttgaa aatttccatt    15240
tgatggtttt tttatattgc gtgttgtgtg cgtggtaacg ctcgtaatat gcagtcggcc    15300
acacgccaat tggataagga caggcaattt ttttcatttg ttttttgaatg gttccgtgtt    15360 cccttttaag tttccagtgt tgttgccatt ttttaaattt ggttattcaa gatgcgctca    15420
aaaatcaatg ccttctgaa attatcttga aggcaaatga gtggactaaa gaatgccgaa      15480
aaccctaaat taagaaatgt atggagcgac accaagagca attgaatatg ccgaaaaagt    15540
aacttgtttt ggtaatttct ttccattcta attcaaattc ggccaatttt aagtcagttc    15600
```

```
cgacgagatg gaattcgacc taccgaatgt tggcagcttt caaagagcag aaaaaagttt    15660
tgctggcaat gcaatttgaa agagaccaaa gaaatgccgg aattttgtct gcaccaaaaa    15720
aacctcggat ggccgagatg gaaataattt catcattgcc gtccatttca ttcaaagact    15780
tcgaactttt gcgccaaatt tgcccaattc ttaaaatttt tgacgtggaa acccaaaaag    15840
taaaaatttt cattttgctc aataaacttt tagttttaag ttatcccacg aaaaatcaac    15900
ggcttctgtg atattgccga ccatcaagcg ccttcacgat ttttactgaa agaaaaattt    15960
ccaacaatca ttcagccatt aatcgatcat catcatcatt atcctctcaa ttattcctaa    16020
ttacccctct tccgaaaacg acctcttccg ccccatcaat ccccaaatcc gtgcctcctc    16080
ctcctcttcc tgtgcatttt atcccaacat tcccatcacc tatcgatcct ttccaattct    16140
cgtcagccat tcagtctcgc cccactgcac acaccggcga gagtttcgcc attttccgct    16200
tccaattttt attgcaaatt ttttattttt tattttttaca aaatgaaaag cgatcaaatt    16260
ttgatttaaa aaccatctaa aatattctct gaggctttcg ggaattgtct aattgtaagg    16320
caataataga aaaaaactta gagccggcaa atgtattttc tcggttacag taacactacg    16380
attactgtta ccgttttttaa gagaaaattg cgtcgggcat tttatcacga caattggcat    16440
ttttaattat ttttatttag aaagttccct tgtgaattgc cgattaaatt accattaata    16500
ttttaattgc tactgtattt tgatgatttt ttaaatcctt atttaataat tttgtgagtt    16560
aatttgggtg agttttttaaa tgtccaaagt ttatttaaat tcaaatatta tggaaaaaga    16620
aaagcgattg actaaatgat atattgttat atgcggcaaa ttttgagttt ttcagaattt    16680
tcccgctttt tagacacttt ggggcggcca attaccataa agaagtgatc tgacaatcgt    16740
tctaaaagct tttctgatca gcaattttta ttaaatgcct caaaaatcca aaatttcaca    16800 ttttttttcga aaaaatcggg ttttttcaaaa aaaaagctat caaaaattaa ttttttaaata    16860 ttaaaatgtg attctaagcc tatataggca ttttatatgg cattttgtgc atgcttcacc    16920
cgtaaggaag aattttccaa aattggaacc ctagtgataa aattatcttt ggaaatatat    16980
aattaggtaa atgccgaaaa gcaatgacat aattttttga atgtggaatt tcttttttgtc    17040 ggcttttttgg cgaggcggca aagtcaaaga cgcgcatgga tggacattcg gagtaattaa    17100
tgcataatgt aaaatttaat cttttcacag ggctaatcag cagttgatca atcttaggga    17160
ttatttgcta tcagagtata taaatgaaat gagaactgta caattgtcgt gaaaatgaat    17220
gccattttca gtgtaaatgc cctcctcccc cctttccct gtgccattgt acgattgtaa    17280
atcggtgact gtggctgctg cgggtcattc atcagaaagc gttgataatc acaagccctc    17340
ctaactggca aatgccaatt aaattttaaa agcttaagca aaaatgtctt tttaaaggtt    17400
ataaaaaatt tggcttctcc catacagcca tacattgctt tggctattct gttctctgcc    17460
cattgactaa cccattttg tcgggaacgg agagaagcat agaaaaagag atagagttag    17520
tcagaagtga aagggaggcg agggagcgca gacagacaac gaaaggaaag ggagagatca    17580
cagacagaca aatttagata gagaaaatga aaagtgaga gtgcgcaagt gagaagcgaa    17640
aggaaaagcg aaacaacaca gaagagaatt gctccacgga agaaaagcga ccggccattt    17700
cttctgctgt gggacaaacc caacatatcc gctctgacaa cgtccttccc atgccagtca    17760
actaattagc cactaattag ccccattaaa aaactgtccc ctgcttctct cgacaatggc    17820
ccccaaatgc cttccgctcg aactgttgtt cgaaattgtg cctttcatcc ctgccgaaaa    17880
ggccgcccca aatgcgctct cgtcatgtct gctgctgcac aaccttttgc tgccacgtgt    17940
```

```
catcaaatgg aaagaggtag gccctgccat atttgggaca ccaaggaatg ggctcaaaat   18000
tcaattgttc acttccggtc acccacttga aaacacacag gaatgtggca cgatgttctc   18060
atattgtctc tctttaaaag aaatttcatt taaattgctt aacttcctta aatctttttt   18120
ctatttccat caagtagcag gctgttatca ctattagagc ccggacacaa aaaggcaaca   18180
aaattgtaaa tttttagttt aaatcttaaa gatattgggc caaaaatttt ccatgtatcc   18240
ataggcgact atcggcaccg ccggcgctcc caaattcgcg ttaatttttt aaatttatta   18300
tgaattgaca aaaatttttt gatttcaaat atatcgagct tcgaaatttc gggttttgg    18360 gtttgaactt gcgttagcca tcagtttcga gtgctaagcc gagcttcgcc cgtccctgtc   18420
tcagaccagc aggaggcccc atttcttatg ctggactaga actgatttttt ttaaaaactc   18480 ccaggaacca gacgctaaca ttcgatagcg caaagttttt tctattagcc tgcaaaatca   18540
gggctaatag agcatttgaa gggcttaaga atgataccaa gattattaga attggttaac   18600
aaagaaaaaa gttgtaatca aaatttgggc tggcaccga aacgccaaaa cggccaatcc     18660 cttttttag atttaaatgt ttggccttct atttcctaat aataatttct tattttttac   18720
ttttattgta atcgttttca agaaattgct tgaatttaga taatttgatt cacatgaaaa   18780
atttagatta ttctttttatt tatttaagtt gaaaaaaatg ataaaagagc ttcgagatga   18840
agtgttcgga aagatcgacg agcttcgaga tgaaatgaac caaaaatttg gccaaatcaa   18900
cacgagattg gaccgaacag accaacgact cgaccaaatg gacaaacgac tcgaccgaat   18960
ggaccaacga ctcgaccaat ttgaggtaat tttgacagat ctaagcttag ttgtcggtag   19020
ttctgctttt gggcttacat ttattgttgc tgggtttgtt tatggaccca ttgtactttta  19080 tttctcaatg tttggacaga ccatacattt aatctcattg aaacccaatt cggggcaggc   19140
gcttttggtt agcggcgttc gttccccaaa aaatgaccag gattcagtat cgcgtttgaa   19200
taatttccct cccctccact gatcagcagt atggccctgt gccgccaccg atgccgcttc   19260
agtccggcca ctacagtggt attgaggtat attcccaaat tttaattttc gggaggaaac   19320
gacgcagacc gcaggttggg aaaacgaact gctccgcttg ttttttggcg ttttgtcggg   19380
gccaaaattt gaaaatgcaa ttccttgaat tacaaataca caattcacag tctacctccg   19440
agttttccga gttgcgccag attgggactt ctgccgcatt tgacacccgc caaaacaccg   19500
gcagcgaatt gcaacgccgc cctccatttc ttcaccacgt gtccgagacc ggcaaccctg   19560
tgccaatatt ggtgcggagc ttaactaaaa accttttccta ttgataaatt tttcaaaaat   19620
tttcagacta ggctgattaa ctataaattt ttgtgatatc agactttcag agttcgatcg   19680
ggctcaacgc tctgttcact cctctttccc atttttattt tggcaactgt gttccgtcaa   19740
tgacgtcgcc gatctgccca aaggacaaag tatatatttg gtcgctggtt taattcacta   19800
cggcttaggc ttaattgggc cgccccccac tctccgtacc ccatattcag tttttcaaaa   19860
aaaaaaaaaa tcaaaatggc gtctatttta caaaatttgt agccgataaa ttactgtttt   19920
tgccatttgg tcactatttt tcaaaaatga taaaatgtgg gtatcgcagc tttacgttgt   19980
acaggtcagg cagtgccgtc aggcaccgtc gggaaaatta aataaagcaa tttgttaaga   20040
agaattgctt aaaattttaaa atgaaatttt tagtttttttt gggcttaggg gggggggcttt   20100 agcccctcaa tccctcctgt gaatctttttc aaggattagg cagccatttg cttttggtca   20160
tccccagtag tttttttgcat aagatatttt ttcacgtttt ctctttgaaa tatttttagt   20220
tttcgggagg aaataaaacg gcggtgaata tcatgggccg gttttttgac attttctgta   20280
ccaaaatttg aaactgcact tccttgaata caaatgtaca attcacagcc caacgtcgag   20340
```

```
ttcgacgtgg acctcggcca cgacttgagc acccaaaatg tgggcgatct tttgaaaggg    20400
caacgcagcg ttttggccga tccgccgatg caattgtttc ctcgccattt gttcgaggtt    20460
tgcaacagag cgccaaaatt ggtgtggagc ttaactatag taagaaccca tcccagggat    20520 aattttttt caaaaacttg aaattaaaaa aaagttttt gaaaaagatg aaatgttact       20580
gacacaaact ttgtgaattt cggaaaaaac ttacgcctgc caatttttaa tgtaaaattg    20640
ttgaagagtg gcgaagcttc cgagacggcg tccgaccgca aagaaagcat gggaaaagga    20700
cggaaaaaac cgagcaaaga agtcgctgat gctgggctca cggtgataat attttggctg    20760
attacgttag tcaatacctg actagaatt tcaactattt ttttttgaaa atgtaattat      20820
tcatattaaa atacaaaaaa aatttagaaa aaaattccat tttccttgaa aatttctta    20880 aatattttt ctaaaatctc aaagtttgac aaaaaaaaga agttattttt gatatggagg     20940
agggaaacgg agaggggggg ggggggaaa cgttgagcac ccataaatac aacaaatgca    21000
caaatcacag ccctccgacg agctgaacaa aaccgcctca attgtgccaa cgtcggtgca    21060
aacttttcgt cgccacttgt ccgagaccgg caacagaatg cgaaatttgg tgcggagctt    21120
aacaaagaat ccagcccagg gaatttgaaa atcataaatt ttaaggacag caaaaattat    21180
tgggattcaa aattggaaac acaatttgca aaaataatga ctaaaaaatg ttaaattttg    21240 acggtttta aagggaaaaa aactaaaatc cggaaatttt tcaagattat tccctgatga    21300
gaaattccat gggatgtgcc aagttcaaat tcagagcaag tggcgaattt ggggcggagt    21360
ttttaagatt tttggacttt ctttccattt tccatgatat gttttcagt tccgtacgaa     21420 tacactcagc tattcctta agaagtgatg gaattccatt ttattttgtc atggttgttg     21480
cgagttcttc actattttt ctcaggaatt taatttaat tttttacat taattttgg         21540 cttaatttct cttaatttt gttttcttt tttgttgatt tagcacttt ttcgatcttt          21600 tggttttaca ggtctgtttc acttctgaat aaacgtgtac ttttttactt ttggtccacc    21660
acttttaagc tttgaacgcg atttcaacaa aattttaaaa tgctaaactg ataatccaaa    21720
taactgtcct catctgactg taggatttgg aaaacgaaga aaacccaatt aaatttcaaa    21780
aataattaag cgtagaaaga gattgtatcc gatcatctga tttcggctaa cagggcttga    21840
aggaattaac tttgaatcgg atttttgggca aatgtcggtg cttcggtgta ttacattact    21900
caagcccatc aaaatgggcg ttactcaata aagcaaatga aattcttctt gaatagattt    21960
aagcatccta ttagcccaat agccctacga attctcttct atcaatcaaa ggttaggtgc    22020
caaaagaaaa tacggtccat gtgattgtaa agcgcaatta attcacacac atttaaatgc    22080
attttctctt tacacattcc ccgcttccgc tcatttgtcc cttcccacgg gttcgtctat    22140
ttaaatggaa gcattccctc gggagtaagt cagttgatca actagtcgtt aatcagtcca    22200
ccggtcgacc atccatccaa gctgcataga ataaagcgct aacatttacc gccgatttat    22260
gactggtccg gacgcggacg gatttgggct tgggacccgg gaggttggga gtccagggcc    22320
cggattttca cccaccaatt cccgcttctc tttccctctt ccattcctct gcacttcctc    22380
catggtcctt aatgggcatc tctcttaagc tctgggttgg atcccagcc gttttactgg     22440 tagcaccgga ttccagcgac cctggctatc cgttgacaag agaatggagt gcgcagggat    22500
gaggcgtgca aaaaaaacga gcagcatatt acctcctttg ggagagcagt tatatattta    22560
aaaggatttt ttttcggaat tcacactttg aacctaaaag acctaaaatt tggaagtcca    22620
acaaatagcc atgccaaaag aaaatatcaa aataagtgca aattatactc ataaattact    22680
```

```
caatttttt  tatccagcac  tttggccttt  ggtcatttgc  cgattggcgt  tcgctgcgct   22740
catttcctaa  ttgcttatat  ctcaagcgca  ttttcccact  gatttaatcg  ccaccggaaa   22800
ttttaaattc  cattaaaacc  cccgagacgg  aaaaagggga  aaggataaac  atgcccactc   22860
tgacatgcct  agaataatca  tcaatcatat  tatgttaagg  aatatttcaa  ttttgcgggc   22920
ataatacata  acaattgttt  gtcaagaaat  ttattacatt  taaaaggctt  ttgggccatt   22980
agtcaagaga  aggaccaaaa  tataaagcag  gcaattgcaa  ctttaattga  attccaaaaa   23040
gacaatttca  aaatttccat  tgaaactttt  acaagtctta  tgggcatttc  ctacaatggg   23100
tttttgtcaa  tgtcacatac  gaagattttt  ttttaatta  accaagactt  ggagacacac   23160
ttaggcaatg  tattgaaacg  aagataatca  tttaaagaat  tttatgctt  ctgaacagca   23220 aggcaatgaa  ccaaagttga  gaaattgttt  aataaattgg  aaaaatatcc  cttaatccgc   23280 caatttttt  tctcaaagaa  tgtcaagtca  gaactcaaga  aattttgaac  gaaattagat   23340
gaatcaaagc  ctttgggtaa  attagtcatg  gtaaaatagg  actgcacata  tgatttgcgc   23400
agtagcttaa  ttaatttgtc  aaagatttaa  ctcagggctg  ccatccgtcc  ttgaatggca   23460
aggacgtcct  tgaaatttggg  ccctcttct  tgaaaataaa  aaatgtcctt  ggatgccaag   23520
gacgtccttg  aaaatgaaca  tttagaaaag  ttttaaaaaa  attcaaagaa  atttgagaaa   23580
tctttgtaat  tttcaacgat  attttgatta  tattatggca  ttatgtaaat  aaaatgcaaa   23640
ttttcaaatt  ttctcatgct  tgtgaatgaa  tttgttacgc  aattttcgc  gtttgcgaca   23700 tattatattt  tagaatgttc  ccaaataagc  gcaaatgttc  tttcaatccc  gattgggaaa   23760
agcaatatac  ttttgtcaaa  agaagccgaa  aagggaatgg  attttttat  tgtgcttttt   23820 gccaaaaga  catcaatgtc  gagtcgatgg  gagtttcggc  cataaagtcg  cacacggaaa   23880
acaaagaaca  taagcaaatt  aaagaggaac  ggcgtaaaag  cacaacaatt  gagaattttg   23940
ttcgatccaa  atcgacgctt  aattcaattg  accttcaagt  tgcaacggct  gagggtcatt   24000 tttaatctt  tttaagtgta  aaaattttgtt  tttaggcact  tttgcttacc  atgtgtgtaa   24060
tcatcatcaa  tcgtttgcgt  caactgattg  ttcatcaacg  ttgtataaag  aagttttctc   24120
tgattctgag  attgcgaaac  gatatgggtc  ggcaaagatg  aaaactgcag  caattattaa   24180
aggttttgaa  aaatcaaaaa  tttcattgaa  ttttcaacaa  aggagttctg  agcccgtttt   24240
caatggaact  tctgaaaaat  gagttgggcc  aacaaccatt  ttcactttgc  attgacgcaa   24300
gtaatcatgg  cgaaaaaaaa  ctcgttccga  ttgtgatccg  attttcaat  ggcaaattgg   24360 gactcaggac  ccgaatgttg  gacatgactt  cattgcctgg  agagactgct  gatcaactat   24420
ttgattggat  ttgttcgtcc  atggaaaaac  atcagctgga  ctttaggaat  ttgatcagtt   24480
tttgtgctga  caatgcgccg  acaaattttg  gtgtgccaca  acaattacag  gagggtagga   24540
cggggaacaa  tgttttttgca  aaactcaaaa  caaagaggca  aaatatcatt  ccgattggct   24600
gttccggtta  cttttaaatt  gtttgttctt  cttatttaaa  aatttcatcc  catattttgc   24660
ataatgcagc  aaaaaagggt  gccgaacaat  tgcaatttga  cattgagtcc  gtcgtttaca   24720
aattaacttc  atatttcaaa  ggatcaacgc  aaagacacac  cgaatttcat  gaaatttgtg   24780
accaatatga  ggtgctcaat  tttcaaattt  taaaattaat  tttgtttttaa  agacgacttt   24840 tgtaccattg  ccaactcatg  cacccacacg  ttggactacc  ctatcaaaag  tggtcagccg   24900
gatgttagag  aaatggcacc  aattaaaaga  gcttttttgca  atgccgaaca  agccgcgtgt   24960
tttacatgaa  ttttttcaat  cggaaaattc  tgaaccaatt  tgttactttt  tacaaaatgt   25020
gttgaagacg  tttgatgagc  ccattttggc  attacaagtt  aacaattatt  ttttaaatta   25080
```

```
aggtcacaat gttttacag aaatcaaatt tgatgctgcc ggatttaatc agtattatgg    25140
aacaatttcg tgccaaaatt aaaggtcgtt tgcacggcac tggaaattcg ggaaggccat    25200
tttttggagg acattttgcg ttgcgccgtg catcaacgga acttgaaaaa gattttttgcg   25260 taaaatttt gtattttgt tttattaatg cattttttta aagaattttt acaaaattgt     25320
gctcaaatac attgatcgct ggttccaact ccaattacta ccaaaaaata tttcatggac    25380
aaatttacaa aatcatcctt tgaattatgc agaagttatg caacttgctg agcaatgtcc    25440
cgaaatagcg caattggatg aactgtttga tgaagtgtct gcggtgaacc aaacattggc    25500
cgacattccc gaagaattt ggctcaaatc agccgaagat aaatgaaaag gattttttgt    25560
ggcggatggt gctatagagg gctacaaaaa tttataccga gtcgtcagtg cagcttttc    25620 ggtcattaaa aataaaaaaa agaaatgaat ttttattta aagattccga catccaatgc   25680
attcgtggaa cgagtttttt cactggcaag cagtcaatgg accaagaaaa gaaattcatt   25740
ggaagttgaa tcggtgaaag cgctcttact ggtgaaggtg aactttgatc tctcgtgcgc   25800
ggaaatgagg aaaatgatca gcggaaacaa aaaaatattg gaaaaaatcc attccggtga   25860
aaaatacaaa ccatttgaat aaattttaac cattttttcat tgcatataat aaaaatttta  25920
aatgtccttg gatttcatga attttcccca ctatgtcctt gaaaatcggc atcccgtcc    25980 ttggaaacgg aggatggacg atgggagccc tgcaaaagaa ttaaataatt tatgaccaaa   26040
agcgacgaaa caatggccag atatgctaga aattaaaaag tatatgaaat tttttgaatt   26100
tcttccttta aaattttta ttaataaatt ttccttttta tattttaatt tttcatttt     26160 attttaaaaa aataaatagga ctctcgagaa cgaaatttaa attcgttttt gtttattagg   26220
taaacaaatt atgccccatt aaattcattt taatctcatg acaaacaaat ttaactaaaa   26280
attacttaaa attgcataat tataaagtaa taaatcatta ttattttat cttattctta    26340 ctaattaata ttcgcgtgag ctgctaagga attgacaaat aaggaacaca ttttctgttt   26400
cctggcatat tatgttaagc gaattataca aattagcaca tccattaatt agcgtgccca   26460
gcgaggacat ttttctcatc tataatacat tgttaatgag ctaaattaat agaatttggc   26520
aaaaactcgg gactcactca taaaacactt tcaagaccac taattgacaa caattaacgg   26580
ttcttcttat ttatttcaac aaataaataa ttaaaaagtc aaaaaaaatt tcaatataat   26640
tatcgtcaca ttttgtcatg acttttaatt ggcatgatgag tagacagatg agttaattat   26700
ctcttcggtc tgtgccaata gattattatg tttgtgccga cgttttttga tgccgaattg   26760
tacccaataa ttactctttc ttttttttat actaattttc acttttcctt cgaacctgaa   26820 aagcttttt atcatttcta ataatttc taaaatgtct tcaattgcca tgataatctt      26880
cttctcatta tttgttcttt atgcaacgga ttcaatcgct tcagctgctg cgacaatggc   26940
tgatgatcat cttccacagc ggagagctgc tgacgccgaa ttggcggtag aggaggatac   27000
tgtaagagca ccaccaattc aattaattag gactaatagt ttgttaatga aagacgtga    27060 tgcacaaggg ttaggtgttt agttaagcga acgacaatat aatggtaaaa ctaaacaagc   27120
atgagttgga aggagattgc caggaccaaa attaattagg actaattaat tagctaataa   27180
gaagaggtga tgcaaaaggg ttaggtggtt gttcaagcga attacaatat gctggtaaaa   27240
ttaaactggc ccgtaagtca ttcgtgttgg tttctttggc actgaagtgt ccattttcac   27300
tgggactcat ttgtcccagt gctcagatgg cattggttcg actttagact ttgatcgtca   27360
aaatctttta aatgatacca aatttgttcg gttttggttt atttaaagag taataaaagc   27420
```

```
caaatttgct ccattttcga gttttaacc agttcaaaaa ccgatttttt ggcatttccg   27480
caactgctgg agacctaatt ttcgtgcata gctcatcgag acgaatcgaa tggcatatca   27540
tttgtgccgt ttttctggaa cgttcgggcg ttcactttat ttcacccaga cagaatattg   27600
ttaaaatgat tctttttgct tttaattggt tttgcgaaag gattcatttt tttcgtctcc   27660
ttttcatata atcccttgag gggattaaca aaagttgaca tgtatttatg atgtcattat   27720
atatgattta aaacttagcg gaagtttatc tttaagacaa ttgaactcaa ttagtaaaat   27780
aagctgagaa tgacgtcatt taagaaaggg aaaacaaaaa ttgattaaaa aaaatcaaaa   27840
ctaattaatt tatgaatatt ttaatttgtt attcatttaa tttgcactttt tatataggca   27900 cagaacgaaa atttgttcgg cgcttatttg tctcgggaa tgttcagctg cgccgccaaa   27960
tatgttggca cattgcaaag actgaaaaga atcattgagg taaaaggag gcggaaatga   28020 cagaaatttg aaaacaaaat gccaaataaa tttaaatat ttaaatata atttaaaatg   28080 ttattgaata taaaggaagt gcatgccgac tattcggaat gccaaaaatc gatgaagcaa   28140
atggacgagg acgagcaaat ggcattcgga aaagggcacg gcacagagcg atttgcgatg   28200
attgacgaac tgatcaattg agcccagggg ggcaatttgt ggcaaaatca caaaattcga   28260
agcataacca tttgaaaaac attgaaatga ttttcatttt tgtgataaag tgaaacagca   28320
atttgttaat aaaatgccaa aatttgtgcc aatttattcg ccgtccaaca aaattaatt   28380 aatttttttc acaattcgtc cccataattc gttttgtttt tgttttgttc gtcgcttttt   28440 ctttttctc catcatttttg ccctcatcag aaaatgcatc tgcgcacttc gcctgcttcg   28500
gtttggcttt gagaaaatgc tcaaacactt tttgaaggtt ggcgtggaaa agcaatcgga   28560
cctaaaaatg aaaaggaatt aaaaaattaa tttaatatta aatttaattt taaaaatatc   28620 tgcaataag caaggttct cgaacctgca caggtatctt tgtttggat gaatgtggga   28680 gaagaatccg tgacaagttt ctgaataaaa aataaattaa aataatgcaa attttggatt   28740
taaaaacgaa aaaaactgac cgcataattg gtccacgaaa gctgaataat taagcaaaat   28800
tattttcaaa taatgaatca atttattttt tatttagtcc gcttttcatc cagtttgatc   28860
cattgtccat ttttgtgact ttcaatagtc catatttttt agccttctt catagtcaat   28920 ttggccttat tggacaaata ttccattttt ttgccatttt gtcactcatt tttttccgtt   28980
gtccaaatgt ccctcttttg gtcattatgt ccccactttt atctcgaatt tgtccatttt   29040
ctcaccttgc agagctcttc gtttgacaat caatttgcac tgttttact cttttgttcc   29100 gtatttttt tcattttgtg tcatgtcccc cttttctctc tcgcttttgc ccattttctc   29160
accatgtaac tcttcgttgg cgtgaaattg gcactgtatt tgttgtccac ttctgctgc   29220 cccgtcgtct tcctcctcta ttggcacgtg ccgtcctctt cctcctcctg ccccattttc   29280
gtcatcgtca acgtcggccg gtgccatttc ttccgcctca cttttttgtt gttttgtcg   29340 ctgtaaaacc attgcaattg ttggccctcg tctcattatt ttgctgctgg caaatcgttc   29400
attttcatcc gccaaagtgc gcacgacgga cggcaaaatg aggaggaaaa gcgaactgag   29460
ggggagaagc gggggaaatt aattaaattt agaatagaaa tagaaattaa atttaaaaaa   29520
tgactaaccc aaaaaagaat gcattaatgt gagcggaata ttggcgcatt tcagcagaat   29580
gaatgcccaa atttgtgaac gcggcaaatg ctcgtaaaat ttggcggcga atggcaaatg   29640
aatggcgcgg gaagggacaa atgactgaat gaaaatgaga gtgacaaaag caaacaatc   29700 gctggcggcg ttctgaaaag caattaatta aatagataaa tgggtggtgg tggtggtggc   29760
aattctcgcg ttggcactta atttattcgc caattgggca aaaaaagggc aggtgaaatt   29820
```

```
tgatcaaacg gggacaaat gggacggaag tgggcgaagg agtgcgtcaa aaatgacaaa    29880
ttgacaggcg aatgatttga ttaatatgcc atcggaaagc aaattaaatt ggggcactaa    29940
atttaacaaa tcaaaaaagg gagtgccaat gaaatgaaa tggaaaaagg aaattaggaa     30000
aaagagaaaa agcggaagaa aatggcactt taaatgggt gatcagcagc agaggattaa     30060
ttgaataaaa taaaccaatg tgttgctctg tttcttaatt gggagcaacg aaatgactaa    30120
attgctaagt aaaaatcatt ttaagtaatt gcatttaatt tttaatcttt tcctgctccg    30180 aattttttt tacaaattcc ggtccctaag ataattaatt ggtcatttat agaattagta     30240
gttggttaat gagataaaat gctttggttt aaattttgac agtcacaatt cgccaaagga    30300
aatgactaat taccgaagga aattggttct ttcatttgtt taaattatgt ttactttttt    30360
acttttgtta agtctgtttt ttgttttcca ttgctttata aaaattttt ggaaatcttt     30420 cgctccattt catttttctt tgtttggctt tgtgcttttt ctttctcttt gttttggat    30480 ttgaatttgt ttaaataatt tatcagatga tgtcaaaaat tcctctaacc aatatttgtt    30540
ccggcgaatg cttcgccatt aaacgaaaaa aatgcaattt atttgtcatt aaatttggtc    30600
cgaatttctg tgagcacgtt ttcatgtaaa atgacaccat aacgaagcaa atttattggc    30660
atttttgggg gtttaaagaa aaaaggata aaattggcaa aatgagcgaa ctacataaat     30720 gacgttaca attaaattt gaatattt cactttttat ttttatttt gcttttttgt         30780 ttcctctatt aattcgccag cagctgaatt atgacaaatg atgacttcat aattctaagc    30840
taatgatgag tgaattgtgg aaacggatgt gctgttaaat gatgtattca gacggaaagc    30900
caatggaatg acaaatggca aatgccaaaa tgaaacagac attaaaactg aacacaaaaa    30960
agccctaaag tgccaatgtt tttgtagcaa agtcaagact ctcgagtgca gattagtggt    31020
ggaaggacta tcatttaaaa ggggaggagc actttttatt ttaggctaat gatgatgagg    31080
taatgaatgg tcgcgtggca cccaatgaaa tgaatggtcg tccgcctttt tgagaaaacg    31140
gcgatttgtg ccgtgttggc ccagtgccaa attcagtttc gaaagtgggg acaatggaga    31200
gggggggggg agggattgg accacccatc ctcgattcag tgttttgccc ccgtcttctc     31260
ccgattgtta attgcttctc tctgctgcaa cttttgctga attttccggc atttaaccga    31320
gactctcgac actgtccatt tgtttatttt tggcacttga cttggcattt tttatattgt    31380
cggggcgggg caattggaat tcaaagatga cgcggtgaag gagggcgaac atgacaaatt    31440
ttactacatt gaaatgcat taatcaaatc aaaattcttt ttcagagaag aatccaaaaa     31500
caaatgttct gatctttatt cttagcataa aagcaaagcg aatttattta tgattaaatt    31560
tcaaaaaaaa atatgaattt atttggcaaa gataatccaa atccataaac aaaattaaat    31620
atttagaatc ctaatgattt catcagtgaa agattaatag caatttgagc attttgttag    31680
gcaaacattt tagcgaagaa taaatgtcat ggcataatct aagactattt ggcaatttgg    31740
aaccacgtaa aaaattatta aattaagaaa accatacaat tataaaacca ttaaatttgg    31800
tccctgctaa tgttaattgc ttcctccgct ttttgtgccc cttttccagc attttcgct     31860 tctctaattg atggggggg gttcactttt ggcatttttt gtgtgttatt tttgtgccgg    31920
aaaacattta aattgtcata tgcgcaaatt tgccgaaatt cagaatgatg gaatgaatgg    31980
cgtgggaagt gccagagagg caatttccat ttttgtcaat tgaagtcgag cggccggagt    32040
aaacaaaaaa aagaattgcc ggggggggaga acgcatgaat aaaataaagt tgtgacattt   32100
aacttaatta agttatgcta ttttagaatg gcaaaacgtg tgaaaatttt tgttttcttt    32160
```

```
gttattaaat aaatttatta aaaaaaaccg ccaaatatgg caaattataa caatgactga    32220
tcataagggc tgtgattttt aggcacaaaa atagcgaaat aggcaaaaaa acataagaaa    32280
accaccctaa aatagacagg aaataagcat aaaatattca ataaccaat tcaactcgaa     32340 aactaggcaa ttttttgaa tttagagcaa actgtactta aaattaacca atttttctgt    32400
tctgttatga tggcttgtat tcgaaaaaaa atatttaaaa attttttcaga aaaattaaac   32460 ttatgggggt tgggttttta aaagtctttt ttttgggagt tgcatttttta agcgatgcgc   32520 tcaaattttg tcattttccc ttaaaatcac agcgcaactg atcattttg aactaatgcg     32580 ccgccgccac tttcttttgt ttctgcaaaa tgccgagcag ccgattgacg tgacgcatct    32640
gaagccgtcc ccggaagcga tcggtgcgtc gtttctgcca aatcaaagca aagcaattag    32700
cgttaattag ctacaaataa aatcattctt ctgtcttgcc ttgtgtcgga tgatcattgc    32760
tctgcgctga tcactggtgc tcaattgtcc ccgttgctgt tccccgtcaa ttgtcagcag    32820
ttccctcttg ccaattttgg tcccaatttg ttgccgcttt tcctcctcct cctccgattg    32880
ctccaacttt tcgtcgccgt ttgacttac catgacatca tcattttat tatgcgatgc      32940 tttggcctcg ctactgctcg gcacgctcaa aatgactaaa acaaaggaaa atttacaaaa    33000
aaaaattggc ataaatgaga taccgcactt atgaattaga gccccgggg gttccaaatt     33060 tcaaccccc tccaaaggtg actttattt caggggctgg ggttcaaatt aagtggagtt      33120
ctgtttcagt aatacggtat atttgtgaga attcaaaaca aatccctttt ctgcttgcta    33180
gtgattaccg ttgcccgttt cttccccgt aattggcgcc gccggctgct gcaccgatcc     33240
gtttgattcg gggacaaacg atggcactcg gatttgtgtc cctctccggc ctccgtccgc    33300
tgcattttct cctcctccaa aaggtgttgt ccccaaatgc tgtactcggt caacatgctt    33360
attaagctga tgctgaagat gaaccatatg ctcactgcca ctcccgtcct gttcattccg    33420
ctgatcggcc cttttttcctt ttccaaatgt tggcattttg aagatgggac tccgttcagc   33480
cgcatttcca tgcttcagtt ggtgatgttg tgccaactct gctacttcag tgcgttgatc    33540
attttcattc ttctgatcag cgtcggcact gttttcgatc gcatttgcct ttggcattag    33600
tgggccagcc aaatggctgc cgataatgtt ggacagcgat gccattgcat ctgggattcc    33660
gttgcattcc gcgcacagac cgcggctccg ctgtgctgct ggcggtgccg cgacattgta    33720
atgctcgtca attgttacac tagttggcac cgttaattga gcaaaattct gtattaaaat    33780
gaaaattttt tactgtgaaa ccttttgaaga aattggcatc gcgacgggtg aaggggggagg  33840 aaagtgtggc atatcggcag aagtgaacga tggcattggc atttggtgct gctggtaacg    33900
gattgaggcg cgtcccacgg gctcatggag gacgggctgc ggcacattca aaaacattgg    33960
caaagtgtcg acgaccactg aaaagaaagg cacggcaaaa agtgccatta aaagtagta     34020 aaataatttt gagaatttaa atagactttc aaattataat tatttaaacc attttttctca   34080 tttggcatttt ttggctcctc attttgctcc tccccttcaa aattgcctga tgatttccaa   34140
tagggtcgat cataccttaa ttaatttgag aattaatctt tatttataa ttttccaatt     34200 accatagtct tcgaaatcgc tctctgactt ctgcgtccac aattggcact ccgacgaaaa    34260
acaaacggtc caaacgcta aatggcaatt cggccattac actctcaacg gtggccaact     34320
tttgctagaa aaattttta tttttaaata ttttaatcag ggcgtagcca aaggggggg      34380 gctctattca aaaattcaat ttttagggat gtatttttct ttttggggggg tggctttagc   34440 ccgcttagcc ccccccctgg ctacgctctt gattttttaaa ttgaattgtt gttaattgcg   34500
cgcatcaatg ttcagcgtgt tcgatgccaa tgccgagtaa atttggacag ccaacggatg    34560
```

```
gggaagtatg tcgcaaagct ctttgatttg ctaaaattgc attacaacac ccacaatttc   34620
tgcgtgtttt tggcaaaatg ccattcgctt cgtacaaagg tgaagctgac gctgtacttc   34680
agggcactga cactttcgaa cagtcgcgag tggcccgtgc cggcgagggt cggctgggca   34740
aatgccgacg acgcatcggc gaccgcggcg gatggcattt gttggatggg cgcaaagcgc   34800
cgcttttggg gcgggactga ttgggtcagc gcgaaaatgg cctcatgttt ttggcgccag   34860
ctgagcgttt tgtcaaaaag caggtctttg atctgccaac gaactgaaat tgttgggaaa   34920
ttaatattaa ttttaatcaa aaataaaatt caaaaatttc caaatttaaa tatttaaatt   34980
aattttattt caaagaattc tcattttatt atattaatat tattattttt tattgattct   35040
aatgaaaatt aaatgatttt gcttaaatat ttaattaatt gttcggttat ttaattttat   35100
aaaaacgcaa attttagtc tttccgccag aatttcttgt cgaaccccga acccgggttc   35160
gagcaaaaag ttgaaaattc aattttgaat ttcgtatata gagaaacaaa ctaaaagaca   35220
atcccctaat aaaagatcat ttaatcattt ttagagtaac aatgagaaat tcgaaaatta   35280
aatttcgact ttttgctcga atccggattg gattgggttc aaatgaaaca aatatctgac   35340 ctccttttt gaattaaatt ttttgcatat cgaacggctt tttttctct tttttaaatt   35400 ggtgtgcggc atcaaaacgg aaaagaaact aacaaataag caatatttaa tatagaaata   35460
tttaaaattg aattataaat catatttat aaaatttcaa ttaattgttt cactgctgaa   35520
tggcagtcgg gagtagaatc tcggcaattc caatcggtcg agaaccgatc ggggcacctc   35580
cttcagcagc tgatcagtga gccttttccac ctccattttg tccaattccg aatcggattc   35640
gagcgcaaat attttctcca tcaaatcgcg tggcaataaa aaatccttt ttaaaaaatt   35700 aaaattattt aatgccatt tatattggca caaaaaaaac aattacccat ttcctctgca   35760
caaaagaaaa ggccactaat tgatcaattg caattaaaag gaaaaggaca aattttaatg   35820
gacaaaacaa agacattttg ggggcgaact gttttaatga caaaatgacc aatttttgtc   35880
tcggtattta agcattttgg tggacaagca gctcatttaa tgggtacatc gttggccaat   35940
tgatgagaaa tggccaaaaa atatggcagt tgcatctgcg caaataaaat tgatggcgct   36000
ccaaccacaa aatcattccg tcttcatttt gtacagaatt ttatttttgg acaagaaaaa   36060
attgcttgtg attttcacaa aaatgaataa atgacccaga gaagcttttt cattttttgt   36120
tggcagtgaa tttaattgaa caaaaatatg taaataatta attaattaat ggacgcatta   36180
ataaattgtg ctcaaagcct ttttaagaaa aataaaaatc acacaatttt tggtacttgt   36240
cccttttgat gtttgtaact cacaattcgg acaattttg gcattttta aaggttcaaa   36300 gccatttttt gtgagtttta aggcatattt tagtgcatat ttagacactt tccgaatttt   36360
taggcatttt tgagggattt ttagtgcata gttggcattt tttaaatgca ttcaacttat   36420
aatcctgcct gataaccttg tatgatgaaa agcacctata aaatcttggt gttttatatt   36480
tttcacttca gattcttgat tagcgcctaa aaagtgcacc agaaaatagt tatttattta   36540 ttttttttctg ggtcataaaa tttagagggg tttgcgacag acataacgta aaagtatcaa   36600
aatttcaacc aattaaatat aataaattga aaaaatttg aaataataaa attattattt   36660
aaactagcgc ataaaaaact aacaaaaaaa aaagtgaaa tgcatccaaa ctttagcatc   36720 tgttttttgtt tttattcttt agcatgctct gcaaatttct tgcaaaaagg cgaggagcaa   36780
aagcaccaaa atgaccatgc cgaaaatgac caatggggcg aaacgccttc tgcgccgctg   36840 ttgcttttc agcttctctt aacaaatgat aataataata ataatagtga aacgtggggg   36900
```

-continued

```
gcccttccca ggatcgctgt agtccaaata ttatccagaa atcctttatt gttccatctc    36960
aaacttgggt aattaaacct tgcttgtga aatgtgaaat gaatggaaaa tacaaatgac    37020
ggatcgaaat ggggaaggat ggaactgatc gaaatgggaa aggatggaga aatgatgaaa    37080
tgaaatgata aaatgctcgg gaaatctcgg aaaaggattt agcggagaag agaccagaga    37140
ccaaacgggg aagtgatcgg aaatccactt tacacctcca tcccttgagg cgatcgtccc    37200
cgatcgtttc caaaatttag gtaatttcca aaatataatt cgtaaaattc tcgcgagatt    37260
tcatgaagaa agaaatagag aaatgagagg gcgaattaat tggtaaataa aattgtaaga    37320
aaacgaaaaa tgaaatcagg tgcgacatcg ttttgaaaag tgtccgattt ttccgcatct    37380
atagcacttc acatcgattc ttcggttgct gttcgagttt gacggggctt gttgggcggc    37440
ttcggcgtat gacggcaaat attgtggcgg atacggcgcc attcgcgtac ttggaccagg    37500
gcaatttgaa ggcattggca ttgtgtgacc agcgatcatg ttgattggag gagggcgcac    37560
agaggtgtca atgatcatca ttccgtgtga gaaagccggc ggttgagcat gacccgaact    37620
gatcggtgga aacacatttg cctgagctgt gagtggcctg aaaccacctg tgaaaaatgg    37680
ggaaggggaa aaattattta cgaaattatt tattggtggc tgatacgcca aactatcgtg    37740
tcttaaagta ctgtcccttt cggcataaaa ttcaaatgcc atcggaactg tgccatccct    37800
ttttgcaata aattttccca cccgggacgg aaacggattg gaaataaggt ttaaatactc    37860
cggggttacc gcaaccgtca tttttaatgt ttcgtcaatg aaacgtctcc acacggtccc    37920
tttgtgccaa atcaacgaca aatctccgat gatgaccaat ccaaatttgg gacgggagag    37980
agccacggtt gttctcgcgc aatccgccca gaattccttg ccagtgtcag cttccgatga    38040
tcgtccagcc gcggagcgag tcgtgatgac aaggacaagc tcggcttcct gactttgaat    38100
cgaattgact gtactcacct tgacatttgg ccaccttctc cgttcgattt cacttaccat    38160
gtgtttcctc tctgcttggt aaaaacacac aacttgaatt aagcctggaa aggttccctg    38220
gattattccc aaaaatccaa gagctgtttc ccgttgctcg ggattgtgag aggaaaatga    38280
gatactttcc atttgagccg atgatttttg atggattaaa atgatcggac aattttcggc    38340
tacaatgcgt gggcccatat aattaaacga tgacatttct acgtccggcc ttcctggtac    38400
caaccgatca cctgctggag agtaaactcc cgcgtccaaa caccgtacaa tggcactgtg    38460
cgatcggtaa cactttgaga gaacggtgcg atcgatgcct tttgctgttt ccagcacttc    38520
caaaattgac tcaaacccaa acttaccacg aataactgtc atttgactcg gtaagtgtac    38580
ccgtaactgc tgtttatctc ctgtcagaag tattttcttt accgatcgga attgtgtgag    38640
aattgacaaa actgccgaaa gcgtggcttg cccacactca tcaaccaaca cataagttac    38700
gttgcccaaa tccaatgcca actcctcagc aagagccaat gtcatgaagt acactcggta    38760
tttgatttgt ttcagaagcg cggcagtcgt cgttcgttcg cgtgcccgtc ttggtgctgt    38820
gttaaagtca tcgacgtatt gcttaaatgt tttattatca ctccattttt tcggctcggt    38880
tccttcagcg gagggaacat ttccatccct ttgcacagct tcaactaaaa gattgtcccc    38940
caggggcctg atcctgtcca tgtaacgccc ttttccttgc ccagagaaaa gtgccaacat    39000
tggcaccttt tctgacaaac tttccatggt gtccttcacc aactcacaca ctgcgacatt    39060
caaaggagaa actgccaaaa ttgcagcgtc acggtccttt ttgagcacgc ttgcgatgca    39120
ggccgctact gacacacttt ttcccgttcc tgccggtgcc tgcatgaaaa ttacacggga    39180
ctcgtcgtcc aaaaacaatc cgtgagtgat tcgctggtcc tcgttcaact taccgaccgc    39240
aatttcggta cttgacaacc taacggttgg tcgttgttcc gctccgtctt tgcccattcc    39300
```

-continued

```
catcaatatc tttaaaattt ttgagacggg atatttttcct tctgcaatat ccgacgggac   39360
tgaaagttca aatgcctgtt ctctgaaagg gagacctccg taattaggaa ttggaatcac   39420
attagattcc ctttcatcaa gaatggattc ccaatcttcc catccctgt cgtagccctt    39480 tttagccctg taactcaaaa acattttcac gttcatcaga aagttacccg gagcggtttc   39540
atttactgac agttcaatta ctcggccaac tgcacagcat gggcttttg agtcacgcgc    39600 aactttttgct tcgaccggcg tgtcctcctc ccatgcctct cgatgaaatt ggttgatcag  39660
gtggcagacc gtctcgtaca ttcatccttt gaattagttg atcagctaag gcacttaaat   39720
caacagtcac gttttgagga ttggaagatg tctgaggtac gacatcatta gcttggaatg   39780
gataattagg ctgtaccatg ttaaccgggg tgtaataggt aggtctattt gagttgttat   39840
tgggaccatt catttgaaat tgtgagcgcc tgtccctaca gttgtacgca acatgtccca   39900
atctaccgca gtgatggcat tttggacggc cagtccaatt gcggtcccct cggcctcggt   39960
tcgaccggta ttgattagcc ctatttcttt gaaattgagg cctgttggat tcaccgtggt   40020
taccccgaaa atagcctctt cctgaaccat ttggttgatt attttgtgct tgctgattaa   40080
cctgacggtt attcgtatat cttttgtacag cgggtgccca tgaattcaca ttggaggaag  40140
aaaattggtt agtacgataa cccgattggt ttaccggaga ttgggttata gcttggacag   40200
tgaatttgag cgggtccaaa acgttatttt cattggtatt agtcaaaaga agttctaat    40259
```

<210> SEQ ID NO 44
<211> LENGTH: 1017
<212> TYPE: DNA
<213> ORGANISM: Heterodera glycines
<220> FEATURE:
<221> NAME/KEY: CDS
<222> LOCATION: (1)..(1017)
<223> OTHER INFORMATION: G in TN10, A in TN20
<220> FEATURE:
<221> NAME/KEY: variation
<222> LOCATION: (70)..(70)
<223> OTHER INFORMATION: C in TN10, G in TN20
<220> FEATURE:
<221> NAME/KEY: variation
<222> LOCATION: (131)..(131)
<223> OTHER INFORMATION: G in TN10, A in TN20

<400> SEQUENCE: 44

```
atg cca ccc cca att ggc tca att att tcc aaa tgg act ttc tct gag         48
Met Pro Pro Pro Ile Gly Ser Ile Ile Ser Lys Trp Thr Phe Ser Glu
1               5                   10                  15 gcc ctt tcg gtg ttt tca ctc sct ttc ccc gaa ctc att ttt cgt gcc        96
Ala Leu Ser Val Phe Ser Leu Xaa Phe Pro Glu Leu Ile Phe Arg Ala
            20                  25                  30 caa aat gtc cat cag cag cat cac aat cca agc cra gtt caa atc agt      144
Gln Asn Val His Gln Gln His His Asn Pro Ser Xaa Val Gln Ile Ser
        35                  40                  45 acg ttg ttg agc ata aaa acg ggc gcg tgt ccg gag aac tgt tcg tac      192
Thr Leu Leu Ser Ile Lys Thr Gly Ala Cys Pro Glu Asn Cys Ser Tyr
    50                  55                  60 tgt ccg cag tcg ggc tac cat aag acg ggg ctg aag aag gag ccg ttg      240
Cys Pro Gln Ser Gly Tyr His Lys Thr Gly Leu Lys Lys Glu Pro Leu
65                  70                  75                  80 atg gaa gtg gaa cag gtg ttg gaa gcc gct aaa aga gca aag gcc agc      288
Met Glu Val Glu Gln Val Leu Glu Ala Ala Lys Arg Ala Lys Ala Ser
                85                  90                  95 ggc gcg aca cga ttt tgt atg ggg gcg gca tgg agg ggc ccg aag gac      336
Gly Ala Thr Arg Phe Cys Met Gly Ala Ala Trp Arg Gly Pro Lys Asp
```

```
cgc gac ttg gac aaa gtg tgc gaa atg gtg gcc aaa gtc aaa caa ttg      384
Arg Asp Leu Asp Lys Val Cys Glu Met Val Ala Lys Val Lys Gln Leu
        115                 120                 125 ggt ggc ctt gaa aca tgc gcg act ttg gga ctg ctc aaa aac gag gga      432
Gly Gly Leu Glu Thr Cys Ala Thr Leu Gly Leu Leu Lys Asn Glu Gly
130                 135                 140 cag gcg caa aga ctg aag aaa gcg gga ttg gac ttt tac aac cac aac      480
Gln Ala Gln Arg Leu Lys Lys Ala Gly Leu Asp Phe Tyr Asn His Asn
145                 150                 155                 160 atc gac tgc tcc aag gac ttt tac cac aaa atc att aca acg cgc cgc      528
Ile Asp Cys Ser Lys Asp Phe Tyr His Lys Ile Ile Thr Thr Arg Arg
                165                 170                 175 ttt gat gac cga att tcg acc att gag aaa gtt cgt tcg gcc ggc atc      576
Phe Asp Asp Arg Ile Ser Thr Ile Glu Lys Val Arg Ser Ala Gly Ile
            180                 185                 190 aaa gtt tgc tgc gga gga att atc gga atg gga gag aat aac gaa gaa      624
Lys Val Cys Cys Gly Gly Ile Ile Gly Met Gly Glu Asn Asn Glu Glu
        195                 200                 205 cgg gtg aaa atg ctc gtc aca ttg gcc aat ttc gca cct ccg ccc gaa      672
Arg Val Lys Met Leu Val Thr Leu Ala Asn Phe Ala Pro Pro Pro Glu
210                 215                 220 tcg gtg cca att aac aaa tta atg ccc ttc ccc ggc act ccg ttg gcc      720
Ser Val Pro Ile Asn Lys Leu Met Pro Phe Pro Gly Thr Pro Leu Ala
225                 230                 235                 240 aat gcc ccg gcg ccc gac ccc ttc gat ttc gtg cgc aca att gcc acg      768
Asn Ala Pro Ala Pro Asp Pro Phe Asp Phe Val Arg Thr Ile Ala Thr
                245                 250                 255 gcg cgt gtt ctg atg cca atg gct tac atc cga ctg tcg gct ggc aga      816
Ala Arg Val Leu Met Pro Met Ala Tyr Ile Arg Leu Ser Ala Gly Arg
            260                 265                 270 gag caa atg gcg gac gaa ttg cag gca ctt tgt ttt tta gcc ggt gcg      864
Glu Gln Met Ala Asp Glu Leu Gln Ala Leu Cys Phe Leu Ala Gly Ala
        275                 280                 285 aat tca ctt ttc ttt ggg gaa aag tta cta acg gcg tca aat cca atg      912
Asn Ser Leu Phe Phe Gly Glu Lys Leu Leu Thr Ala Ser Asn Pro Met
290                 295                 300 cca gaa aaa gac aaa gaa tta ttt caa cga ttg ggt ctc aaa aga gag      960
Pro Glu Lys Asp Lys Glu Leu Phe Gln Arg Leu Gly Leu Lys Arg Glu
305                 310                 315                 320 caa att gag gag aaa aaa gct gaa cgg aat gac gaa aaa gtg acc ttg      1008
Gln Ile Glu Glu Lys Lys Ala Glu Arg Asn Asp Glu Lys Val Thr Leu
                325                 330                 335 aac ttg tga                                                          1017
Asn Leu <210> SEQ ID NO 45
<211> LENGTH: 338
<212> TYPE: PRT
<213> ORGANISM: Heterodera glycines
<220> FEATURE:
<221> NAME/KEY: misc_feature
<222> LOCATION: (24)..(24)
<223> OTHER INFORMATION: The 'Xaa' at location 24 stands for Ala, or
      Pro.
<220> FEATURE:
<221> NAME/KEY: misc_feature
<222> LOCATION: (44)..(44)
<223> OTHER INFORMATION: The 'Xaa' at location 44 stands for Arg, or
      Gln.

<400> SEQUENCE: 45
```

```
Met Pro Pro Pro Ile Gly Ser Ile Ile Ser Lys Trp Thr Phe Ser Glu
1               5                   10                  15

Ala Leu Ser Val Phe Ser Leu Xaa Phe Pro Glu Leu Ile Phe Arg Ala
            20                  25                  30

Gln Asn Val His Gln Gln His His Asn Pro Ser Xaa Val Gln Ile Ser
        35                  40                  45

Thr Leu Leu Ser Ile Lys Thr Gly Ala Cys Pro Glu Asn Cys Ser Tyr
    50                  55                  60

Cys Pro Gln Ser Gly Tyr His Lys Thr Gly Leu Lys Lys Glu Pro Leu
65                  70                  75                  80

Met Glu Val Glu Gln Val Leu Glu Ala Ala Lys Arg Ala Lys Ala Ser
                85                  90                  95

Gly Ala Thr Arg Phe Cys Met Gly Ala Ala Trp Arg Gly Pro Lys Asp
            100                 105                 110

Arg Asp Leu Asp Lys Val Cys Glu Met Val Ala Lys Val Lys Gln Leu
            115                 120                 125

Gly Gly Leu Glu Thr Cys Ala Thr Leu Gly Leu Leu Lys Asn Glu Gly
        130                 135                 140

Gln Ala Gln Arg Leu Lys Lys Ala Gly Leu Asp Phe Tyr Asn His Asn
145                 150                 155                 160

Ile Asp Cys Ser Lys Asp Phe Tyr His Lys Ile Ile Thr Thr Arg Arg
                165                 170                 175

Phe Asp Asp Arg Ile Ser Thr Ile Glu Lys Val Arg Ser Ala Gly Ile
            180                 185                 190

Lys Val Cys Cys Gly Gly Ile Ile Gly Met Gly Glu Asn Asn Glu Glu
        195                 200                 205

Arg Val Lys Met Leu Val Thr Leu Ala Asn Phe Ala Pro Pro Pro Glu
210                 215                 220

Ser Val Pro Ile Asn Lys Leu Met Pro Phe Pro Gly Thr Pro Leu Ala
225                 230                 235                 240

Asn Ala Pro Ala Pro Asp Pro Phe Asp Phe Val Arg Thr Ile Ala Thr
            245                 250                 255

Ala Arg Val Leu Met Pro Met Ala Tyr Ile Arg Leu Ser Ala Gly Arg
            260                 265                 270

Glu Gln Met Ala Asp Glu Leu Gln Ala Leu Cys Phe Leu Ala Gly Ala
            275                 280                 285

Asn Ser Leu Phe Phe Gly Glu Lys Leu Leu Thr Ala Ser Asn Pro Met
        290                 295                 300

Pro Glu Lys Asp Lys Gly Leu Phe Gln Arg Leu Gly Leu Lys Arg Glu
305                 310                 315                 320

Gln Ile Glu Glu Lys Lys Ala Glu Arg Asn Asp Glu Lys Val Thr Leu
                325                 330                 335

Asn Leu

<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 46
taggccctgc catatttg                                                  18

<210> SEQ ID NO 47
```

<211> LENGTH: 18
<212> TYPE: DNA
<213> ORGANISM: artificial sequence
<220> FEATURE:
<223> OTHER INFORMATION: Synthetic oligonucleotide

<400> SEQUENCE: 47
tcctgtgtgt ttcaagtg                                                   18

<210> SEQ ID NO 48
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 48
caaggaatgg gctcaa                                                     16

<210> SEQ ID NO 49
<211> LENGTH: 1245
<212> TYPE: DNA
<213> ORGANISM: Heterodera glycines

<400> SEQUENCE: 49
atgaaaggct tcttcgccct gttcgtcttc gccttcaccc tttcggtgct ttctgccgcc      60
catttgccgc ctttggacat taaccaaatc ccggccgaat accgcggtaa gcgcaagaga     120
aaaaacaatt tggcggggcg attaataata atgataatta gcgataatga cgccgttaac     180
gtgcccctct cagaattgat ccccgaggag gtgaccaaat tctaccacga gctgaccgag     240
gatgacaaaa aggcgctgaa ggaagtggca gaacgccacg aggaattcca aacggaagag     300
caggcaaata aatggacacc cccctaatta attaggtgaa atgacgccta attgcccacc     360
ccttttaagg caatggaagc gctgaaggaa aagagtgaga agctgtacaa caaagcggta     420
atttaaagtt ggatggacaa gtgggggggg ggaggatttc tctgattttg aaattcgctt     480
gggaatgaaa atgggggggg gtgacggaat gatcttccca acaaaataat tggaaaaagg     540
aaacagggac cgatcattgg tgatcagtgg cccagaaaaa ggaaggggtg gcggatttta     600
aaataaaatg gttgttctac ccgcacaatt taaggtcgaa ctgcgcaccc ttgtcaaggt     660
cagccacacc aacaactcag cttttgacta gcgaaaggac aaaaataaat tcccaaaaac     720
ttacagggaa aaattgacca attggtgccc gacgcgaagg cattcgttat cggggtaagc     780
aatgggcagc ggaactgatc agacagaagc cgctatttgg tcacagaatc ggaaacatt t     840
aacgctttgc tttcagatga tcgaaaaggc aaagggaatg cgcccgaagg ccggcgagaa     900
gccgaagctt gaggagctgc gcacggcggc caacgagctg atcgagaagt gagtggggaa     960
gggaaggacg gaaatgacaa ttagcggtgc ctttgaccgg tggacaaaat gccgcttttc    1020
cctcccaggt acaaagcatt gaatgacgaa gccaaagagt cgctgaagtc caacttcccc    1080
aagattacga gcgtcatcca aagtcagttg tgtcaattaa attttcaaag tgcatgggct    1140
aatcactttt aattactttc ccatataact ttccctaacg tttcagacga gaaattccaa    1200
accttggcca agagtttgct gaaacaggag gcaccggccg cctaa                    1245

<210> SEQ ID NO 50
<211> LENGTH: 561
<212> TYPE: DNA
<213> ORGANISM: Heterodera glycines
<220> FEATURE:
<221> NAME/KEY: CDS

```
<222> LOCATION: (1)..(561)

<400> SEQUENCE: 50 atg aaa ggc ttc ttc gcc ctg ttc gtc ttc gcc ttc acc ctt tcg gtg      48
Met Lys Gly Phe Phe Ala Leu Phe Val Phe Ala Phe Thr Leu Ser Val
1               5                   10                  15 ctt tct gcc gcc cat ttg ccg cct ttg gac att aac caa atc ccg gcc      96
Leu Ser Ala Ala His Leu Pro Pro Leu Asp Ile Asn Gln Ile Pro Ala
            20                  25                  30 gaa tac cgc gaa ttg atc ccc gag gag gtg acc aaa ttc tac cac gag     144
Glu Tyr Arg Glu Leu Ile Pro Glu Glu Val Thr Lys Phe Tyr His Glu
        35                  40                  45 ctg acc gag gat gac aaa aag gcg ctg aag gaa gtg gca gaa cgc cac     192
Leu Thr Glu Asp Asp Lys Lys Ala Leu Lys Glu Val Ala Glu Arg His
    50                  55                  60 gag gaa ttc caa acg gaa gag cag gca atg gaa gcg ctg aag gaa aag     240
Glu Glu Phe Gln Thr Glu Glu Gln Ala Met Glu Ala Leu Lys Glu Lys
65                  70                  75                  80 agt gag aag ctg tac aac aaa gcg gtc gaa ctg cgc acc ctt gtc aag     288
Ser Glu Lys Leu Tyr Asn Lys Ala Val Glu Leu Arg Thr Leu Val Lys
                85                  90                  95 gga aaa att gac caa ttg gtg ccc gac gcg aag gca ttc gtt atc ggg     336
Gly Lys Ile Asp Gln Leu Val Pro Asp Ala Lys Ala Phe Val Ile Gly
            100                 105                 110 atg atc gaa aag gca aag gga atg cgc ccg aag gcc ggc gag aag ccg     384
Met Ile Glu Lys Ala Lys Gly Met Arg Pro Lys Ala Gly Glu Lys Pro
        115                 120                 125 aag ctt gag gag ctg cgc acg gcg gcc aac gag ctg atc gag aag tac     432
Lys Leu Glu Glu Leu Arg Thr Ala Ala Asn Glu Leu Ile Glu Lys Tyr
    130                 135                 140 aaa gca ttg aat gac gaa gcc aaa gag tcg ctg aag tcc aac ttc ccc     480
Lys Ala Leu Asn Asp Glu Ala Lys Glu Ser Leu Lys Ser Asn Phe Pro
145                 150                 155                 160 aag att acg agc gtc atc caa aac gag aaa ttc caa acc ttg gcc aag     528
Lys Ile Thr Ser Val Ile Gln Asn Glu Lys Phe Gln Thr Leu Ala Lys
                165                 170                 175 agt ttg ctg aaa cag gag gca ccg gcc gcc taa                         561
Ser Leu Leu Lys Gln Glu Ala Pro Ala Ala
            180                 185

<210> SEQ ID NO 51
<211> LENGTH: 186
<212> TYPE: PRT
<213> ORGANISM: Heterodera glycines

<400> SEQUENCE: 51

Met Lys Gly Phe Phe Ala Leu Phe Val Phe Ala Phe Thr Leu Ser Val
1               5                   10                  15

Leu Ser Ala Ala His Leu Pro Pro Leu Asp Ile Asn Gln Ile Pro Ala
            20                  25                  30

Glu Tyr Arg Glu Leu Ile Pro Glu Glu Val Thr Lys Phe Tyr His Glu
        35                  40                  45

Leu Thr Glu Asp Asp Lys Lys Ala Leu Lys Glu Val Ala Glu Arg His
    50                  55                  60

Glu Glu Phe Gln Thr Glu Glu Gln Ala Met Glu Ala Leu Lys Glu Lys
65                  70                  75                  80

Ser Glu Lys Leu Tyr Asn Lys Ala Val Glu Leu Arg Thr Leu Val Lys
                85                  90                  95

Gly Lys Ile Asp Gln Leu Val Pro Asp Ala Lys Ala Phe Val Ile Gly
```

-continued

```
                100                 105                 110
Met Ile Glu Lys Ala Lys Gly Met Arg Pro Lys Ala Gly Glu Lys Pro
            115                 120                 125

Lys Leu Glu Glu Leu Arg Thr Ala Ala Asn Glu Leu Ile Glu Lys Tyr
    130                 135                 140

Lys Ala Leu Asn Asp Glu Ala Lys Glu Ser Leu Lys Ser Asn Phe Pro
145                 150                 155                 160

Lys Ile Thr Ser Val Ile Gln Asn Glu Lys Phe Gln Thr Leu Ala Lys
                165                 170                 175

Ser Leu Leu Lys Gln Glu Ala Pro Ala Ala
            180                 185
```

METHODS FOR MEASURING VIRULENCE IN SOYBEAN CYST NEMATODE

CROSS REFERENCE TO RELATED APPLICATIONS

This application claims the benefit of the earlier filing date of U.S. Provisional Applications No. 62/078,570 filed Nov. 12, 2014, 62/094,367 filed Dec. 19, 2014, and 62/239,046 filed Oct. 8, 2015. The disclosure of each of these prior applications is incorporated herein by reference in its entirety.

STATEMENT REGARDING FEDERALLY SPONSORED RESEARCH OR DEVELOPMENT

The subject matter of this disclosure was made with government support under contract number 2009-35302-05315 awarded by the United States Department of Agriculture. The government has certain rights in the invention.

FIELD

This disclosure relates to methods for the identification of soybean cyst nematode virulence.

BACKGROUND

Soybeans are a major cash crop and investment commodity, in North America and elsewhere. Soybean oil is one of the most widely used edible oils, and soybeans are used worldwide both in animal feed and in human food production.

The soybean cyst nematode (SCN), *Heterodera glycines*, is one of soybean's (*Glycine max*) most damaging pathogens. In the United States alone, SCN is estimated to cause over one billion dollars in annual soybean yield loss (Wrather & Koenning, *J Nematol* 38: 173-180, 2006). SCN is an obligate root parasite of soybean and forms an intricate association with it host in order to reproduce. The second-stage juvenile (J2) nematode burrows into the root using its hollow, protrudable stylet to physically and enzymatically disrupt the plant cells (Smant et al., *Proc Natl Acad Sci USA* 95: 4906-4911, 1998). Once the nematode reaches the vascular cells of the root it injects a complex mixture of proteins into a vascular cell, via its stylet, causing the formation of a multinucleate syncytium (Endo, *Phytopathology* 53: 622-623, 1963; Mitchum et al., *The New Phytologist* 199: 879-894, 2013). This highly metabolically active syncytia serve as a nurse cell throughout the rest of the nematode life cycle (Dropkin, *Ann Rev Phytopathology* 7: 101-122, 1969; Schmitt et al., "Biology and management of soybean cyst nematode." Marceline, Mo.: Schmitt & Associates of Marceline. xi, 262 p. p. 2004). The process of a syncytia formation is complex and involves nematode directed alterations of plant hormones, metabolic pathways and host gene regulation (Quentin et al., *Frontiers in Plant Science* 4: 53, 2013). However, since SCN is an obligate pathogen, it must have a functional syncytia to complete its life cycle. The suppression of host plant defense mechanisms is also very important (Abad & Williamson, *Advances in Botanical Research,* 53: 147-192, 2010). Host plant resistance to nematode infection has several layers, including preformed defenses and specific resistance genes (Williamson & Kumar, *Trends Genet* 22: 396-403, 2006). SCN possess specific virulence genes that are adapted to evade or suppress multiple types of plant defenses to successfully reproduce (Opperman & Bird, *Curr Opin Plant Biol* 1: 342-346, 1998). Genetic studies have indicated that resistance to SCN is polygenic in nature and numerous quantitative trait loci (QTLs) have been identified. Even though many SCN resistant cultivars exist, resistance derived from PI88788 and to a lesser extent Peking predominate the commercial seed market (Concibido et al., *Crop Science* 44: 1121-1131, 2004).

While proteins expressed from esophageal glands are undoubtedly important for nematode parasitism, it has been also suggested that glutathione peroxidases secreted from the hypodermis could protect cyst nematodes against reactive oxygen species (Jones et al., *Gene*324: 47-54, 2004). Likewise, a lipid binding protein secreted from the cuticle Gp-FAR-1 has been hypothesized to be an inhibitor of jasmonic acid signaling (Prior et al., *Biochem J* 356: 387-394, 2001). While not secreted proteins, biosynthetic enzymes involved in the production of vitamin B metabolites, pantothenate (VB5), biotin (VB7), thiamin (VB1) and pyridoxal 5-phosphate (VB6) could play a role in circumventing a starvation-based mechanism of nematode resistance (Craig et al., *Mol Biol Evol* 25: 2085-2098, 2008; Craig et al., *J Nematol* 41: 281-290, 2009). Two avirulence genes tied to specific host plant resistance genes have been identified in root knot nematodes (*Meloidogyne* spp.). The map-1 protein is secreted from nematode amphids (Castagnone-Sereno et al., *MGG* 282: 547-554, 2009; Semblat et al., *MPMI* 14: 72-79, 2001), while Mj-Cg-1 (Gleason et al., *Mol Plant Microbe Interact* 21: 576-585, 2008) when silenced via RNAi increased the level of root-knot nematode virulence. Interestingly, Mj-Cg-1 resides in a transposable-element family that may be important for the generation of genetic variation in a asexual nematode species (Gross & Williamson, *PLoS ONE* 6, 2011).

In cyst nematodes the best examples of avirulence genes are the SPRYSEC effector protein Gp_RBP-1 of *Globodera pallida* that has been shown to induce a specific hypersensitive reaction when co-expressed with the potato nematode resistance gene Gpa-2 (Sacco et al., *PLoS pathogens* 5: e1000564, 2009). Likewise, the venom allergen Gr-VAP1 of *G. rostochiensis* triggers a cell death response in tomato (*Lycopersicon esculentum*) plants containing the Cf-2 and Rcr3pim genes (Lozano-Torres et al., *Proc Natl Acad Sci USA* 109: 10119-10124, 2012).

Therefore, it is of particular importance, both to the soybean breeders and to farmers, to have the ability to test soil and identify the residing virulent soybean cyst nematode population. Identification of the biotype will enable a given interested party to employ specific integrated pest management practices for treatment of the soil and/or to develop a planting protocol that includes the identification of resistant soybean cultivars.

SUMMARY

Some phytoparasitic nematodes have the ability to infect and reproduce on plants that are normally considered resistant to nematode infection. Such nematodes are referred to as virulent and the mechanisms they use to evade or suppress host plant defenses are not well understood. Here, we report use of a genetic strategy, allelic imbalance analysis, to associate single nucleotide polymorphisms (SNPs) with nematode virulence on the most common source of resistance used to control *Heterodera glycines*, the soybean cyst nematode (SCN). To accomplish this analysis, a custom SCN SNP array was developed and used to genotype SCN F3-derived populations growing on resistant and susceptible soybean plants. Three SNPs reproducibly showed SNP allele imbalances between nematodes grown on resistant and susceptible plants. Two candidate SCN virulence genes that were tightly linked to the SNPs were identified. One SCN gene encodes a biotin synthase (HgBioB) and the other encodes a bacterial-like protein containing a putative SNARE domain (HgSLP-1). The two genes mapped to two different linkage groups. Both genes contained sequence polymorphisms between avirulent and virulent nematodes. In addition, the HgSLP-1 gene was reduced in copy number in virulent nematode populations. The gene encoding HgSLP-1 appeared to produce multiple forms of the protein via intron retention and alternate splicing, but was also part of a gene family.

HgSLP-1 encodes an esophageal-gland protein that is secreted by the nematode during plant parasitism. Silencing expression of the gene by RNAi increased the nematodes' ability to grow on susceptible soybean plants. In bacterial co-expression experiments, HgSLP-1 co-purified with the Rhg1 α-SNAP protein, suggesting this nematode protein binds to this SCN resistance protein. Collectively the data presented herein suggest that multiple SCN genes are involved in SCN virulence, and that HgSLP-1 may function as an avirulence protein and its absence may be used to evade detection of host defenses.

One of the putative nematode virulence genes aids in the synthesis of vitamin B7, biotin, suggesting part of the nematode resistance mechanism could involve vitamin depravation. The other putative virulence gene encodes a secreted protein that may function in the regulation of membrane fusion; it binds to a soybean protein implicated in causing nematode resistance. The gene that encodes this putative nematode virulence protein was deleted or reduced in copy number in virulent nematode populations, suggesting that the loss of this gene aids the nematode in evading the host-plant resistance gene. The method used to identify these putative nematode genes is expected to be broadly applicable to any plant nematode with a viable genetic system and to the analysis of nematode virulence, or to any measurable nematode phenotype.

In certain embodiments, the present disclosure provides a method for detecting virulent SCN populations. In an example of such methods, the method involves extraction of SCN cysts or eggs from the soil; placing the extracted SCN cysts or eggs in a small container and applying an effective amount of pressure to the extracted cysts or eggs to rupture the cells therein to provide a lysate; to the lysate, a proteinase K (PK) solution can be added to digest the proteins and release the DNA within the lysate, followed by removal of protein fragments and detergents to provide nematode DNA; analyze the DNA, for instance by providing the nematode DNA to a quantitative real-time polymerase chain reaction (QPCR) plate and conducting a QPCR run (e.g., of 1.5 hours) to permit detection of the SCN virulence gene allele frequency. Alternatively, the DNA could be analyzed using direct sequencing, or microarray analysis.

There is provided in a specific example a method, comprising: extracting soybean cyst nematodes (SCN) from a soil sample from a source location (or from an aggregated sample, taken from multiple sub-locations then mixed to obtain a sample more representative of a possibly heterogeneous distribution over the source location area); obtaining DNA from the extracted nematodes; and analyzing the DNA to determine at least one of: (a) the relative copy number of the HgSLP-1 gene in the nematode DNA, and/or (b) the sequence of the HgBioB gene in the nematode DNA, wherein a low relative copy number of HgSLP-1, or the presence of C at position 70 and/or A at position 132 (numbered with reference to SEQ ID NO: 44) within HgBioB, is indicative of SCN virulence in the soil sample. In a further example of such a method, the method further comprises planting in soil at the source location a soybean cultivar having a different source of resistance than that in PI88788 if there is SCN virulence in the soil sample.

Also provided herein is an isolated cDNA molecule, comprising (or consisting of) the nucleic acid sequence shown in SEQ ID NO: 41 (HgSLP-1); or in SEQ ID NO: 50 (HgFAR-1). Additional embodiments are recombinant nucleic acid molecule comprising a promoter sequence operably linked to one of the described nucleic acid molecules, as well as cells transformed with one or more such recombinant nucleic acid molecule(s).

Yet another embodiment is a kit, comprising a container comprising at least one labeled oligonucleotide specific for a HgBioB mutation sequence at position 70 or 132 (numbered with reference to SEQ ID NO: 44).

Another embodiment is a kit, comprising one or more container(s) comprising: a pair of primers specific for HgSLP-1; and at least one labeled oligonucleotide specific for HgSLP-1.

Without intending to be bound by any particular theory, there can be discussion herein of beliefs or understandings of underlying principles or mechanisms relating to embodiments of the disclosure. It is recognized that regardless of the ultimate correctness of any explanation or hypothesis, embodiments of the disclosure can nonetheless be operative and useful.

The foregoing and other objects and features will become more apparent from the following detailed description, which proceeds with reference to the accompanying figures.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 4. Multiple sequence alignment of the HgSLP-1 SNARE domain to related t-SNARE proteins. The ** marks the zero layer residue critical for membrane fusion and * indicates conserved hydrophobic residues in the flanking heptad repeat domains. The following sequences are in the alignment: 1). Locus: 2NPS_B; protein name: chain B; crystal structure of the early endosomal SNARE complex; accession: 2NPS_B; organism: *Rattus norvegicus* (Norway rat) (positions 1-60 of SEQ ID NO: 30). 2). Locus: HgSLP; protein name: *Heterodera glycines* SNARE-like protein 1; Accession: organism: *Heterodera glycines* (soybean cyst nematode) (positions 46-112 of SEQ ID NO: 31). 3). Locus:

SYP24_ARATH, protein name: putative syntaxin-24; accession: Q9C615; organism: *Arabidopsis thaliana* (thale cress) (positions 262-326 of SEQ ID NO: 32). 4. Locus: Q9SML5_CAPAN; protein name: syntaxin t-SNARE; accession: Q9SML5; organism: *Capsicum annuum* (peppers) (positions 210-275 of SEQ ID NO: 33). 5). Locus: Q8S4W4_PORYE; protein name: Syntaxin PM. Accession: Q8S4W4; Organism: *Pyropia yezoensis* (marine red alga) (positions 191-256 of SEQ ID NO: 34). 6). Locus: SYP72_ARATH; Protein name: Syntaxin-72; accession: Q94KK6; Organism: *Arabidopsis thaliana* (thale cress) (positions 170-235 of SEQ ID NO: 35). 7). Locus: BET1L_RAT; protein name: golgi SNARE 15 kDa; accession: 035152; organism: *Rattus norvegicus* (Norway rat) (positions 12-77 of SEQ ID NO: 36). 8). Locus: SNP30_ARATH; putative SNAP25 homologous protein SNAP30; accession: Q9LMG8; organism: *Arabidopsis thaliana* (thale cress) (positions 195-260 of SEQ ID NO: 37). 9). Locus: O44419_STRPU; Protein name: Synaptosomal-associated protein 25; accession: O44419; Organism: *Strongylocentrotus purpuratus* (purple sea urchin) (positions 143-208 of SEQ ID NO: 38). 10). Locus: O01389_HIRME; protein name: SNAP-25 homolog; ACCESSION: 001389; Organism: *Hirudo medicinalis* (medicinal leech) (positions 144-209 of SEQ ID NO: 39).

Figure 5:
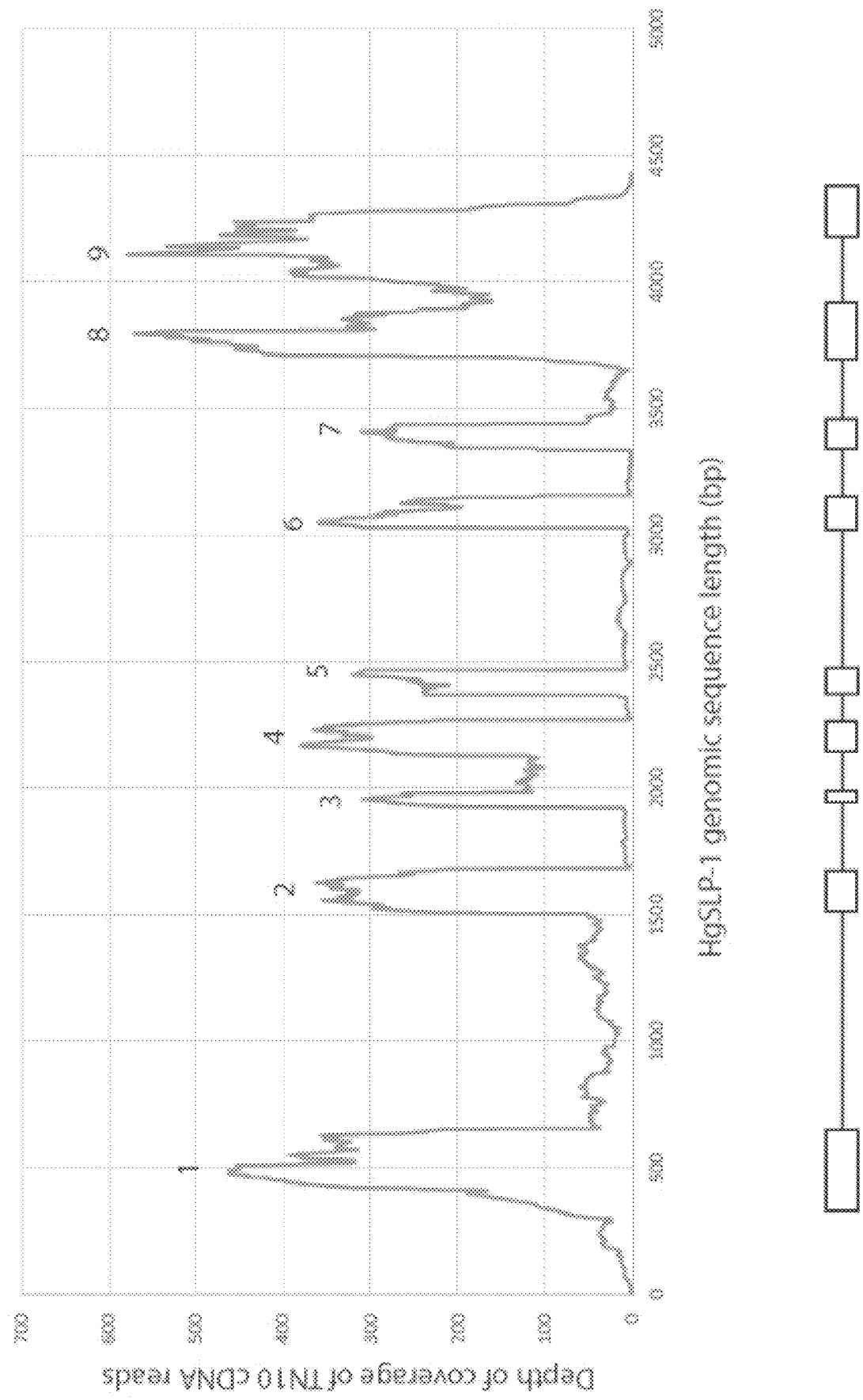

FIG. 5. Large read mapping of TN10 cDNA sequences to the HgSLP-1 genomic sequence. The Y-axis shows depth of mapped cDNA coverage (99% identical with 99% overlap of each read) and the X-axis indicates the base position along the HgSLP-1 gene. The numbers mark the exons of HgSLP-1.

FIG. 6A-6D. Immunolocalization of HgSNARE-like protein-1 (HgSLP-1). FIG. 6A-6D are 40× light field images matched with corresponding epifluorescent images of sections of SCN in soybean roots stained using HgSLP-1 antibodies. Arrows point to the basal cell of a subventral esophageal gland in FIG. 6A, the median bulb and esophageal lumen in FIG. 6B and the stylet in FIG. 6C. Panel FIG. 6D shows negative control sections lacking HgSLP-1 antibody staining in the nematode. Arrows in FIG. 6D point to the basal cell of an esophageal gland and the stylet.

FIG. 6D is a composite of two sequential sections from the same nematode. For all light field images, 20 micron scale bars are shown.

FIG. 7. Protein gel blot of HON ARE-like protein and soybean α-NAP protein expressed in *E. coli*. Proteins in lanes 1-5 were detected using an antibody that binds to HgSNARE-like protein-1 (HgSLP-1). Proteins in lanes 6-9 were detected using an antibody that binds to soybean α-SNAP. Lanes 1 and 6 contain purified protein from *E. coli* co-expressing full size HgSLP-1 and soybean α-SNAP. Lane 2, 3, 7, and 8 contain independent replicates purified protein from *E. coli* co-expressing HgSLP-1 missing its signal peptide and soybean α-SNAP. Lanes 4 and 9 contain purified protein from *E. coli* that only expresses full sized HgSLP-1. Lane 5 contains total protein from *E. coli* that only expresses full sized HgSLP-1. Protein sizes are shown in kDa.

FIG. 8. HgSLP-1 antibody binding intensity to proteins in gel filtration chromatography fractions containing either HgSLP-1 or both HgSLP-1 and α-SNAP (as indicated).

FIG. 9A-9D. Model for *Heterodera glycines* SNARE-like protein-1 (HgSLP-1) function. FIG. 9A. During normal plant membrane fusion, soybean v-SNARE proteins (green) interact with t-SNARE proteins (red) and SNAP-25 (yellow) to promote normal membrane fusion, while the NSF (purple) and α-SNAP (blue) are involved in recycling the SNARE proteins. FIG. 9B. In a susceptible interaction HgSLP-1 (black) inhibits membrane fusion by binding to a v-SNARE or soybean α-SNAP. FIG. 9C. In an incompatible interaction the resistant plants over produce the soybean α-SNAP (blue) to bind and neutralize the function of HgSLP-1. FIG. 9D. Virulent SCN lacking HgSLP-1, but containing a variant of the protein (grey), again suppress membrane fusion and promote nematode growth.

FIG. 10 is a graph illustrating HgSLP-1 copy number analysis, from a relative QPCR study of DNA extracted from field isolates of SCN from 14 different locations. The QPCR assay measures the frequency of HgSLP-1 (copy number varies) in each nematode population relative to HgFAR-1 (copy number does not vary). The shorter bars on the graph indicate SCN populations predicted to be the more virulent. The Y-axis shows the ratio of HgSLP-1 and HgFAR-1 (if the two genes are equal in copy number then the ratio is 1). The x-axis shows the sample name (1-14). Samples 1, 7, 9, 10 SCN were able to grow on susceptible and resistant soybean plants (PI88788) and have relatively low copies of HgSLP-1. Series 5 SCN were also able to grow on PI88788 SCN, but had intermediate HgSLP-1 copy number. However, Series 6 SCN, which has a relatively higher copy number of HgSLP-1, did not grow on PI88788, but did grow on a susceptible soybean plant. The other series SCN populations did not grow on either susceptible or resistant soybean, thus their virulence level is unknown.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95855-02_SeqList.txt, created on Feb. 29, 2016, ~108 KB, which is incorporated by reference herein.

SEQ ID NOs: 1 and 2 are forward and reverse primers used in a SNP assay.

SEQ ID NOs: 3 and 4 are probes used in the same SNP assay.

SEQ ID NOs: 5 and 6 are primers used in SYBR® green Q-PCR.

SEQ ID NOs: 7-14 are RNA sequences used in RNAi silencing of HgSLP-1.

SEQ ID NOs: 15 and 16 are forward and reverse used in detection of HgFAR-1, for instance for copy number assays.

SEQ ID NO: 17 is a probe used in detection of HgFAR-1, for instance for copy number assays.

SEQ ID NOs: 18 and 19 are forward and reverse used in detection of HgSLP-1 (Exon 2), for instance for copy number assays.

SEQ ID NO: 20 is a probe used in detection of HgSLP-1 (Exon 2), for instance for copy number assays.

SEQ ID NO: 21 is the sequence of a peptide used to generate antibodies to HgSLP-1.

SEQ ID NOs: 22 and 23 are forward and reverse primers used to amplify α-SNAP (Glyma18g02590), Accession Number LOC100814639.

SEQ ID NOs: 24 and 25 are forward and reverse primers used to amplify HgSLP-1 cDNA.

SEQ ID NOs: 26 and 27 are forward and reverse primers used to remove the signal peptide from HgSLP-1.

SEQ ID NOs: 28 and 29 are forward and reverse primers used to amplify soybean α-SNAP.

Figure 4:
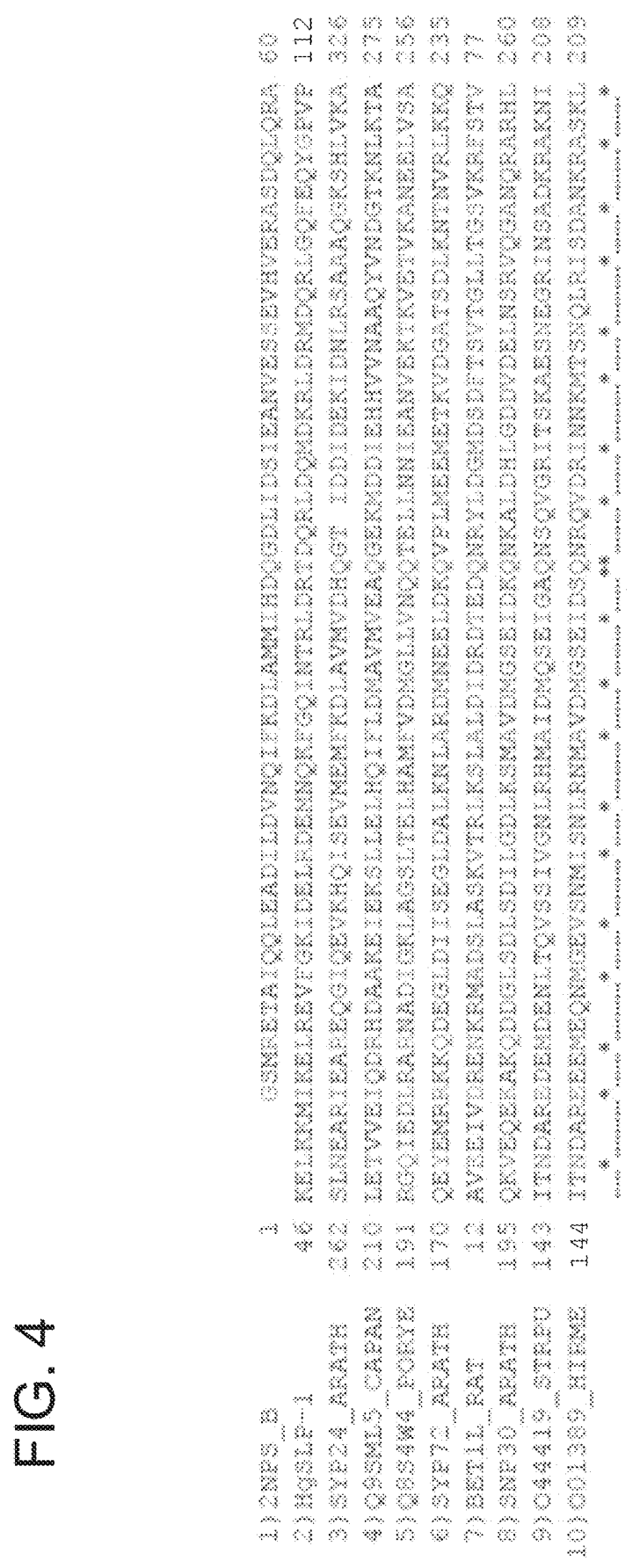

SEQ ID NOs: 30-39 are amino acid sequences of or containing the proteins/fragments aligned in FIG. 4, as follows:

| Locus/Accession | Protein Name | Organism | SEQ ID NO: |
| --- | --- | --- | --- |
| 2NPS_B/ 2NPS_B | chain B; crystal structure of the early endosomal SNARE complex | *Rattus norvegicus* (Norway rat) | positions 1-60 of SEQ ID NO: 30 |
| HgSLP | SNARE-like protein 1 | *Heterodera glycines* (soybean cyst nematode) | positions 46-112 of SEQ ID NO: 31 |
| SYP24_ARATH/ Q9C615 | putative syntaxin-24 | *Arabidopsis thaliana* (thale cress) | positions 262-326 of SEQ ID NO: 32 |
| Q9SML5_CAPAN/ Q9SML5 | syntaxin t-SNARE | *Capsicum annuum* (peppers) | positions 210-275 of SEQ ID NO: 33 |
| Q8S4W4_PORYE/ Q8S4W4 | Syntaxin PM | *Pyropia yezoensis* (marine red alga) | positions 191-256 of SEQ ID NO: 34 |
| SYP72_ARATH/ Q94KK6 | Syntaxin-72 | *Arabidopsis thaliana* (thale cress) | positions 170-235 of SEQ ID NO: 35 |
| BET1L_RAT/ O35152 | Golgi SNARE 15 kDa | *Rattus norvegicus* (Norway rat) | positions 12-77 of SEQ ID NO: 36 |
| SNP30_ARATH/ Q9LMG8 | putative SNAP25 homologous protein SNAP30 | *Arabidopsis thaliana* (thale cress) | positions 195-260 of SEQ ID NO: 37 |
| O44419_STRPU/ O44419 | Synaptosomal-associated protein 25 | *Strongylocentrotus purpuratus* (purple sea urchin) | positions 143-208 of SEQ ID NO: 38 |
| O01389_HIRME/ O01389 | SNAP-25 homolog | *Hirudo medicinalis* (medicinal leech) | positions 144-209 of SEQ ID NO: 39 |

SEQ ID NO: 40 (GenBank Accession Number KM575849) is the genomic sequence encoding HgSLP-1, with introns and exons as follows: Exon I, positions 1-141; Exon II, positions 994-1170; Exon III, positions 1412-1471; Exon IV, positions 1616-1756; Exon V, 1856-1954; Exon VI, positions 2514-2642; Exon VII, positions 2832-2927; Exon VIII, positions 3196-3294; and Exon IX, positions 3595-3633 (including the stop codon).

SEQ ID NOs: 41 and 42 are the cDNA sequence of HgSLP-1 and the protein encoded thereby.

SEQ ID NO: 43 is the nucleotide sequence of the Super 385 scaffold; the sequence encoding HgSLP-1 is positions 17,816-21,448.

SEQ ID NO: 44 is the BioB nucleotide sequence, including indications of the SNPs identified herein (position 70: C/G (TN10/TN20); position 132: G/A (TN10/TN20)). SEQ ID NO: 45 is the protein encoded by SEQ ID NO: 44; the SNPs result in variable amino acids at position 24 (Ala or Pro) and position 44 (Arg or Gln).

SEQ ID NOs: 46 and 47 are forward and reverse used in detection of HgSLP-1 (Exon a), for instance for copy number assays.

SEQ ID NO: 48 is a probe used in detection of HgSLP-1 (Exon a), for instance for copy number assays.

SEQ ID NO: 49 is the genomic sequence of HgFAR-1.

SEQ ID NOs: 50 and 51 are the cDNA sequence of HgFAR-1 and the protein encoded thereby.

DETAILED DESCRIPTION

I. Abbreviations

BC backcross
BioB biotin synthase
BSA bovine serum albumin
CM chorismate mutase
FAM™ fluorescein fluorescent dye
FD fold difference
Hg *Heterodera glycines*
HgBioB *Heterodera glycines* bacterial-like biotin synthase gene
HGT horizontal gene transfer
IPTG isopropyl-beta-D-thiogalactopyranoside
MGBNFQ major groove binder/non-fluorescent quencher
PBS phosphate buffered saline
PK proteinase K
PMSF phenylmethanesulfonyl fluoride
QPCR quantitative polymerase change reaction
Rhg SCN resistance complex genes
RNAi RNA interference
SCN soybean cyst nematode
SHMT serine hydroxymethyltransferase
SLP-1 SNARE-like protein-1
SNAP Soluble NSF Attachment Protein
SNARE SNAP REceptor
SNP single nucleotide polymorphism
TN10 strain of SCN, non-virulent on SCN-resistant soybean plants
TN20 strain of SCN, virulent on SCN-resistant soybean plants
VIC® a fluorescent dye II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

A coding sequence is the part of a gene or cDNA which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules.

Downstream refers to a relative position in DNA or RNA and is the region towards the 3' end of a strand.

Expression refers to the transcription of a gene into structural RNA (rRNA, tRNA) or messenger RNA (mRNA) and subsequent translation of an mRNA into a protein.

An amino acid sequence that is functionally equivalent to a specifically exemplified sequence is an amino acid sequence that has been modified by single or multiple amino acid substitutions, by addition and/or deletion of amino acids, or where one or more amino acids have been chemically modified, but which nevertheless retains one or more characteristics (e.g., biological and/or structural characteristics) of the protein. Functionally equivalent nucleotide sequences are those that encode polypeptides having substantially the same biological activity (or at least one biological activity) as a specifically exemplified protein.

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

Isolated means altered by the hand of man from the natural state. If an "isolated" composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'-5'-phosphodiester bonds.

Two DNA sequences are operably linked if the nature of the linkage does not interfere with the ability of the sequences to affect their normal functions relative to each other. For instance, a promoter region would be operably linked to a coding sequence if the promoter were capable of effecting transcription of that coding sequence.

Nucleic acid probes and primers can be readily prepared based on the nucleic acid molecules provided as indicators of virulence or resistance. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule that is not naturally found connected to the nucleic acid. Typical labels include but are not limited to radioactive isotopes, enzyme substrates, co-factors, ligands, chemiluminescent or fluorescent agents, haptens, and enzymes. More generally, a label is a composition detectable by (for instance) spectroscopic, photochemical, biochemical, immunochemical, or chemical means. Typical labels include fluorescent proteins or protein tags, fluorophores, radioactive isotopes (including for instance $^{32}P$), ligands, biotin, digoxigenin, chemiluminescent agents, electron-dense reagents (such as metal sols and colloids), and enzymes (e.g., for use in an ELISA), haptens, and proteins or peptides (such as epitope tags) for which antisera or monoclonal antibodies are available. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, John Wiley & Sons, New York (1998). A label often generates a measurable signal, such as radioactivity, fluorescent light or enzyme activity, which can be used to detect and/or quantitate the amount of labeled molecule.

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (*In Molecular Cloning: A Laboratory Manual*, CSHL, New York, 1989), Ausubel et al. (ed.) (*In Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as the HgSLP-1 or HgFAR-1 or HgBioB sequences described herein, for example, by using computer programs intended for that purpose such as Primer (Version 0.5, © 1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a tyrosine kinase protein encoding nucleotide will anneal to a target sequence, such as another homolog of the designated tyrosine kinase protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a tyrosine kinase-encoding nucleotide sequences.

Also provided are isolated nucleic acid molecules that comprise specified lengths of tyrosine kinase-encoding nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a HgSLP-1 or HgFAR-1 or HgBioB nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, e.g. about eighths, sixteenths, twentieths, fiftieths, and so forth, with similar effect.

Nucleic acid molecules may be selected that comprise at least 10, 15, 20, 25, 30, 35, 40, 50, 100, 150, 200, 250, 300 or more consecutive nucleotides of any of these or other portions of a HgSLP-1 or HgFAR-1 or HgBioB nucleic acid molecule, such as those disclosed herein, and associated flanking regions. Thus, representative nucleic acid molecules might comprise at least 10 consecutive nucleotides of the HgSLP-1 (SEQ ID NO: 41), HgFAR-1 (SEQ ID NO: 50) or HgBioB (SEQ ID NO: 44) cDNA.

A polypeptide is a linear polymer of amino acids that are linked by peptide bonds. Promoter means a cis-acting DNA sequence, generally 80-120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more non-homologous DNA molecules (for example a recombinant plasmid containing one or more inserts of foreign DNA cloned into at least one cloning site).

Transformation means the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. As used herein, "comprising" is synonymous with "including," "containing," or "characterized by," and is inclusive or open-ended and does not exclude additional, unrecited elements or method steps. Hence, "comprising A or B" means "including A" or "including B" or "including A and B." As used herein, "consisting of" excludes any element, step, or ingredient not specified in the aspect element. As used herein, "consisting essentially of" does not exclude materials or steps that do not materially affect the basic and novel characteristics of the aspect.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). References cited herein are incorporated by reference herein in their entirety to indicate the state of the art as of their publication or filing date and it is intended that this information can be employed herein, if needed, to exclude specific embodiments that are in the prior art.

The disclosure may be further understood by the following non-limiting examples. Although the description herein contains many specificities, these should not be construed as limiting the scope of the disclosure but as merely providing illustrations of some of the presently preferred embodiments of the disclosure. For example, thus the scope of the disclosure should be determined by the appended aspects and their equivalents, rather than by the examples given.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Every formulation or combination of components described or exemplified herein can be used to practice the disclosure, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

III. Overview of Several Embodiments

There is provided in a specific example a method, comprising: extracting soybean cyst nematodes (SCN) from at least one soil sample from a source location (or from an aggregated sample, taken from multiple sub-locations then mixed to obtain a sample more representative of a possibly heterogeneous distribution over the source location area); obtaining DNA from the extracted nematodes; and analyzing the DNA to determine at least one of: (a) the relative copy number of the HgSLP-1 gene in the nematode DNA, and/or (b) the sequence of the HgBioB gene in the nematode DNA, wherein a low relative copy number of HgSLP-1, or the presence of C at position 70 and/or A at position 132 (numbered with reference to SEQ ID NO: 44) within HgBioB, is indicative of SCN virulence in the soil sample. In a further example of such a method, the method further comprises planting in soil at the source location a soybean cultivar having a different source of resistance than that in PI88788 if there is SCN virulence in the soil sample.

In examples of the provided methods, analyzing the DNA to determine the relative copy number of the HgSLP-1 gene in the nematode DNA comprises measuring the abundance of the HgSLP-1 sequence compared to the copy number of a control nematode gene (e.g., HgFAR-1) using quantitative PCR.

Optionally, in embodiments of the provided methods, the method further comprises preparation a ratio of the copy number of HgSLP-1 to the copy number of the control nematode gene, and wherein a ratio of ≤0.2 indicates SCN virulence in the soil. In alternative embodiments, a ratio of ≤0.3, ≤0.35, ≤0.4, ≤0.45, or ≤0.5 indicates SCN virulence in the soil.

In another embodiment of the method, the quantitative PCR uses primer pair SEQ ID NOs: 18 and 19 or NOs: 46 and 47 to amplify HgSLP-1 DNA. By way of example, the copy number of the HgSLP-1 gene in the nematode DNA comprises detecting HgSLP-1 DNA using a labeled probe having the sequence of SEQ ID NO: 20 or 48.

In another embodiment of the method, the quantitative PCR uses primer pair SEQ ID NOs: 15 and 16 to amplify HgFAR-1 DNA. By way of example, the copy number of the HgFAR-1 gene in the nematode DNA comprises detecting the HgFAR-1 DNA using a labeled probe having the sequence of SEQ ID NO: 17.

Also provided herein is an isolated cDNA molecule, comprising the nucleic acid sequence shown in SEQ ID NO: 41 (HgSLP-1); or in SEQ ID NO: 50 (HgFAR-1). In another embodiment, the isolated cDNA molecule has a sequence consisting of the nucleic acid sequence shown in SEQ ID NO: 41 (HgSLP-1); or SEQ ID NO: 50 (HgFAR-1).

Additional embodiments are recombinant nucleic acid molecule comprising a promoter sequence operably linked to one of the described nucleic acid molecules, as well as cells transformed with one or more such recombinant nucleic acid molecule(s).

Yet another embodiment is a kit, comprising a container comprising at least one labeled oligonucleotide specific for a HgBioB mutation sequence at position 70 or 132 (numbered with reference to SEQ ID NO: 44)

Another embodiment is a kit, comprising one or more container(s) comprising: a pair of primers specific for HgSLP-1; and at least one labeled oligonucleotide specific for HgSLP-1. By way of example, in such a kit the pair of primers specific for HgSLP-1 may comprise SEQ ID NOs: 18 and 19 and at least one oligonucleotide specific for HgSLP-1 may comprise SEQ ID NO: 20. Alternatively, the pair of primers specific for HgSLP-1 may comprise SEQ ID NOs: 46 and 47 and at least one oligonucleotide specific for HgSLP-1 may comprise SEQ ID NO: 48. Optionally, such kits for detecting HgSLP-1 may in some embodiments further comprise: one or more additional container(s) comprising: a pair of primers specific for HgFAR-1; and at least one labeled oligonucleotide specific for HgFAR-1, for detecting a control sequence. Alternative, the pair of primers specific for HgFAR-1 may comprise SEQ ID NOs: 15 and 16 and at least one oligonucleotide specific for HgFAR-1 may comprise SEQ ID NO: 17.

IV. Discovery of Soybean Cyst Nematode (SCN) Virulence Genes, and Related Methods The soybean cyst nematode (SCN), *Heterodera glycines*, is one of soybean's (*Glycine max*) most damaging pathogens, causing billions of dollars in annual soybean yield losses (Wrather & Koenning, *J Nematol* 38: 173-180, 2006). SCN is an obligate parasite that must form a highly metabolically active, multinucleate nurse cell in the plant root (the syncytium) in order to complete its life cycle (Endo, *Phytopathology* 53: 622-623, 1963; Mitchum et al., *The New Phytologist* 199: 879-894, 2013; Dropkin, *Ann Rev Phytopathology* 7: 101-122, 1969' Schmitt et al., "Biology and management of soybean cyst nematode." Marceline, Mo.: Schmitt & Associates of Marceline. xi, 262 p. p. 2004). The process of syncytium formation is complex and involves nematode-directed alterations of plant hormones, metabolic pathways and host gene regulation (Quentin et al., *Frontiers in Plant Science* 4: 53, 2013), in addition to suppression of host-plant defense mechanisms (Abad & Williamson, *Advances in Botanical Research,* 53: 147-192, 2010). To prevent nematode infection, the plant utilizes several resistance mechanisms, including pre-formed defenses and specific resistance genes (Williamson & Kumar, *Trends Genet* 22: 396-403, 2006). Understanding the mechanisms host plants use to block nematode parasitism might provide insights into how some nematodes evade these defenses.

Genetic studies have indicated that resistance to SCN is polygenic, and numerous quantitative trait loci (QTLs) for SCN resistance have been identified. However a single accession Plant Introduction (PI) 88788, and to a lesser extent soybean cultivar (cv) Peking, predominate the commercial seed market (Concibido et al., *Crop Science* 44: 1121-1131, 2004). Recently, resistance genes to SCN were map-based cloned at two loci and both were shown to be atypical plant resistance genes (Cook et al., *Science* 338: 1206-1209, 2012; Liu et al., *Nature* 492: 256-260, 2012). The Rhg1 locus from PI88788 resistance was analyzed using an RNA interference (RNAi)-based approach identified three genes that were part of a tandem repeat encoding a soybean α-SNAP protein, a wound inducible protein and a potential amino acid transporter (Cook et al., *Science* 338: 1206-1209, 2012). The Rhg4 SCN resistance gene from cv Forrest (Peking-type resistance) was recently map-based cloned using targeting induced local lesions in genomes (TILLING), in combination with gene complementation and gene silencing (Liu et al., *Nature* 492: 256-260, 2012). Rhg4 also encoded a novel type of plant resistance gene, a serine hydroxymethyltransferase (SHMT), which is an enzyme involved in one carbon folate metabolism. The SCN resistance conferred by Rhg4 also requires Rhg1 to function fully, indicating the two seemingly different SCN resistance mechanisms work together in some unknown, but important way (Liu et al., *Nature* 492: 256-260, 2012).

Plant parasitic nematodes cause considerable damage to agricultural plants throughout the world. The use of naturally occurring, phytoparasitic nematode resistant plants can provide a sustainable, environmentally friendly management strategy. Unfortunately, nematode populations over time can adapt and reproduce on these "resistant plants". Such nematodes are referred to as virulent or resistance-breaking nematodes. If the molecular mechanism virulent nematodes used to evade or suppress host plant resistance were understood, then virulent populations could be monitored and management strategies could be devised, preserving valuable resistant plant germplasm.

Host-plant resistance is an effective and environmentally friendly management tool. However, virulent nematode populations are able to overcome plant defenses to successfully reproduce on resistant plants (Doyle & Lambert, *Mol Plant Microbe Interact* 16: 123-131, 2003). These "virulent" SCN are armed with specific virulence genes that have yet to be identified (Dong, & Opperman, *Genetics*. 146:4 1311-18, 1997; Sereno, *Euphytica,* 124:2 193-199, 2002; Cook et al., *Science* 338: 1206-1209, 2012). It is suggested that nematodes probably have to overcome both innate resistance common to many plants, and induced host-plant resistance mechanisms controlled by specific nematode resistance genes (Smant & Jones, "Suppression of Plant Defences by Nematodes." In: Jones et al., editors. Genomics and Molecular Genetics of Plant-Nematode Interactions. Dordrecht: Springer. pp. 273-286, 2011). In the case of basal resistance mechanisms, plant phytoalexins might be detoxified by esophageal-gland-expressed glutathione-S-transferase (Dubreuil et al., *The New Phytologist* 176: 426-436, 2007). Likewise, an esophagus-expressed chorismate mutase (CM) is thought to play a similar role by altering the production of chorismate-derived nematode toxins (Doyle & Lambert, *Mol Plant Microbe Interact* 16: 123-131, 2003; Lambert et al., *Mol Plant Microbe Interact* 12: 328-336, 1999). Some SCN CM alleles showed a correlation with SCN's ability to reproduce on some SCN-resistant soybean cultivars, suggesting some CM enzymes may aid the nematode in overcoming innate resistance mechanisms (Bekal et al., *Mol Plant Microbe Interact* 16: 439-446, 2003; Lambert et al., *Mol Plant Microbe Interact* 18: 593-601, 2005). Other nematode effectors that have been implicated in modulating host defense are GrSPRYSEC-19 (Rehman et al., *MPMI* 22: 330-340, 2009), Hg30C02 (Hamamouch et al., *J Exper Botany* 63: 3683-3695, 2012), Hs10A06 (Hewezi et al., *Plant Physiol* 152: 968-984, 2010), Hs4F01 (Patel et al., *J Exp Bot* 61: 235-248, 2010) and Mi-CRT (Jaouannet et al., *MPMI* 26: 97-105, 2013).

Much of how plant parasitic nematodes evade or suppress host plant resistance mechanisms depends on the corresponding plant-resistance genes involved in preventing the nematode from completing its life cycle. Thus, one might expect the unusual nematode resistance genes found at the Rhg1 and Rhg4 loci would require SCN to deploy equally unique mechanisms to overcome these atypical types of resistance. In this document, we describe the use of whole genome allelic imbalance or bulk segregant analysis to identify two candidate SCN virulence genes.

Provided herein are diagnostic assays, which measure copy number of the HgSLP-1 gene in a nematode population. If ratio of a control gene (such as HgFAR-1) to HgSLP-1 in the nematode population is near 1, then that nematode (population) is predicted to not grow on resistant plants where resistance involves a Rhg1 a-SNAP resistance gene. If the ratio is, for instance, 100 times lower (that is, if there is evidence of relative loss of HgSLP-1 gene in the tested nematode population), then the nematode (population) is predicted to grow on resistant soybean. If HgFAR-1 is low in copy number in the population, then it will grow on soybean containing the Rhg1 α-SNAP. If the HsSLP-1 gene has been lost in a (significant) portion of the nematode population, then the nematodes will be able to predate on the plants. If the gene is not present, they will grow on resistant plants containing the Rhg1 α-SNAP. However, soybean varieties having a different source of resistance than this would be predicted to still be resistant.

In another embodiment, to perform a test for the presence or absence of a mutation in a HgBioB sequence of population of nematodes, a suitable genomic DNA-containing sample from a soil site is obtained and the DNA extracted using conventional techniques. The extracted DNA is then subjected to amplification, for example according to standard procedures. The single base-pair mutation(s) in HgBioB is determined by conventional methods including manual and automated fluorescent DNA sequencing, primer extension methods (Nikiforov, et al., *Nucl Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single strand conformation polymorphism (SSCP), denaturing gradient gel electrophoresis (DGGE), Taq-Man™, oligonucleotide hybridization, and the like.

Sequences surrounding and overlapping single base-pair mutations in the HgBioB gene can be useful for a number of gene mapping, targeting, and detection procedures. For example, genetic probes can be readily prepared for hybridization and detection of the P24_A (position 70 G/C) and R44_Q (position 132 G/A) SNPs. As will be appreciated, probe sequences may be greater than about 12 or more oligonucleotides in length and possess sufficient complementarity to distinguish between the variant sequence and the wildtype, and may optionally be labeled with a detectable, non-naturally occurring label. Similarly, sequences surrounding and overlapping any of the specifically disclosed SNPs, or longer sequences encompassing for instance the entire length of one of the variant HgBioB sequences, or portions thereof, can be utilized in allele specific hybridization procedures.

HgBioB single nucleotide alterations, whether categorized as SNPs or new mutations can be detected by a variety of techniques. The techniques used in evaluating either somatic or germline single nucleotide alterations include allele-specific oligonucleotide hybridization (ASOH) (Stoneking et al., *Am. J. Hum. Genet.* 48:370-382, 1991), which involves hybridization of probes to the sequence, stringent washing, and signal detection. Other methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect the mutations in DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods. One of ordinary skills will recognize that other techniques for detecting single nucleotide polymorphisms are also applicable.

V. Kits

Kits are provided which contain reagents for determining the (relative) copy number of HgSLP-1, or the presence or absence of mutation(s) in a HgBioB sequence, such as probes or primers specific for the HgSLP-1 gene or a portion thereof, or a HgBioB SNP region, such as those regions surrounding position 70 or position 132. Such kits can be used with the methods described herein to determine whether a sample, such as a soil sample or aggregated soil sample, contains or is contaminated with virulent (or non-virulent) nematodes. The provided kits may also include written instructions. The instructions can provide calibration curves or charts to compare with the determined (e.g., experimentally measured) values.

Oligonucleotide probes and primers, including those disclosed herein, can be supplied in the form of a kit for use in detection of nematodes, or more specifically SCN virulence, in a sample such as a soil sample or aggregated sample. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for HgSLP-1 copy number, or the presence of a HgBioB mutation, can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (PCR Protocols, A Guide to Methods and Applications, Academic Press, Inc., San Diego, Calif., 1990), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

A kit may include more than two primers, in order to facilitate the in vitro amplification of HgSLP-1, HgFAR-1, and/or HgBioB sequence(s), for instance.

In some embodiments, kits may also include one or more reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of HgSLP-1, HgFAR-1, and/or HgBioB sequences or mutation(s). In certain embodiments, these probes will be specific for a potential mutation that may be present in the target amplified sequences (e.g., of HgBioB). The appropriate sequences for such a probe will be any sequence that includes one or more of the identified polymorphic sites, particularly nucleotide positions that overlap with the variants shown in position 70 or 132 of SEQ ID NO: 44.

It may also be advantageous to provide in the kit one or more control sequences for use in the amplification reactions. The design of appropriate positive control sequences is well known to one of ordinary skill in the appropriate art; representative controls, based on HgFAR-1, are also described herein.

The following examples are provided to illustrate certain particular features and/or embodiments. These examples should not be construed to limit the invention to the particular features or embodiments described.

EXAMPLES

Example 1

A SNARE-Like Protein and Biotin are Implicated in Soybean Cyst Nematode Virulence

Plant parasitic nematodes cause considerable damage to agricultural plants throughout the world. The use of naturally occurring resistant plants can provide a sustainable and environmentally friendly management strategy. However, nematode populations over time can adapt and reproduce on these "resistant plants". Such nematodes are referred to as virulent. If the molecular mechanism(s) that virulent nematodes use to evade or suppress host plant resistance were understood, virulent field populations could be monitored and management strategies devised, thus preserving valuable resistant plant germplasm.

This study describes the use of a genetic strategy to identify genes in the soybean cyst nematode that allow it to evade or suppress host plant resistance genes. Two potential nematode virulence genes were identified. One gene is involved in the synthesis of vitamin B7 (biotin), suggesting that part of the nematode resistance mechanism overcomes vitamin depravation. The other putative virulence gene encoded a secreted protein that might function in the regulation of membrane fusion. This protein interacted with a soybean protein implicated in plant resistance. The gene that encoded this putative nematode virulence protein was deleted or reduced in copy number in virulent nematode populations, suggesting that the loss of this gene aids the nematode in evading the host-plant resistance. The method used to identify these putative nematode genes is believed to be broadly applicable to any sexually reproducing plant nematode for the analysis of nematode virulence, or to any measurable nematode phenotype. It is believed to be useful for predicting virulence on any plant that uses a-SNAP-type resistance and any nematode that has a gene like HgSLP-1.

Methods

Development of SCN Population for Mapping and Selection

Soybean cyst nematodes, populations TN10 and TN20 were grown by standard methods and cysts were harvested and purified as previously described (Niblack et al., *Ann Appl Nematology* 25: 880-886, 1993). SCN controlled mating was conducted using a modification of the method described in Dong and Opperman 1997. Briefly, 200 susceptible soybean seedlings (cv Essex unless otherwise stated) were geminated and planted into 50 ml sand filled falcon tubes, that previously had a hole drilled into the bottom and were fitted with an absorbent wick. The tubes containing the seedlings were placed in a tray of water so that the wick would keep the sand uniformly moist throughout the experiment. Soybean seedlings were inoculated with a single inbred SCN strain TN10 J2, which was allowed to parasitize the plant for three weeks. Male SCN were collected by inoculating susceptible plants with J2s from the inbred TN20 SCN strain, and then after a week washing the soil off the roots and placing the plants in a hydroponic culture to collect the males that emerged one week later. Soybean plants were inoculated with SCN TN20 was one week after inoculation of the plants by TN10. To make the controlled cross, the soil was gently rinsed from the seeding inoculated with TN10 and visually inspected to identify SCN females. The plants containing the TN10 females were collected and replanted in sand and then inoculated with TN20 males. After a week, the $F_1$ eggs were collected and used to re-inoculate a susceptible soybean plant and they were allowed to randomly mate for one generation. Samples of $F_1$ J2s were also genotyped to verify they all were heterozygous (described below). The $F_2$ eggs were collected and used to re-inoculate a susceptible plant for one more generation to produce the $F_3$ SCN eggs, these again were used to infect susceptible plants, but some plants were placed into hydroponic culture to collect $F_3$ unmated female nematodes for mapping, while others were allowed to mate to produce cysts for $F_3$ derived single cyst lines used in the allelic imbalance analysis. Eighty four unmated females were harvested and frozen individually in 1.5 ml microcentrifuge tubes and stored at −80° C. until use. The DNA extraction method described in Atibalentja et al. (*Mol Genet Genomics* 273: 273-281, 2005) was used to extract the DNA from the unmated F3 female SCN.

For genotyping SCN $F_1$ J2s, individual nematodes were placed in 0.2 ml PCR tubes and a one-step proteinase K DNA extraction method, described in Craig et al. (*Mol Biol Evol* 25: 2085-2098, 2008), was used to liberate the nematode DNA. The DNA was genotyped using a 2× TAQ-MAN® master-mix (Life Technologies) following manufacturer recommendations. The SNP assay, run on an Applied Biosystems (Foster City, Calif.) 7900HT Sequence Detection System under recommended settings using the following primers and probes: F-primer: GCGGCAGATT-GAAGAAGCATTT (SEQ ID NO: 1), R-primer: GCACGGCACTGATCAGACA (SEQ ID NO: 2), Probe: FAM-CCTCTCCAT<u>G</u>CGGACC-MGBNFQ (SEQ ID NO: 3; SNP underlined), VIC-AGCCTCTCCAT<u>A</u>CGGACC-MGBNFQ (SEQ ID NO: 4; SNP underlined). ("FAM™" and "VIC®" are reporter dyes; "MGBNFQ" is the major groove binder/non-fluorescent quencher.) Standard PCR conditions were used for the TAQMAN® assays: 50° C. for 10 min, followed 95° C. for 10 minutes, then 40 cycles of 95° C. for 10 sec, and 60° C. for 1 min.

Selection of SCN Populations on Resistant and Susceptible Plants

Single cyst SCN lines were allowed to grow for two generations on susceptible soybean (Essex) and then ten lines were harvested and equal amounts of eggs pooled. Two pools of ten SCN $F_3$-derived lines were produced. Five SCN resistant (Rhg1) backcross 3 (BC3) and five susceptible BC3 soybean plants were inoculated with equal numbers of the pooled eggs and the nematodes were allowed to reproduce for one generation. One month later, the second pool of SCN eggs was used to inoculate a second set of five SCN resistant (Rhg1) backcross 3 (BC3) and five susceptible BC3 soybean plants. This set of plants served as a biological replicate for the allelic imbalance experiment.

For both experiments, the resulting cysts were harvested as described above, and approximately 50-100 cysts from each plant were placed into 1.5 ml microcentrifuge tubes, frozen in liquid nitrogen, pulverized with a steel pestle and then the DNA was extracted using a DNeasy tissue kit (Qiagen, Valencia Calif.) following the manufacturer's instructions. The extracted genomic DNA (50 µl) was precipitated by adding 20 µg of yeast tRNA, 1 µl of pellet paint NF, 5 µl of 3 M Na acetate to the genomic DNA, followed by 2.5 volumes of cold 100% ethanol. The resulting DNA precipitate was collected by centrifugation and washed with 70% ethanol, and then air-dried. The DNA was amplified using a GENOMIPHI™ DNA amplification kit following the manufacturer's recommendations (GE Healthcare, Piscataway N.J.). The resulting DNA was treated with EXOSAP-IT® PCR cleanup reagent to remove primers and nucleotides following manufacturer's instructions (Affymetrix). For all DNA samples the SCN DNA concentration was determined by SYBR® green QPCR using 2×SYBR® green master-mix (Life Technologies, Grand Island N.Y.), and primers GCCATTGGAGCGCCAGATGC (SEQ ID NO: 5) and GGCTCATCGGCGGCACAA (SEQ ID NO: 6). Standard PCR conditions were used for the TAQMAN® assays: 50° C. for 10 min, followed 95° C. for 10 minutes, then 40 cycles of 95° C. for 10 sec, and 60° C. for 1 min, followed by a melting curve cycle. A standard curve of SCN DNA with known concentration was used to calculate the absolute concentration of the amplified SCN DNA.

Allelic Imbalance Analysis

The SNP sequences were identified by comparing TN10 SCN cDNA sequences to SCN TN20 genomic DNA sequence. The TN10 cDNAs derived from J2 RNA (1,949, 251 sequence reads) and egg RNA (3,080,637 sequence reads) were produced by a 454 GS FLX sequencer at the University of Illinois, Roy J Carver Biotechnology Center, and were assembled into contigs using the de novo assembly program in the CLC Genomics Workbench (CLCbio, Boston, Mass.). The TN10 contig sequences were concatenated into one million base lengths and used as reference sequences for the alignment of 577,902,089 TN20 genomic sequences (paired-end 25 nucleotide reads) generated on the SOLiD™ sequencing platform (SeqWright Inc., Houston Tex.). SNPs were identified in the alignments and selected if the aligned TN20 reads were different from the TN10 cDNA reference sequence, if the coverage was between 20 and 50 reads deep and if there were not other SNPs within 100 bp. Selected SNPs were also confirmed by alignment with TN10 genomic sequences, also produced on a SOLiD™ sequencing platform as described above. A list of 1,536 SNPs was sent to Illumina (San Diego, Calif.) to synthesize the GoldenGate genotyping oligonucleotides. The SCN DNA was diluted to a concentration of 100 ng/µl and 50 µl was sent for genotyping. The GoldenGate genotyping was conducted at the University of Illinois Functional Genomics Laboratory in the Roy J. Carver Biotechnology Center following standard protocols. After genotyping the SCN genotypes and the theta values for each SNP and DNA sample were assigned using GENOMESTUDIO® V2011.1 (Illumina Inc.). The SCN genetic linkage groups were produced by downloading the SNP data from the GENOMESTUDIO® data analysis software program into Microsoft Excel where the SNPs were placed into phase with the parental nematode genotypes. The SCN genotypes, from 723 SNPs, were imported into MST Map (Wu et al., "*Efficient and Accurate Construction of Genetic Linkage Maps from Noisy and Missing Genotyping Data*." Philadelphia Pa. 395-406 p. 2007) to produce linkage groups. The following settings were used: population type RIL3, population_name LG, distance_function kosambi, cut_off_p_value $1.0 \times 10^{-13}$, no_map_dist 15.0, no_map_size 3, missing_threshold 0.25, estimation_before_clustering no, detect_bad_data yes, objective_function ML, number_of_loci 723, number_of_individual 84. The maps were drawn using the map draw macro in Microsoft Excel (Liu & Meng, *Yi chuan* 25: 317-321, 2003).

Annotation of SCN Scaffolds Containing Selected SNPs Linked to Virulence

The DNA sequence for each SNP that showed allelic imbalance was used to identify a SCN genomic sequence scaffold using BLASTN. The SCN scaffolds, build 1, were obtained from the JGI *Heterodera glycines* community genome sequencing project (available online at genome.jgi.doe.gov/). The JGI SCN genome is from SCN inbred strain TN10. The sequence data was used to make and search a BLASTN database within the CLC Genomics Workbench. SCN scaffolds that matched the SNPs were annotated by performing a large-gap read mapping using SCN cDNA sequence derived from 454 and Illumina sequencing platforms. The mapped cDNAs were used to define the beginning and end of the expressed genes on the transcripts and intron sequences were removed to produce a final cDNA sequence. All expressed genes on the scaffold were compared to protein sequences in the databases via BLASTX. The cDNA sequence for HgSLP-1 was confirmed by PCR amplifying the full-length cDNA using PCR primers flanking the open reading frame. To do this, TN10 RNA was extracted and converted to cDNA as described in Craig et al. (*Mol Biol Evol* 25: 2085-2098, 2008). The cDNA was amplified a proof reading thermostable DNA polymerase and then cloned into pCR2.1 plasmid vector. The DNA sequenced was determined at the University of Illinois Roy J. Carver Biotechnology Center. To identify DNA polymorphisms in the candidate virulence genes, genomic DNA sequence derived from SCN strain TN20 was mapped to each scaffold using the CLC Genomics Workbench and SNPs were identified using the quality-based variant detection program. The coiled-coil domain was identified using the program COILS on the ExPASy web site (Lupas et al., *Science* 252: 1162-1164, 1991). The t-SNARE domain was detected and the multiple sequence alignment was produced using NCBI's conserved domain database (Marchler-Bauer et al., *Nucleic Acids Res* 41: D348-352, 2013), but the conserved, zero-layer polar amino acid residue with the flanking hydrophobic amino acid heptad repeats were detected using hydrophobic cluster analysis (Callebaut et al., *CMLS* 53: 621-645, 1997). The signal peptide was predicted using the TargetP 1.1 server (Emanuelsson et al., *Nature Protocols* 2: 953-971, 2007), also found on the ExPASy web site.

Silencing of HgSLP-1 by RNAi

SCN inbred strain TN10 was used for RNAi experiments. Four DsiRNAs directed against HgSLP-1 were synthesized by Integrated DNA Technologies (Coralville, Iowa) and were used at a concentration of 200 pmoles per ml. SCN J2s, 10,000/ml were treated with the DsiRNAs in 50 mM octopamine in M9 media (Urwin et al., *Mol Plant Microbe Interact* 15: 747-752, 2002) overnight with rotation and were then inoculated on to plants and allowed to reproduce for 30 days, then the number of cysts that formed were counted. The experiment was repeated with similar results. NC1 negative control DsiRNA sequence (DS NC1) was obtained from Integrated DNA Technologies and used at the same concentration and conditions described above. Four sections of the gene transcript were targeted.

```
1S:
                                      (SEQ ID NO: 7)
5'-UCUAAUAGUGAUAACAGCCUGCUACUU-3'

1AS:
                                      (SEQ ID NO: 8)
3'-AGAUUAUCACUAUUGUCGGACGAUG-5'

2S:
                                      (SEQ ID NO: 9)
5'-AGACAAUAUGAGAACAUCGUGCCACAU-3'

2AS:
                                      (SEQ ID NO: 10)
3'-TCUGUUAUACUCUUGUAGCACGGUG-5'

3S:
                                      (SEQ ID NO: 11)
5'-GUUCAUUUCAUCUCGAAGCUCGUCGAU-3'
```

-continued

3AS:
(SEQ ID NO: 12)
3'-CAAGUAAAGUAGAGCUUCGAGCAGC-5'

4S:
(SEQ ID NO: 13)
5'-UGGUCGAGUCGUUGGUCUGUUCGGUCC-3'

4AS:
(SEQ ID NO: 14)
3'-ACCAGCUCAGCAACCAGACAAGCCA-5'

In the susceptible line (TN10), when treated with RNAi to inhibit expression of HgSLP-1, they grow better. However, knocking down in expression did not have an effect on a resistant plant (TN20). This experiment did not show an actual RNA difference.

Copy Number Analysis for HgSLP-1

SCN genomic DNA was extracted as described above for SCN strain TN10, TN20, OP20, OP25 and OP50. Two TAQMAN® probe-based gene expression assays were used to measure the copy number of the HgSLP-1 gene relative to a control gene, HgFAR-1 (SEQ ID NO: 49). Standard PCR conditions were used for the TAQMAN® assays: 50° C. for 10 min, followed 95° C. for 10 minutes, then 40 cycles of 95° C. for 10 sec, and 60° C. for 1 min. For each DNA type, triplicate PCR reactions were conducted and the entire experiment was conducted twice with similar results. The data were compared using the ΔCt method (Livak & Schmittgen, *Methods* 25: 402-408, 2001), where $\Delta Ct=Ct^{target}-Ct^{control\ gene}$ and the fold difference (FD) between the HgSLP-1 target gene and the HgFAR-1 control gene was calculated using the equation, $FD=2^{-\Delta Ct}$. The fold differences were normalized to OP25 since there was nearly no difference in ΔCt for this SCN population. HgFAR-1 (SEQ ID NO: 49) was known to be of consistent copy number Craig et al. (*Mol Biol Evol* 25: 2085-2098, 2008). The primer and probes for detection of HgFAR-1 were as follows: F-primer AGGTGACCAAATTCTACC (SEQ ID NO: 15), R-primer GGGTGTCCATTTATTTGC (SEQ ID NO: 16), Probe FAM-CTGACCGAGGATGGACAA-MGBNFQ (SEQ ID NO: 17). The HgSLP-1 TAQMAN® primers and probes detected sequences in the first intron of HgSLP-1, the following oligonucleotides were used: F-primer CGAGATGAAATGAACCAAA (SEQ ID NO: 18), R-primer GAGTCGTTTGTCCATTTG (SEQ ID NO: 19), Probe FAM-AACACGAGATTGGAC-MGBNFQ (SEQ ID NO: 20). Alternatively, the following HgSLP-1 TAQMAN® primers and probes are useful for detecting sequences in the first intron of HgSLP-1: F-primer TAGGCCCTGCCATATTTG (SEQ ID NO: 46), R-primer TCCTGTGTGTTTCAAGTG (SEQ ID NO: 47), Probe FAM-CAAGGAATGGGCTCAA-MGBNFQ (SEQ ID NO: 48).

Localization of HgSLP-1 Protein in SCN-Infected Soybean Roots

Antibodies to HgSLP-1 were generated from a synthetic peptide (CRHLFESGEASETAS; SEQ ID NO: 21) in rabbits and affinity purified by GenScript (Piscataway, N.J.). Susceptible soybean seedlings (Essex) were inoculated with inbred SCN strain TN10 eggs, which were allowed to hatch and infect the soybean roots for 5 days to generate a mixed age population of nematodes. Root sections containing SCN infection sites were dissected and 0.5 cm long root segments were placed in ice-cold FAA fixative (50% ethanol, 5% acetic acid, 10% formalin). The nematodes and roots were microwave-fixed and embedded in paraffin (Lambert et al., *Mol Plant Microbe Interact* 12: 328-336, 1999). Immunolocalization of HgSLP-1 was conducted by sectioning (10 μm) the paraffin embedded roots and mounting them on Probe-on-Plus slides (Fisher Scientific, Pittsburgh, Pa.) over night at 42° C. The slides were soaked twice in xylene for 5 minutes, and then incubated in 100% acetone for 5 minutes. After repeating the acetone incubation the slides were hydrated by soaking for 5 minutes each in 95%, then 85%, 70%, and 50% acetone. Finally they were soaked in distilled $H_2O$ and phosphate buffered saline (PBS: 137 mM NaCl, 2.7 mM KCl, 10 mM $Na_2HPO_4$, $KH_2PO_4$ pH 7.4) for 5 minutes each. The nematodes were permeabilized by incubating the nematodes in PBS containing 4 μg/ml proteinase K for 30 minutes. The proteinase K was inactivated by soaking the slides 5 minutes in PBS with 0.2% glycine, then in PBS with 1 mM phenylmethanesulfonyl fluoride (PMSE), followed by a 5 minute treatment in PBS. The slides were blocked with 10% goat serum in PBS for 30 minutes, and then washed with PBS with 0.1% bovine serum albumin (BSA) for 5 minutes. The slides were incubated for two hours with the HgSLP-1 add primary antibody or pre-immune serum as a negative control (1:250 dilution) in PBS with 0.1% BSA, then washed 3 times, 10 minutes each wash, in PBS with 0.1% BSA. Next, the slides were incubated with the secondary antibody, goat-anti-rabbit labeled with OREGON GREEN® 488 dye (Life Technologies) in PBS with 0.1% BSA (1:250 dilution) and incubated for 2 hours. Finally, the slides were washed 3 times (10 minutes each wash) in PBS with 0.1% BSA. The slides were washed once with water and mounted with a coverslip using Prolong anti-fade and allowed to dry overnight. The sections were observed on a Zeiss Axio Scope 2 florescence microscope and digital images were captured with a Zeiss Axiocam. These experiments were conducted three times with similar results.

Production of α-SNAP Antibodies

Total RNA from soybean cv Forrest was converted to cDNA and used as a template to PCR amplify α-SNAP (Glyma18g02590) accession number LOC100814639 using primers XmaI-SNAP-F: AAACCCGGGAATGGCCGATCAGTTATCGAAGG (SEQ ID NO: 22) and XhoI-SNAP-R: AAAACTCGAGTCAAGTAATAACCTCATACTCC (SEQ ID NO: 23). The resulting PCR product was cloned between XmaI and XhoI cloning sites in the pGEX-5x-1 vector that adds a GST-tag (pGEX-5x-1-SNAP-GST). The construct was confirmed to be correct by sequencing (Genewiz, South Plainfield, N.J.). The construct plasmid was transformed into *E. coli* BL21 and sent to Rockland Immunochemicals (Gilbertsville, Pa.) where the company produced and purified the protein and then injected it into rabbits. The SNAP polyclonal antibody was affinity purified and cross adsorbed to remove antibodies that might bind to the GST tag.

Characterization of HgSLP-1 by Co-Expression/Co-Purification

The HgSLP-1 protein sequence (SEQ ID NO: 42) derived from SCN strain TN10 and the susceptible allele of the soybean α-SNAP were used to synthesize the coding region using DNA STRINGS™ DNA (Life Technologies). HgSLP-1 cDNA (SEQ ID NO: 41) was PCR amplified using primer HgSLP1F-BglII: GGTCTTGAGCGGATATCTTAACCGG (SEQ ID NO: 24) and primer HgSLP1R-EcoRV: CTCGACATCTCAGATCTATGGCACC (SEQ ID NO: 25) which had had terminal start-BglII and EcoRV-end sites for cloning. The cDNA was PCR amplified using CloneAmp HiFi PCR premix (Clontech, Mountain View Calif.) and 10 pmoles of each primer using 98° C., 10 sec and 25 cycles of 98° C. for 10 sec, 60° C. for 15 sec, 72° C. for 10 sec followed by a 72° C. for 2 min. The PCR products were gel purified and the cDNA insert was digested with the restriction enzymes BglII and EcoRV and ligated into the second expression position of the vector pCDF Duet-1 (Novagen, San Diego, Calif.) digested with the same enzymes. The pCDF Duet-1-HgSNP-1 vector was then transformed into *E. coli* Top10 cells. Selection was performed on spectinomycin (50 mg/ml) LB agar plates. The resulting plasmid containing HgSLP-1 was verified for accuracy by sequencing the nematode gene at the University of Illinois Roy J. Carver Biotechnology Center. Later the HgSLP-1 plasmid was transformed into JM109DE3 *E. coli* and used as a negative control that expresses only the HgSLP-1 protein.

The signal peptide was removed from the HgSLP-1 gene in the pCDF-Duet-1 vector by PCR amplifying the plasmid with primers HgSLP-1deltaspF: GAAAAAGCAGCACCGAATGC (SEQ ID NO: 26) and HgSLP-1deltaspR: CGGTGCTGCTTTTTCCATA-GATCTGCCATATGTATATCTCCT (SEQ ID NO: 27). The PCR was conducted using CLONEAMP™ HiFi PCR premix as described above, except that the extension time was 30 seconds. The resulting PCR product was treated with cloning enhancer, the plasmid was circularized using the In-Fusion HD enzyme premix and was transformed into *E. coli* Stellar competent cells following the manufacturers protocol (Clontech). The resulting plasmid containing HgSLP-1 missing the signal peptide was verified for accuracy by sequencing the nematode gene as described above.

The cDNA of the soybean α-SNAP was synthesized using DNA Strings (Life Technologies). The cDNA was PCR amplified using primers soysnapF-EcoRI: TCGCGAATGCGAATTCATGGCCGAT (SEQ ID NO: 28) and soysnapR-SalI: CGTCGAGCATGTCGACT-CAATGGTG (SEQ ID NO: 29) contained start-EcoRI and end-SalI sites. The cDNA was digested with EcoRI and SalI and ligated into the first expression position of pCDF Duet-1-HgSLP-1. The plasmid was then transformed into JM109DE3 *E. coli* that contains the T7 RNA polymerase gene and allows isopropyl-beta-D-thiogalactopyranoside (IPTG) induction of the lac-T7 promoters on pCDF-Duet-1. For all protein expression experiments, the *E. coli* containing the construct was grown at 37° C. until $OD_{600\ nm}$ was 0.4, then it was induced with 1 mM IPTG for 4 hours at 30° C. The induced *E. coli* cells were collected by centrifugation, suspended in 50 mM sodium phosphate (pH 7.4), 150 mM NaCl containing 1× Halt Protease Inhibitor cocktail, lacking EDTA (Thermo Scientific) and lysed using a B-PER bacterial protein extraction kit (Fisher Scientific) following the manufacturer's instructions. The protein concentration of the resulting *E. coli* protein extract was determined using the Pierce BCA protein assay kit (Fisher Scientific). Equal concentrations of proteins from the negative control and experimental samples were purified using Dynabeads His-Tag Isolation kit (Life Technologies) following manufacture's protocol. The eluted proteins were run on a Mini-Protean TGX SDS-PAGE 4-20% gradient gel (BioRad, Hercules Calif.) and the proteins were transferred to a nitrocellulose membrane using an iBlot dry blotting system (Life Technologies). The protein blot was incubated with blocking buffer (0.1 M maleic acid, 0.15 M NaCl, 1% BSA, 0.3% Triton X-100) for one hour. The primary polyclonal antibodies, anti-HgSLP-1 or anti-α-SNAP, were diluted 1:5000 in blocking buffer and incubated with the blot for 30 minutes and were then washed with blocking buffer three time for 10 minutes each. The secondary antibody, goat anti-rabbit alkaline phosphatase conjugate, was also used at a 1:5000 dilution in blocking buffer and was incubated and washed as described above. The secondary antibody was detected using Western Blue Stabilized substrate for alkaline phosphatase (Promega, Madison Wis.) and the reaction was stopped using TE (10 mM Tris-HCL, 1 mM EDTA) after approximately 20 minutes of development at room temperature. The experiment was repeated with similar results.

The total *E. coli* protein extracts expressing HgSLP-1 alone or both HgSLP-1 and α-SNAP were analyzed by gel filtration chromatography. The gel filtration column was 50 cm tall and had a diameter of 1.8 cm. The column was packed with SUPERDEX™ 75 prep grade resin (Amersham Biosciences) and a Bio-Rad ECONO™ gradient pump and model 2110 fraction collector were used to pack and collect the protein fractions. The column was equilibrated using 50 mM sodium phosphate (pH 7.4), 150 mM NaCl buffer and then calibrated using a LMW gel filtration calibration kit (Amersham Biosciences). Blue dextran 2000 was used to determine the void volume of the column and ribonuclease A (13.7 kDa), chymotrypsinogen A (25.0 kDa), ovalbumin (43.0 kDa), albumin (67.0 kDa) were used in the column calibration. For each column run, the flow rate of the column of 0.25 ml/minute and each fraction was collected for two minutes. Before each sample was added, 200 μl of blue dextran 2000 was added to the column, allowed to run into the column for one minute, then 200 μl of protein extract was added (either HgSLP-1 or the extract containing both HgSLP-1 and α-SNAP). The extracts were the same ones used in the co-purification experiments described above. The fractions obtained were tested for the presence of HgSLP-1 using a protein dot blots. Briefly, 400 μl of each fraction was precipitated by adding 1600 μl of cold acetone. The proteins were allowed to precipitate on ice for 30 minutes, then they were centrifuged and the acetone was removed from the protein pellet. The proteins were dried in a SPEEDVAC™ concentrator and then suspended in 10 μl of 1×SDS PAGE buffer and boiled for 5 minutes. 2 μl of the protein fraction was spotted onto nitrocellulose, dried, and then the HgSLP-1 was detected as described above. The resulting spots were quantified using NIH image and the resulting intensities were plotted using Microsoft excel. The experiment was repeated with similar results.

DNA and RNA Sequence Data

The HgSLP-1 gene (genomic) sequence is deposited in GenBank Accession Number KM575849 (40). All next-generation DNA sequence data used in this project is deposited in the NCBI BioProject 680464 titled, "*Heterodera glycines* genome sequencing".

Genomic Sequence:

SCN strain TN20 SOLiD™ sequencing platform (2×25 base 3 kb mate pair) 577,902,089 reads.

SCN strain TN10 SOLiD™ sequencing platform (50 base) 270,363,891 reads.

RNAseq:

SCN strain TN10 454 sequencing platform: J2 RNA (1,949,251 sequence reads) and egg RNA (3,080,637 sequence reads) 200-500 base.

SCN strain TN10 Illumina sequencing platform (2×75 base paired end) 263,530,527 reads. SCN strain TN10 Illumina sequencing platform (2×100 base paired end) 365,288,386 reads.

SCN SNPs:

1536 SNP and flanking sequence.

DNA sequences for scaffolds: 385 (SEQ ID NO: 43), 1924 and 20.

Results

Allelic Imbalance Analysis:

Dong & Opperman (*Genetics* 146: 1311-1318, 1997) established that genetic analysis of SCN virulence was feasible. The subsequent development of high throughput DNA sequencing and genotyping methods made a map-based approach to identify SCN virulence genes possible. In this project we constructed an $F_3$ mapping population of SCN, segregating for virulence, and then used an allelic imbalance/bulk segregation-based approach to identify regions of the SCN genome containing virulence gene candidates.

To create the SCN mapping population, two inbred SCN strains were crossed. The female parental strain, TN10, was non-virulent and the male parental strain, TN20, was virulent on SCN resistant soybean. The resulting $F_1$ nematodes were allowed to randomly inter mate for two generations to generate a mapping population of unmated $F_3$ female SCN and $F_3$ single cyst derived populations to use for allelic imbalance analysis.

A pool of F3 single cyst derived populations was used to inoculate soybean plants containing the Rhg1 resistance locus, or susceptible plants harboring only the susceptible Rhg1 alleles. The resulting cysts were harvested from all plants and the DNA was extracted. The SCN populations used in the selection experiments contained both virulent and avirulent SCN, thus one would expect the frequency of SCN virulence genes to increase in SCN populations grown on soybean harboring the Rhg1 resistance locus, but not on the susceptible plants. Furthermore, genetic recombination in the SCN genome should create a condition in the SCN population where allelic ratios of single-nucleotide polymorphisms (SNPs) in or near SCN virulence genes should be altered, but SNPs physically farther away from or unlinked to virulence genes will not have distorted ratios of SNP alleles in comparison to the susceptible control. This type of allelic imbalance or bulk segregant analysis can be a useful genetic approach if a way of conducting high-throughput SNP analysis is available.

Since commercial genotyping tools were absent for SCN, a custom Illumina SNP array was developed. At the time of the initiation of this project, the SCN genome was not available, so cDNA sequence reads of SCN inbred strain TN10 from egg and J2 developmental stages were collected, assembled and used as a template to identify SNPs in the SCN genome. SNPs that differed between the parental strains were identified by aligning genomic sequence collected from both parental inbred strains. A total of 1536 SNPs were selected that were homozygous between the parental SCN inbred strains and these were used to generate custom genotyping oligonucleotides for the Illumina GoldenGate genotyping system.

Figure 1:
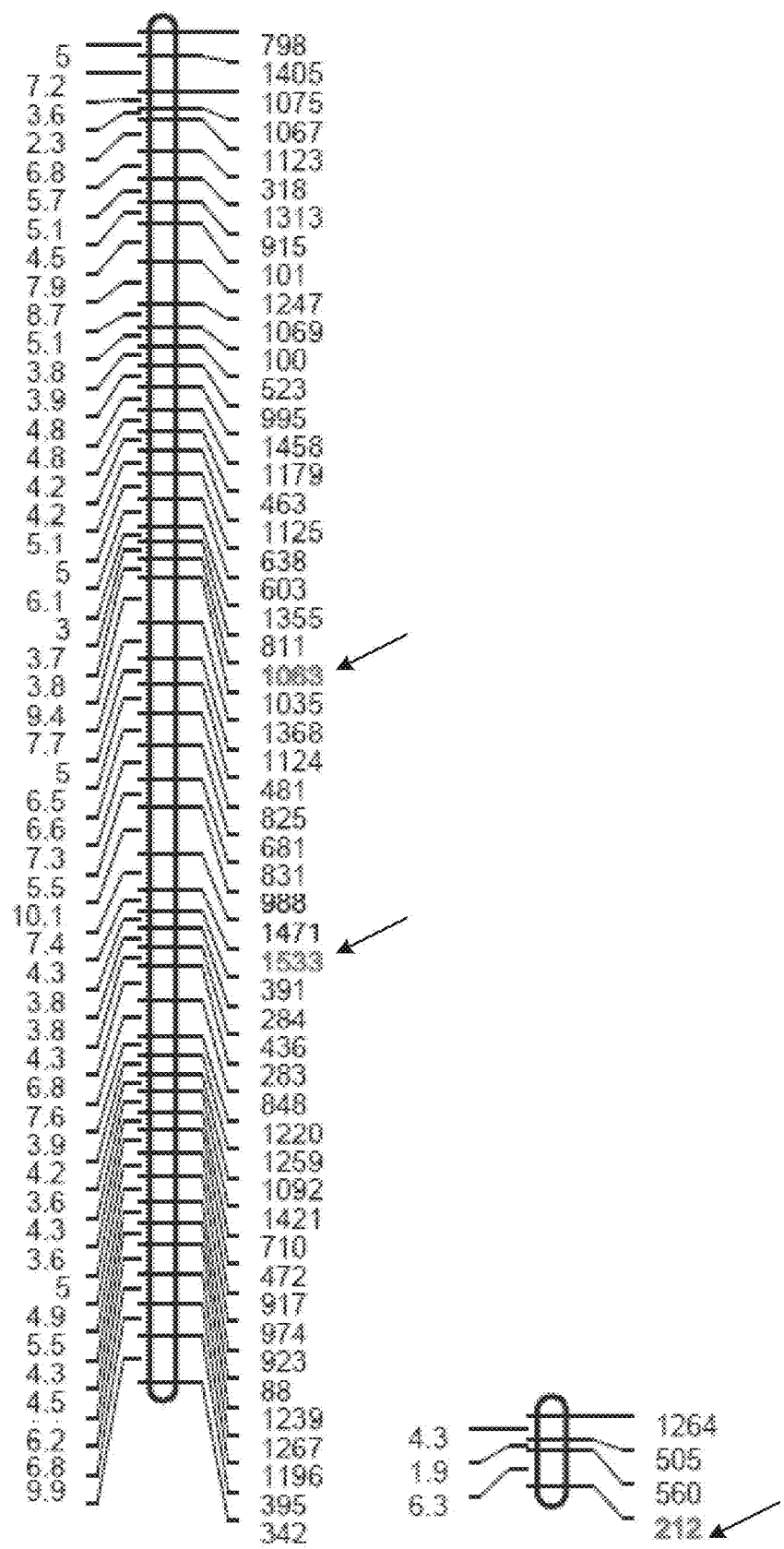
FIG. 1. SCN genetic linkage groups containing SCN SNPs linked to virulence. The left column has the map distance in centimorgans and the right column shows the SNP number. The SCN SNPs that show an allelic imbalance when grown on resistant and susceptible soybean plants are indicated with arrows.

Two types of SCN DNA were genotyped, one was a set of 10 DNA samples for the allelic imbalance analysis and the other was a set of 84 DNA samples extracted from the $F_3$ mapping population. Parental DNA from SCN strain TN10 and TN20 were run as controls. The experiment was repeated to provide a biological replicate. In the allelic imbalance analysis, out of the 1536 SNPs tested, three SNPs showed a statically significant imbalance where the virulent and avirulent SNP allele consistently differed in frequency when the bulk SCN populations were grown on susceptible and resistant plants. Thus, the three SNPs (212, 1063 and 1533) were considered good candidates for markers linked to SCN virulence loci (Table 1). A partial genetic map containing these three SNP markers was constructed from the SCN $F_3$ mapping population SNP data and showed that the three virulence associated SNPs mapped to two different linkage groups (FIG. 1).

TABLE 1

Theta values for allelic imbalance analysis

| | SNP 212 | | SNP 1533 | | SNP 1063 | |
|---|---|---|---|---|---|---|
| | Susceptible | Resistant | Susceptible | Resistant | Susceptible | Resistant |
| Experiment 1[a] | | | | | | |
| Rep 1[b] | 0.1894[a] | 0.3439 | 0.5882 | 0.6592 | 0.3201 | 0.3737 |
| Rep 2 | 0.2335 | 0.4187 | 0.607 | 0.6850 | 0.2509 | 0.3860 |
| Rep 3 | 0.2634 | 0.4705 | 0.5903 | 0.6775 | 0.2924 | 0.3765 |
| Rep 4 | 0.2702 | 0.4609 | 0.4251 | 0.7285 | 0.2070 | 0.3830 |
| Rep 5 | 0.3180 | 0.4698 | 0.4775 | 0.6734 | 0.3694 | 0.3508 |
| Mean | 0.2549 | 0.4327 | 0.5376 | 0.6847 | 0.2879 | 0.374 |
| Std Dev[d] | 0.0475 | 0.0540 | 0.0813 | 0.0262 | 0.0624 | 0.0138 |
| P[e] | | 0.00014 | | 0.00214 | | 0.00243 |
| Experiment 2 | | | | | | |
| Rep 1 | 0.2262 | 0.3309 | 0.4815 | 0.5297 | 0.1614 | 0.2084 |
| Rep 2 | 0.2201 | 0.3086 | 0.4933 | 0.5238 | 0.1779 | 0.1796 |
| Rep 3 | 0.1691 | 0.3076 | 0.4288 | 0.5422 | 0.1450 | 0.2192 |
| Rep 4 | 0.1727 | 0.3484 | 0.3894 | 0.5090 | 0.1474 | 0.1812 |
| Rep 5 | 0.1713 | 0.2608 | 0.4208 | 0.5984 | 0.1399 | 0.2389 |
| Mean | 0.1919 | 0.3112 | 0.4427 | 0.5406 | 0.1543 | 0.2054 |
| Std Dev | 0.0286 | 0.0329 | 0.0435 | 0.0344 | 0.0154 | 0.0253 |
| P[c] | | 0.00014 | | 0.00214 | | 0.00243 |

[a]Experiment 1 and 2 are replicates of the entire experiment;
[b]Rep 1-5 are technical replicates within each experiment;
[c]Significant differences in theta values for SNPs from SCN populations grown on susceptible and resistant soybean lines indicate allelic imbalances;
[d]Std Dev = standard deviation;
[e]P = probability from one-tailed Student's T-Test.

Identification of Linked Candidate Virulence Genes Via Homology and Polymorphisms:

To examine the genomic regions containing the SNPs associated with virulence, a SCN genome sequence was required. Fortunately, a draft assembly of the SCN TN10 genome was recently completed by the Joint Genome Institute (JGI). BLASTN was used to match the DNA sequence flanking the SNPs to the genome scaffolds. The BLASTN search identified three scaffolds; scaffold 385 (40,259 bp; SEQ ID NO: 43) for SNP 212, scaffolds 1924 (15,316 bp) for SNP 1063 and scaffold 20 (176,619 bp) for SNP 1533.

Although it was unknown how close the SNPs might be to candidate SCN virulence gene(s), it was thought that a closely linked SCN virulence gene could be identified based upon homology to known pathogenicity related proteins and the presence of sequence polymorphisms between virulent and avirulent SCN.

Since the SCN scaffolds were from a preliminary build of the SCN genome, they were not annotated. To identify expressed genes, SCN transcriptome DNA sequence, derived from egg and J2 RNA, was aligned to the scaffolds. The beginning and end of the expressed genes were identified and intron sequences were removed. The resulting cDNA sequences were then compare to known proteins using BLASTX (Table 2). Plant parasitic nematodes acquire genes via horizontal gene transfer (HGT) from microorganisms, which often plan a role in plant pathogenesis (Craig et al., *Mol Biol Evol* 25: 2085-2098, 2008; Smant et al., *Proc Natl Acad Sci USA* 95: 4906-4911, 1998), thus any HGT candidates on the scaffolds were given extra scrutiny. On two of the scaffolds, potential HGT candidates were identified. Scaffold 385 (SEQ ID NO: 43) contained a gene with homology to a bacterial protein from *Paenibacillus dendritiformis*, as well as a 162 amino acid fragment of a unpublished putative dorsal esophageal gland protein, Ha-dsl-1, from *Heterodera avenae* (AD182806.1).

TABLE 2

Protein homology of expressed genes on SCN genome scaffold 385

| Seq. | Size (bp) | Protein match | Organism | Accession # | e-Value |
|---|---|---|---|---|---|
| A | 349 | No significant similarity | | | |
| B | 2822 | No significant similarity | | | |
| C | 787 | No significant similarity | | | |
| D | 1756 | Phosphoglycerate mutase domain containing protein | *Haemonchus contortus* | CDJ82788.1 | 1e−16 |
| E | 1000 | Zinc finger BED domain-containing protein | *Ciona intestinalis* | XP_004227062.1 | 3e−08 |
| F | 978 | Protein of unknown function | *Paenibacillus dendritiformis* | WP_006677173 | 8e−06 |
| G | 2871 | Dorsal esophageal gland protein | *Heterodera avenae* | ADI82806 | 6e−24 |
| H | 539 | Protein of unknown function | *Haemonchus contortus* | CDJ97289 | 1.9e−02 |
| I | 2109 | Protein of unknown function | *Ascaris* | ERG83921.1 | 5e−04 |
| J | 1262 | No similarity | | | |
| K | 2348 | Protein of unknown function | *Necator americanus* | ETN70279.1 | 3e−09 |
| L | 2748 | Regulator of nonsense transcript | *Haemonchus contortus* | CDJ83790.1 | 3e−12 |

The Ha-dsl-1 protein is 463 amino acids in length, however, only 62 amino acids of the N-terminus of the SCN Ha-dsl-1-like protein was identified in scaffold 385. The remaining 100 amino acids of the predicted SCN Ha-dsl-1-like protein were not similar to Ha-dsl-1. Furthermore, when genomic sequences from SCN TN10 and TN20, collected from an Illumina sequencer, were aligned to the SCN Ha-dsl-1-like gene, the same allelic form was present in both SCN TN10 and TN20, thus this gene was not considered a promising virulence gene candidate.

Figure 2:
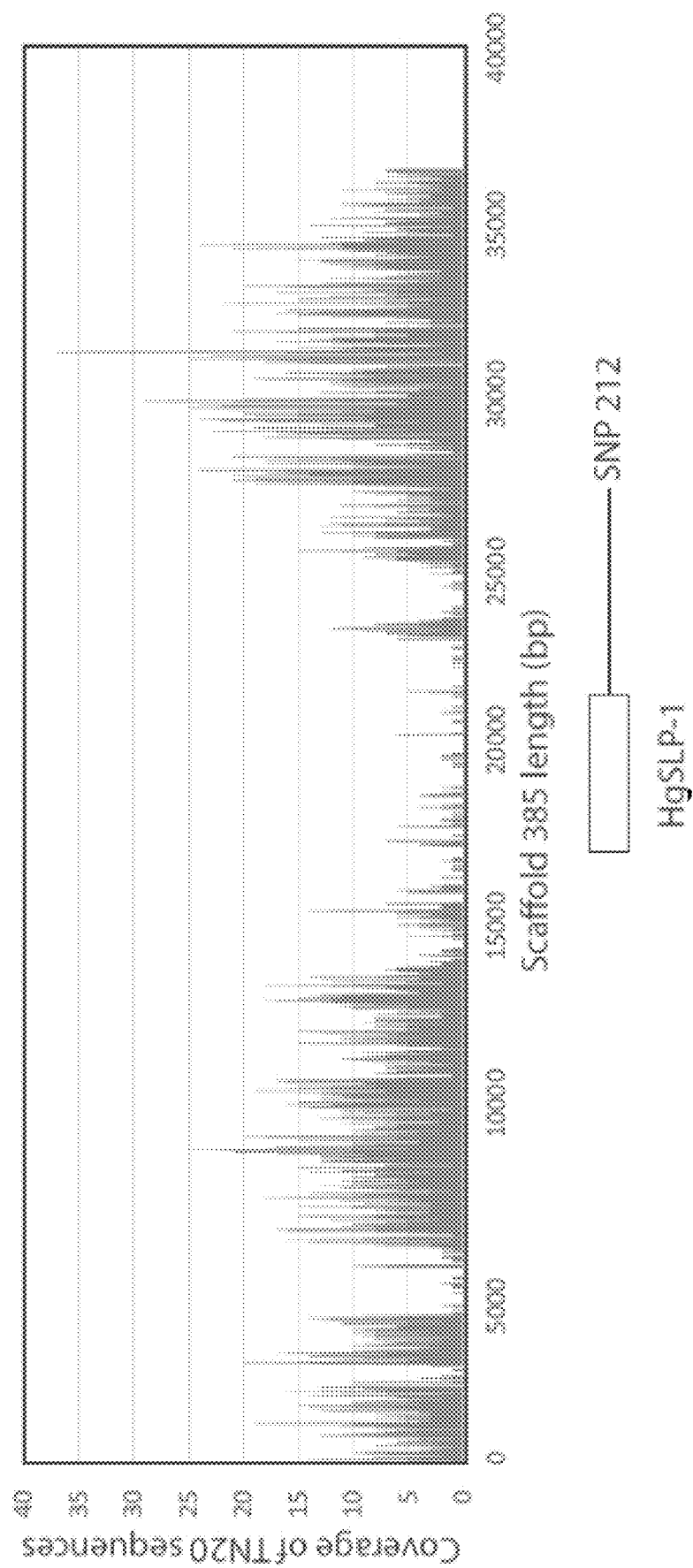
FIG. 2. Alignment of paired SOLiD DNA sequencing reads from SCN inbred strain TN20 to the scaffold 385 reference sequence derived from TN10 genomic sequence. The Y-axis shows depth of coverage and the X-axis indicated the base position along the scaffold. The HgSLP-1 gene spans bases 17816 to 21445.
Figure 3:
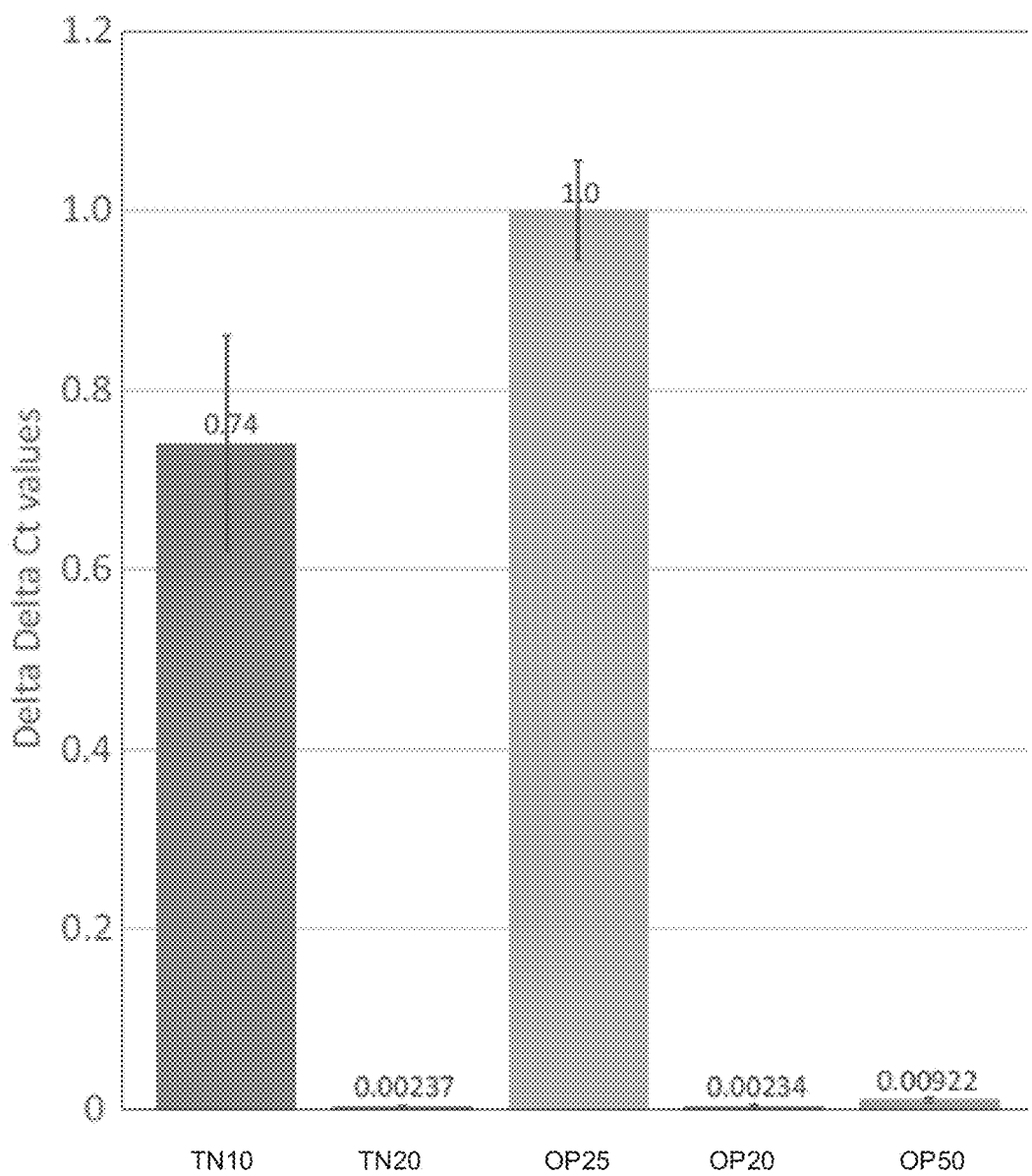
FIG. 3. Quantitative PCR of HgSLP-1 genomic copy number relative to HgFAR-1 in inbred SCN strains, TN10, TN20 OP25, OP20 and OP50.

However, the SCN *Paenibacillus dendritiformis*-like protein in scaffold 385, which spans from base positions ~18,000 to 22,000 in the scaffold (SEQ ID NO: 43), appeared more interesting. When Illumina TN10 and TN20 genomic sequences were aligned to this gene, substantially lower numbers of the TN20 sequences mapped to the SCN *P. dendritiformis*-like gene (FIG. 2). Also, very few reads from TN20 matched a large intron spanning 4,000 to 6,000 bp, but the coding region of the gene was well covered (FIG. 2). The low TN20 read coverage suggested the SCN *P. dendritiformis*-like gene was reduced in copy number in the virulent TN20 SCN. A TaqMan assay was developed that compared the fold difference in copy number of the *P. dendritiformis*-like gene to a reference SCN gene HgFAR-1 (SEQ ID NO: 49). This assay was used to verify the copy-number reduction; an over 300-fold drop between TN10 and TN20 populations, of the SCN *P. dendritiformis*-like gene in the TN20 inbred SCN population (FIG. 3). The copy-number reduction also occurred in two other unrelated virulent SCN strains, (OP20 and OP50) but not in another non-virulent SCN strain (OP25), suggesting the copy number of this gene in the nematode population may be important for SCN virulence (FIG. 3).

SCN scaffold 1924 contained a previously identified bacterial-like biotin synthase gene (HgBioB) (Craig et al., *J Nematol* 41: 281-290, 2009). TN20 and TN10 Illumina genomic reads were aligned to the HgBioB gene to identify sequence polymorphisms. The HgBioB protein contained amino acid sequence differences between non-virulent TN10 and virulent TN20 SCN inbred lines at P24_A and R44_Q (see SEQ ID NOs: 44 and 45 for the nucleotide and amino acid sequences).

SCN scaffold 20, while larger than the others, did not contain an obvious HGT or SCN effector gene candidate.

SEQ ID NO: 44 is the BioB sequence; the two possible nucleotides at the two SNPs identified herein (position 70: C/G (TN10/TN20); position 132: G/A (TN10/TN20)) are italicized and underlined.

ATGCCACCCCCAATTGGCTCAATTATTTCCAAATGGACTTTCTCTGAGGC

CCTTTCGGTGTTTTCACTC*C/G*CTTTCCCCGAACTCATTTTTCGTGCCC

AAAATGTCCATCAGCAGCATCACAATCCAAGCC*G/A*AGTTCAAATCAGT

ACGTTGTTGAGCATAAAAACGGGCGCGTGTCCGGAGAACTGTTCGTACTG

TCCGCAGTCGGGCTACCATAAGACGGGGCTGAAGAAGGAGCCGTTGATGG

AAGTGGAACAGGTGTTGGAAGCCGCTAAAAGAGCAAAGGCCAGCGGCGCG

ACACGATTTTGTATGGGGCGGCATGGAGGGGCCCGAAGGACCGCGACTT

GGACAAAGTGTGCGAAATGGTGGCCAAAGTCAAACAATTGGGTGGCCTTG

AAACATGCGCGACTTTGGGACTGCTCAAAAACGAGGGACAGGCGCAAAGA

CTGAAGAAAGCGGGATTGGACTTTTACAACCACAACATCGACTGCTCCAA

GGACTTTTACCACAAAATCATTACAACGCGCCGCTTTGATGACCGAATTT

CGACCATTGAGAAAGTTCGTTCGGCCGGCATCAAAGTTTGCTGCGGAGGA

ATTATCGGAATGGGAGAGAATAACGAAGAACGGGTGAAAATGCTCGTCAC

ATTGGCCAATTTCGCACCTCCGCCCGAATCGGTGCCAATTAACAAATTAA

TGCCCTTCCCCGGCACTCCGTTGGCCAATGCCCCGGCGCCCGACCCCTTC

GATTTCGTGCGCACAATTGCCACGGCGCGTGTTCTGATGCCAATGGCTTA

CATCCGACTGTCGGCTGGCAGAGAGCAAATGGCGGACGAATTGCAGGCAC

TTTGTTTTTTAGCCGGTGCGAATTCACTTTTCTTTGGGGAAAAGTTACTA

-continued
ACGGCGTCAAATCCAATGCCAGAAAAAGACAAAGAATTATTTCAACGATT

GGGTCTCAAAAGAGAGCAAATTGAGGAGAAAAAAGCTGAACGGAATGACG

AAAAAGTGACCTTGAACTTGTGA

Gene Structure and Transcript Variation:

The SCN *P. dendritiformis*-like gene in scaffold 385 was intriguing since it had the most dramatic difference between virulent and avirulent SCN in the allelic imbalance analysis, and appeared to be deleted or substantially altered in the virulent SCN parent. For this reason this sequence was chosen for further analysis. The SCN *P. dendritiformis*-like gene encodes a predicted protein of 326 amino acids (36.8 kDa) containing a 20-amino acid signal peptide and a 70 amino acid coiled-coil domain at amino acid positions 41 through 111. The coiled-coil region is similar to members of the target soluble N-ethylmaleimide sensitive fusion protein (NSF) attachment protein (SNAP) receptor domain superfamily (t-SNARE, e8.0×10$^{-3}$). SNARE proteins are highly conserved in eukaryotes and are involved in mediating membrane fusion events between cell membranes. The SNARE motif consists of a central polar amino acid residue (R or Q) flanked by hydrophobic amino acids in a heptad repeat pattern that interacts with other proteins in the SNARE complex and excludes water. The SCN *P. dendritiformis*-like protein contained these structural motifs when compared to known plant and animal t-SNARE proteins (FIG. 4), thus this sequence was named *Heterodera glycines* SNARE-like protein 1 (HgSLP-1; SEQ ID NO: 42). The central polar amino acid in HgSLP-1 was threonine, which is found in some t-SNARE-like proteins that alter eukaryotic membrane fusion, but is atypical for eukaryotic SNARE motifs (Paumet et al., *PLoS ONE* 4: e7375, 2009). Since soybean SCN-resistance genes encode proteins involved in membrane fusion (Cook et al., *Science* 338: 1206-1209, 2012; Matsye et al., *Plant Mol Biol* 80: 131-155, 2012), this nematode gene was further characterized.

The genomic sequence encoding the HgSLP-1 gene (SEQ ID NO: 40) contained 9 exons and 8 introns. However, the gene also showed evidence of intron sequence retention because most introns showed some coverage when Illumina cDNA reads were aligned to the genome sequence, with introns 3 and 8 showing the highest coverage (FIG. 5). If transcripts were produced containing intron sequences, the resulting proteins would be truncated due to stop codons in all of the intron sequences. The one exception is intron 3, which does not have a stop codon, but does have enough cDNA coverage so that one third of the transcripts could retain this intron. In this case, it would be expected that a protein 48 amino acids longer would be produced (FIG. 5). In addition, alignments of cDNA to the genomic sequence indicates a three-nucleotide deletion occurs 13% of the time due to an apparent alternative splice site at the beginning of exon 3. This alternative spliced form would produce a protein one amino acid shorter, missing Q107, which is at the end of the t-SNARE domain and thus could be functionally significant. Furthermore, the first exon of HgSLP-1 appears to be similar to PTR7 and Mer40 repetitive sequences identified in SCN expressed sequence tags (ESTs) B1748250 and CB824834, respectively, making the first exon, and related sequences more abundant than a single copy gene. Most of the ESTs that matched HgSLP-1 were only similar in the first repetitive exon, but two ESTs from SCN eggs (CB825264 and CA940412) were related to HgSLP-1, 73% identical over the first two exons, but only 57% identical overall. This suggests SCN expresses at least two forms of HgSLP, but the gene related to the EST is missing part of the t-SNARE domain, again suggesting it could have an altered function.

Silencing of HgSLP-1 by RNAi:

The deletion of the HgSLP-1 gene in virulent nematodes suggested that it might be possible to mimic this effect via the use of RNAi. To this end, non-virulent SCN containing HgSLP-1 were treated with four synthetic dsiRNAs directed against HgSLP-1. As a negative control, the same avirulent SCN were treated with the same amount of a non-nematode dsiRNA. Equal numbers of dsiRNA treated nematodes were inoculated onto susceptible and resistant (Rhg1 or Rhg4) soybean plants. After 30 days the number of cysts were counted. The number of cysts that formed on either type of resistant plant did not statistically differ between SCN populations treated with dsiRNAs that targeted the control gene or HgSLP-1. However, the number of cysts that grew on the susceptible plants was statistically higher for the plants inoculated with SCN treated with the dsiRNAs directed at the HgSLP-1 gene in comparison to the control (Table 3). RT-QPCR was conducted to detect the level of HgSLP-1 transcript from the dsiRNA treated J2s, but the expression of the gene in the J2 developmental stage was too low for reproducible quantification.

TABLE 3

Growth of RNAi treated SCN on nematode resistant and susceptible plants

| | Cysts per plant | | | | | |
|---|---|---|---|---|---|---|
| | Susceptible | | Rhg1 | | Rhg4 | |
| Plant | HgSLP-1 | NC | HgSLP-1 | NC | HgSLP-1 | NC |
| 1 | 139$^a$ | 112 | 0 | 0 | 19 | 10 |
| 2 | 176 | 89 | 3 | 2 | 31 | 12 |
| 3 | 189 | 62 | 1 | 0 | 19 | 26 |
| 4 | 115 | 54 | 5 | 3 | 21 | 20 |
| 5 | — | 55 | — | 9 | 23 | 26 |
| Mean ± S.E. | 155 ± 34 | 74 ± 26 | 2.25 ± 2.2 | 2.8 ± 3.7 | 22.6 ± 5 | 18.8 ± 7.6 |
| P | 0.009 | | 0.790 | | 0.380 | |

HgSLP-1 denotes SCN treated with dsiRNAs for HgSLP-1 and NC denotes SCN treated with negative control dsiRNA.
The "—" indicates the plant died before cysts could form.

Figure 6C:
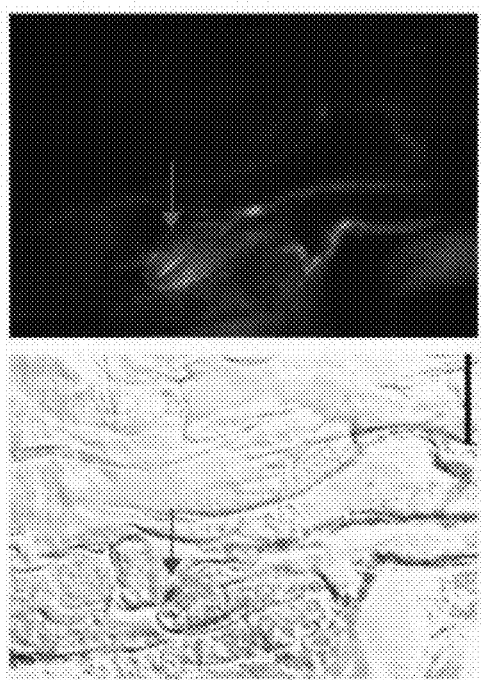
Figure 6D:
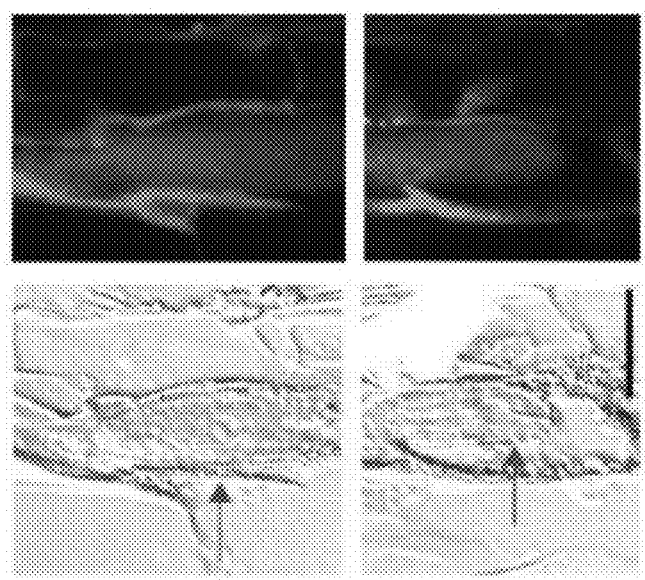
Figure 6A:
Figure 6B:
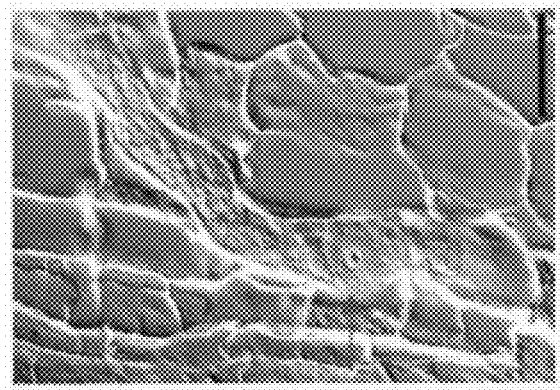

HgSLP-1 Protein Localization:

The presence of a potential signal peptide at the N-terminus of HgSLP-1 suggested it was a possible secreted protein. Immunolocalization experiments were conducted to localize the protein in the nematode while it was parasitizing the plant to determine if it was expressed in a nematode cell type that might secrete the protein from the nematode into the plant. To do this, peptide antibodies to HgSLP-1 were produced and incubated with nematode infested root sections. When the HgSLP-1 antibodies were detected via florescent microscopy, the antibodies bound to a subventral esophageal gland, indicated by the extensive florescent signal emitted from the basal cell body (FIG. 6A). Distinct antibody staining was also observed in the gland extension, metacorpus and esophageal lumen and stylet (FIGS. 6B and C). While florescent signals were also observed in plant cells walls adjacent to the nematode, we do not interpret this signal as the in planta location of HgSLP-1 since florescent signals are also observed in plant cell walls near the nematode in control sections. However, florescent signals in an esophageal gland or stylet are never observed in control sections. The fact that florescent signal is present in the esophageal lumen and stylet is consistent with the HgSLP-1 being secreted from the nematode since at this point the protein would have passed the valves in the metacorpus and there would be not further barriers to HgSLP-1 leaving the nematode. However, this data does not show that HgSLP-1 is injected into the nematode feeding cell. Future higher-resolution microscopic studies on SCN feeding cells will be required to address the plant subcellular location of HgSLP-1. Since HgSLP-1 appeared to be secreted, it is reasonable to assume that it could be injected into the nematode feeding cell and interact with soybean proteins.

Figure 7:
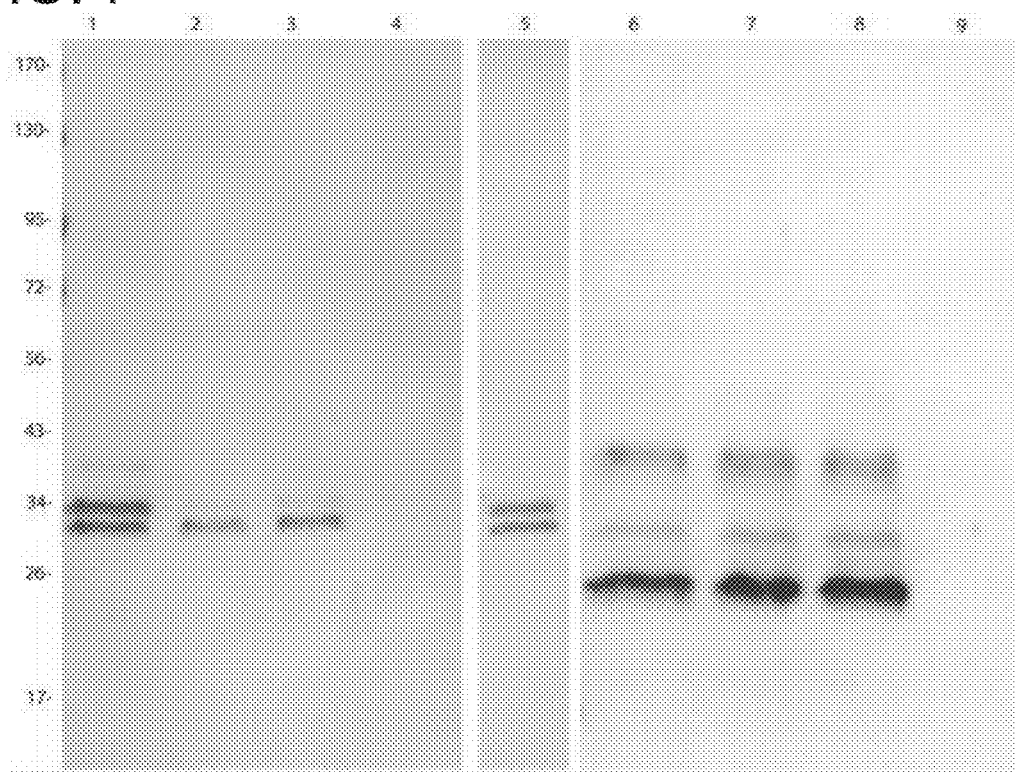

Characterization of HgSLP-1 by Co-Expression/Co-Purification:

The coiled-coil domain of HgSLP-1 was similar to domains found in t-SNARE proteins, suggesting that a number of plant proteins involved in membrane fusion might bind this nematode effector. Because one of the genes at the Rhg1 locus is predicted to encode an α-SNAP, we hypothesized that the soybean Rhg1 α-SNAP might directly bind to HgSLP-1 because α-SNAPs and t-SNARE proteins interact during the membrane fusion cycle. To test this hypothesis, we placed the genes for HgSLP-1 and the soybean α-SNAP from the Rhg1 locus in an *Escherichia coli* dual expression vector. For HgSLP-1 two forms were used in two different constructs, a full length and a form lacking the signal peptide. Likewise, a full-length α-SNAP gene was used, however, a C-terminal six-histidine (6×his) tag was added to allow for purification of the expressed α-SNAP protein. The *E. coli* were induced to co-express both proteins and then the bacterial cells were lysed under non-denaturing conditions and the proteins purified. As a negative control we expressed just the HgSLP-1, which lacks the 6×his tag, in *E. coli* and attempted to purify it in parallel with the co-expressed proteins. Protein gel blots were conducted on the purified proteins and they were detected using both anti-HgSLP-1 and anti-soybean α-SNAP antibodies (FIG. 7). In the lanes containing proteins purified from the co-expressed *E. coli*, both HgSLP-1 and soybean α-SNAP could be detected within 20 minutes, suggesting they were both abundant in the purified proteins. Trypsin digestion and mass spectrometry also detected fragments of both proteins in purified samples. The negative control, the full size HgSLP-1 alone, did not purify, but the protein was easily detected in the initial total *E. coli* lysates and was equivalent in amount to the co-expressed HgSLP-1, which indicates it did not bind to the chromatography beads (FIG. 7). This co-purification of HgSLP-1 and soybean α-SNAP occurred even when the metal affinity chromatography beads were very stringently washed, suggesting that the two proteins bind to each other.

Figure 8:
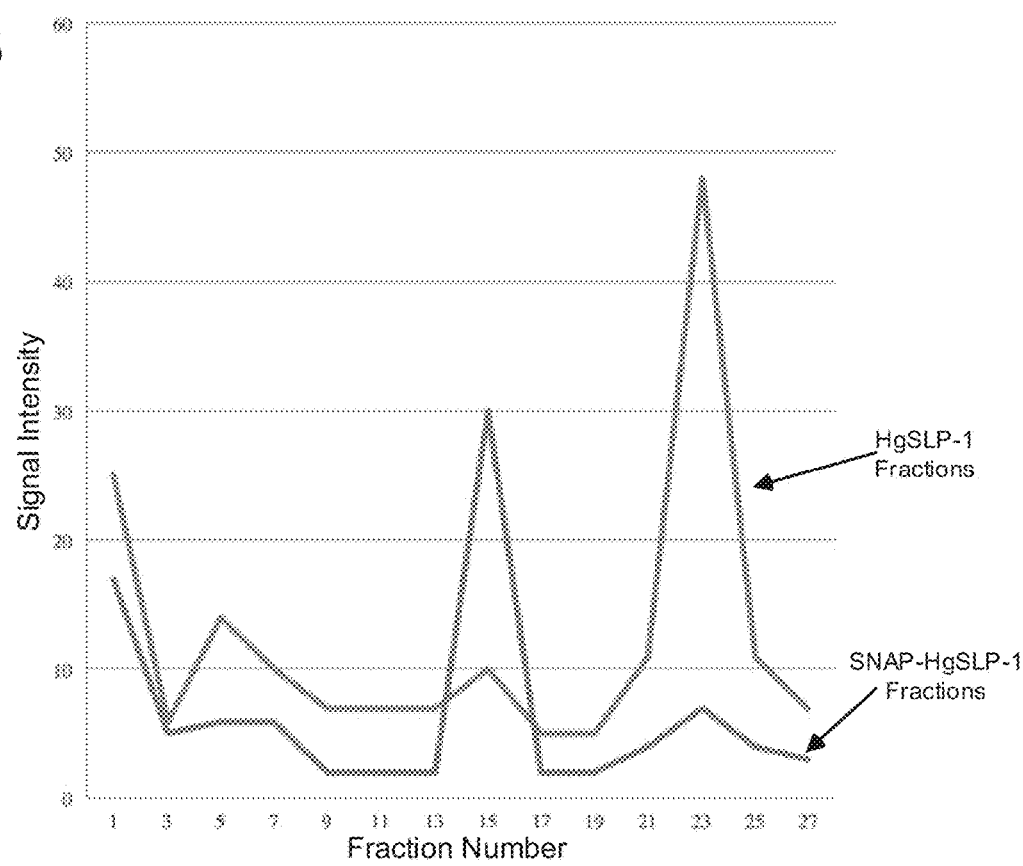
Figure 10:
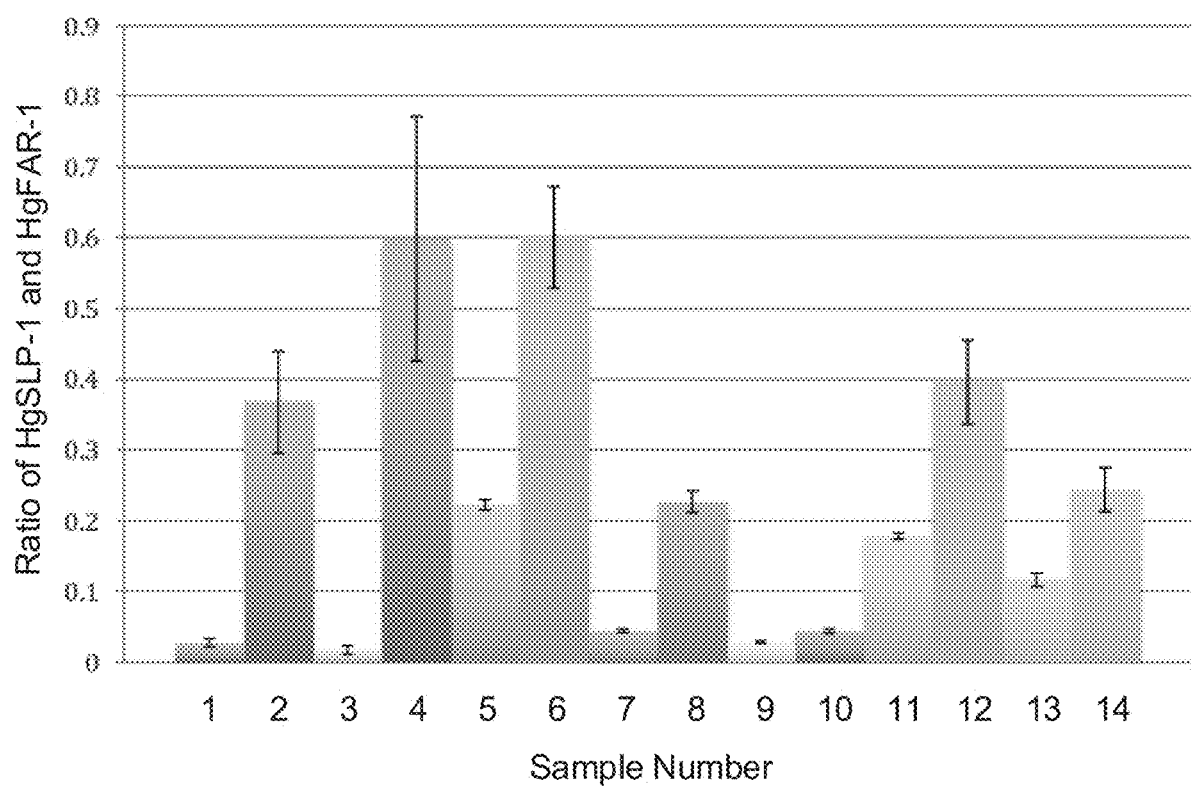

To gain additional evidence of protein-protein interaction, the total *E. coli* protein extracts described above containing HgSLP-1 or both HgSLP-1 and α-SNAP proteins were independently run over a gel filtration column. The fractions were collected and assayed for the presence of the HgSLP-1 protein via antibody dot blots. The HgSLP-1 (36.8 kDa) alone eluted at fraction 23 slightly sooner than the chymotrypsinogen A standard (25 kDa) which eluted at fraction 30, which is consistent with its expected size. However, when extracts containing both HgSLP-1 and α-SNAP were run through the column, the HgSLP-1 eluted at fraction 15, very close to the albumin standard (67 kDa) that eluted at fraction 12. The shift in elution of HgSLP-1 is consistent with this protein binding to α-SNAP and confirms the co-purification experiments described above. In both protein extracts, early fractions, particularly fraction 1, also contained HgSLP-1. Since fraction 1 contains proteins too large to be fractionated by the column matrix, it suggests a larger HgSLP-1: a-SNAP complex (dimer) may form (FIG. 8).

Discussion

The identification of the molecular mechanisms that plant parasitic nematodes use to evade or suppress host plant resistance is of great practical significance, since understanding this process could lead to broader and more durable resistant plants or to rapid diagnostic tests to predict the virulence profile of field nematode populations. A genetic approach to the identification of nematode virulence genes makes few assumptions about the underlying nature of the genes controlling the virulence phenotype. Past genetic studies on SCN virulence indicated one or two genes control the nematodes ability to reproduce on Rhg1 and Rhg4 resistant plants (Dong & Opperman, *Genetics* 146: 1311-1318, 19). This foundational study showed that SCN was a viable genetic system; however, it was also clear that SCN lacked a genetic infrastructure (a genome sequence and sequence polymorphisms) needed for map-based cloning of the genes controlling the virulence phenotype.

Part of the problem has been resolved with the development of the semi-quantitative GoldenGate SNP assays for SCN (Carlson et al., *Human Molecular Genetics* 15: 1931-1937, 2006) that can be used for genetic mapping and for map-based cloning via allelic imbalance (Wong et al., *Nucleic Acids Res* 32: e69, 2004) or bulk segregant analysis (Hyten et al., *Crop Science* 49: 265-271, 2009). In our study, three SNPs (212, 1035 and 1533) showed a consistent difference in SNP frequency when the bulk nematodes were grown on resistant and susceptible plants. Our criteria for identifying candidate virulence genes in the scaffolds of interest was based on the hypothesis that an SCN virulence gene might encode an effector protein or may have entered the genome via HGT from a microorganism and that the putative virulence gene should have a clear sequence polymorphism(s) between virulent and avirulent parents. Due to a lack of known SCN effector proteins in the SCN scaffolds under investigation, the putative HGT events in two of the scaffolds became the focus of our attention. The scaffold with SNP 1035 contained HgBioB, the scaffold with SNP 212 contained the HgSLP-1, and the third SNP-containing region is still under analysis.

HgBioB

Biotin functions as a carboxyl carrier for biotin dependent carboxylases, which are critical for fatty acid metabolism and amino acid catabolism. Biotin has also been shown to play a role in cell signaling, epigenetic regulation of genes, chromatin structure (Zempleni et al., *Biotin*. BioFactors 35: 36-46, 2009; Zempleni et al., *The Journal of Nutrition* 139: 2389-2392, 2009), and recently in microbial pathogenesis, making it a good candidate for a SCN virulence gene (Feng et al., *Molecular Microbiology* 91: 300-314, 2014).

In general, multicellular animals, including SCN, have lost the ability to synthesize biotin de novo. It is assumed the gene loss occurred because animals can simply acquire the vitamins through their diet. Thus, it seems unusual that SCN, an animal and a parasite, would express biotin synthase. The discovery of HgBioB in one of the scaffolds associated with SCN virulence was very significant, since this gene had previously been identified and speculated to be involved in SCN virulence (Craig et al., *J Nematol* 41: 281-290, 2009). In fact, the SCN SNP 1035 associated with SCN virulence was in the HgBioB gene, making it the best candidate virulence gene in the scaffold. HgBioB has been predicted to be functional, since it retains a conserved active site, but the virulent and avirulent SCN appear to have slightly different amino acid sequences. These amino acid sequence differences could alter biotin synthase enzymatic activity and thus could be the basis of this virulence trait. The exact role HgBioB could play in virulence is unclear, but we have previously speculated it could be a method for the nematode to circumvent SCN resistance, if part of the mechanism of resistance is caused by the plant reducing biotin availability during a nematode resistance response. It should be noted, that the nematode does not have the complete biotin biosynthetic pathway, but only the last enzyme in the pathway. So, if a plant reduced biotin synthesis at the last step, as a mechanism to starve the nematode parasite, the precursors to biotin may still be available for conversion to biotin via HgBioB (Craig et al., *Mol Biol Evol* 25: 2085-2098, 2008; Craig et al., *J Nematol* 41: 281-290, 2009). In this scenario a more enzymatically active biotin synthase enzyme, in the virulent SCN, could give the nematode a competitive advantage. It would be necessary to measure the levels of biotin in SCN feeding cells of susceptible and resistant soybean plants to test this hypothesis.

HgSLP-1

The region of the SCN genome that contains SNP 212 encodes HgSLP-1, a gene that appears to have entered the SCN genome via HGT. This gene is ~6,000 bp from SNP 212 and thus might be expected to provide a strong selection on the SNP in the allelic imbalance experiments. The SCN gene encoding HgSLP-1 is homologous to a bacterial protein from *P. dendritiformis* that has no known function, but was predicted to contain a viral hemagglutinin stalk and Sec3_C domains. The area of homology between the two proteins is in the viral hemagglutinin stalk domain which is structurally related to the SNARE motif found in HgSLP-1 in that they both, form coiled-coil domains and are involved in protein-protein interactions that occur during membrane fusion events in the cell (Skehel & Wiley, *Cell* 95: 871-874, 199).

The presence of SNARE motifs in bacterial proteins is not unusual, in fact such proteins act as virulence effectors in intracellular human pathogens such as *Chlamydia*, *Mycobacterium*, *Salmonella* and *Legionella* (Wesolowski & Paumet, *Virulence* 1: 319-324, 2010). In these intracellular bacteria the SNARE domain acts as a mimic and suppresses host membrane fusion events which aids the bacteria by preventing the phagosome membranes from fusing with lysosomes and killing the bacteria. The bacterial SNARE-like proteins directly bind to host v-SNAREs to prevent membrane fusion (Delevoye et al., *PLoS Pathogens* 4: e1000022, 2008). This type of SNARE-like protein that suppresses membrane fusion could also play a similar role in SCN parasitism of susceptible soybean.

While little direct research has been conducted on this topic in plant-nematode interactions, transmission electron microscopy images of cyst nematode feeding cells consistently showed endoplasmic reticulum (ER) membrane association with nematode feeding tubes (Sobczak et al., *Nematology* 1: 363-374, 1999) and enlarged ER membranes in syncytia (Endo, "Cellular responses to infection." In: Riggs & Wrather, editors. Biology and management of the soybean cyst nematode. St. Paul, Minn.: American Phytopathological Society. pp. 37-49, 1992; Sobczak & Golinowski, "Cyst Nematodes and Syncytia." In: Jones et al., editors. Genomics and Molecular Genetics of Plant-Nematode Interactions. Dordrecht: Springer. pp. 61-82, 2011), suggesting alteration of plant membranes might be essential for nematode feeding. However, such images do not shed light on whether nematodes suppress membrane fusion during feeding cell formation. In addition, the formation of plant cell plate is mediated by SNARE proteins; therefore, it is not unreasonable to suggest that the formation of the syncytia via the breakdown of neighboring cell walls may also be impacted by HgSLP-1 if it were able to interact with SNARE proteins which control this process (Zhang et al., *PLoS ONE* 6: e26129, 2011). Transcriptome data from syncytia suggests that some alteration of host secretion machinery occurs since soybean α-SNAP is not abundantly expressed in susceptible plants (Matsye et al., *Plant Mol Biol* 80: 131-155, 2012; Matsye et al., *Plant Mol Biol* 77: 513-528, 2011).

The role of plant membrane fusion in SCN resistant plants is more firmly established since one of the Rhg1 resistance genes encodes a α-SNAP protein. These α-SNAP proteins may confer SCN resistance by themselves (Matsye et al., *Plant Mol Biol* 80: 131-155, 2012; Pant et al., *Plant Mol Biol.*, 85:101-121, 2014) or in combination with the other resistance genes at the Rhg1 locus (Cook et al., *Science* 338: 1206-1209, 2012). The Rhg-1 α-SNAP proteins show significant polymorphisms between and within SCN resistant and susceptible soybean lines (Cook et al., *Plant Physiol*, 2014). The α-SNAPs are part of the complex of proteins that regulate membrane fusion and are highly conserved among eukaryotic organisms (Ferro-Novick & Jahn. *Nature* 370: 191-193, 1994), but it has been suggested that the Rhg1 α-SNAPs are specialized for conferring SCN resistance (Cook et al., *Science* 338: 1206-1209, 2012; Cook et al., *Plant Physiol*, 2014). To initiate membrane fusion between a vesicle and a target membrane, a complex of proteins must interact; a vesicle will have a membrane bound v-SNARE (also referred to as R-SAREs, Vamp or synaptobrevin proteins), while the target membrane will have a different membrane bound t-SNARE protein (also referred to as Q-SAREs or syntaxin proteins) (Fasshauer et al., *Proc Natl Acad Sci USA* 95: 15781-15786, 1998). The complex also contains a protein called SNAP-25 that binds to the other SNAREs to form a stable trans-SNARE complex where coiled-coil domains bind these proteins together (Fasshauer et al., *Proc Natl Acad Sci USA* 95: 15781-15786, 1998; Chen & Scheller, *Nature Reviews MCB* 2: 98-106, 2001) (FIG. 9A). The soluble protein α-SNAP is an adapter protein and binds to the t-SNARE. NSF and to a lesser extent SNAP-25 (Hayashi et al., *The EMBO J* 14: 2317-2325, 1995) and stimulates the NSF ATPase to disassemble the cis-SNARE complex after membrane fusion (Vivona et al., *J Biol Chem* 288: 24984-24991, 2013). α-SNAP proteins bind to t-SNAREs via coiled-coil domains both in trans-SNARE complexes and independently (Barnard et al., *Molecular Biology of the Cell* 7: 693-701, 1996). When α-SNAP binds to free t-SNAREs in a cell, this interaction blocks the protein and prevents membrane fusion events (Rodriguez et al., *PLoS ONE* 6: e21925, 2011). Thus, it seemed possible that if the HgSLP-1 could act as a t-SNARE mimic and bind to an α-SNAP, or a soybean v-SNARE, it might prevent membrane fusion events in the nematodes' feeding cell by sequestering these required plant membrane fusion proteins (FIG. 99).

This model is supported by the observations that the HgSLP-1 protein is expressed and secreted from an esophageal gland cell while the nematode is parasitizing the plant and the observation that HgSLP-1. We should note that while our data does suggest HgSLP-1 is secreted from a subventral gland, due to its presence in the esophageal lumen and stylet, our immunolocalization data in not clear in showing the protein entering the feeding cells. While it is likely that HgSLP-1 enters the nematode feeding cell, future higher-resolution immunolocalization experiments will need to be conducted to resolve the in planta localization of HgSLP-1. The model is also supported by the data that indicates HgSLP-1 and soybean α-SNAP bind to each other when co-expressed and co-purified from *E. coli*. The consequence of such an interaction of HgSLP-1 and α-SNAP might be to suppress membrane fusion events and this might disrupt both plant defense pathways and numerous normal cellular activities.

Exactly how HgSLP-1 might mitigate host defenses in soybean lacking the Rhg-1 loci is unclear, but it has been demonstrated that over expression of α-SNAP can induce syntaxin 31 in soybean and that this t-SNARE protein enhances SCN resistance (Pant et al., *Plant Mol Biol.,* 85:101-121, 2014), thus blocking this interaction may promote susceptibility. It has also been demonstrated in tobacco (*Nicotiana tabacum*) that by blocking syntaxin SYP132, a t-SNARE protein that transports vesicles containing PR proteins, increased bacterial susceptibility results (Kalde et al., *Proc Natl Acad Sci USA* 104: 11850-11855, 2007). Similarly, resistance to *Peronospora parasitica* is mediated via VAMP721/722 vesicles in *Arabidopsis* (Kim et al., *The Plant J: CMB* 79: 835-847, 2014), suggesting vesicle transport is a critical component for host-plant resistance to several plant pathogens. Thus, it seems plausible that HgSLP-1 could block the vesicle-mediated transport of anti-nematode proteins or metabolites in a similar way and inactive this type of basic host defense mechanism. However in Rhg1-mediated resistance we have a different scenario where up to 10 copies of Rhg1 α-SNAP and associated resistance genes. In effect, the α-SNAP in the resistant plant could be specialized to bind the nematode SNARE mimic and block its effect (FIG. 9C). This idea that the Rhg1 α-SNAP is specialized for nematode resistance was suggested in the original paper describing the Rhg1 loci (Cook et al., *Science* 338: 1206-1209, 2012).

However, our data suggests the role of HgSLP-1 and its related family members in nematode virulence or pathogenicity is not simple. Different isolates of SCN populations had variable copies of the HgSLP-1 gene and the RNA-seq data suggests that the mRNA encoded by the gene is alternatively spliced and forms containing intron sequences may be produced. This diversity of SCN SNARE like proteins could reflect the nematodes attempt to adapt to different soybean cultivars with different complements of α-SNAP proteins or other binding partners of HgSLP-1. Indeed, the apparent reduction in copy number of HgSLP-1 from TN20 and other nematode strains may reflect a resistance evasion mechanism used by the nematode as several highly virulent SCN strains appear to have reduced numbers of the gene in the population of nematodes. If HgSLP-1 is important for establishing a feeding cell, one might expect that the lack of this protein may impair the growth and development of virulent SCN lacking the gene. However, we suggest that virulent nematodes may express different forms of SCN SNARE-like protein (such as the ESTs CB825264 and CA940412) that are not recognized by the Rhg1 α-SNAPs, due to mutations in the SNARE domain, and thus may compensate for the loss of HgSLP-1 expression (FIG. 9D). While the lack of HgSLP-1 may play a role in evading host plant defense mechanisms, other potential virulence genes, such as the HgBioB or the gene near SNP 1533 are probably also required for the virulence phenotype.

Some of the SCN strains we tested for HgSLP-1 were the genetically characterized inbred SCN strains OP20, OP25 and OP50 (Dong & Opperman, *Genetics* 146: 1311-1318, 1997). The genetic study of the OP SCN inbred strains established that SCN virulence was controlled by one or two genes, depending on the type of resistant plants and nematode strains were tested. This landmark study established that virulence on Rhg1-type resistance was genetically controlled by the dominant Ror1 gene (reproduction on resistant) in the virulent strain OP50, but OP50 growth on Rhg4/Rhg1-based resistance was controlled by the recessive ror2 gene. The virulent inbred SCN strain OP20 was shown to require two virulence genes to reproduce on the Rhg1 source of resistance. Dong & Opperman (1997) suggested that SCN utilizes several mechanisms to overcome Rhg1-based resistance, but only one gene, ror2, to overcome Rhg1/Rhg4-type resistance. The avirulent SCN strain OP25 was unable to reproduce on any source of resistance. When these nematodes were tested for the presence or absence of the HgSLP-1, the gene was present in OP25 (avirulent SCN), but nearly absent or reduced in copy number in OP20 and OP50 (both virulent on both Rhg1 and Rhg1/Rhg4-type resistance). It is interesting to note, that even though OP20, OP50 and TN20 are not related to each other (two are from North Carolina and the other from Missouri) the nematode strains have a similar virulence profile in that they grow on most SCN resistant plants. More work is needed to confirm the correlation between lower copy number of HgSLP-1 and broad SCN virulence. However, it is interesting that the ror2 virulence gene that controls growth on the Rhg1/Rhg4-type resistance is a recessive gene. The deleted HgSLP-1 gene in most of the nematodes in this strain would be expected to act as a recessive gene, thus it may be that ror2 is in fact this deletion or lack of HgSLP-1 or that the deletion of SCN virulence genes to evade host plant resistance is a common mechanism.

Overall, HgSLP-1 could play a role in SCN virulence, via its absence, but it could be involved with feeding cell formation if alterations of membrane fusion would be beneficial in this process. It seems plausible that HgSLP-1 may have other binding partners in the plant cell in addition to the Rhg1 α-SNAP. It will be interesting in the future to test other α-SNAP variants to determine their binding kinetics to HgSLP-1 in its various forms. It will also be important to follow up on the involvement in biotin in Rhg1 mediated resistance by further analysis of the biotin biosynthetic enzymes in the plant and nematode. The virulence gene identification approach described in this paper should be adaptable to other plant-nematode systems to associate SNPs with nematode phenotypes of interest. In addition, new high throughput methods of DNA sequencing and genotyping will lower the cost and increase the resolution of this type of genetic screening approach making it applicable to any sexually reproducing nematode species. Increasing our knowledge of how nematodes evade/suppress host plant resistance may lead to more durable SCN resistant plants or to improved methods of monitoring virulent nematode populations, which in turn will aid in the management of these damaging pathogens.

Example 2

Quantification of HgSLP-1 Copy Number to Assess Virulence in a Nematode Population This Example describes a study of nematode virulence, employing quantification of HgSLP-1 copy number as a measure of virulence in a field population.

Field populations of SCN taken from 14 different samples were grown in the lab on susceptible soybean Essex. The nematodes were allowed to increase for about 6 weeks, then the cysts were extracted and popped to release the eggs. Some of the eggs were used to inoculate susceptible (Essex)

and resistant (PI88788) soybean (equal numbers of eggs were used in the inoculations).

The rest of the eggs were used to extract DNA. The eggs were added to 2 ml plastic tubes, excess water removed, and then two 3.2 mm diameter stainless steel beads were added. The prepared sample tubes were frozen in liquid nitrogen and then shaken at high velocity on a mini-beadbeater-16 model 607 (Biospec Products) cell disrupter. The frozen pulverized eggs were transferred back to liquid nitrogen for storage until the DNA was extracted using a DNAeasy Blood and Tissue kit (Qiagen) following manufacturer's instructions. The copy number assay for HgSLP-1 was performed as described above.

In this analysis, we found that some of the nematodes did not grow (this could be since they picked up a disease from the field, a common problem), thus not all the data points have a growth test. The ones that did, appeared to support the theory that low copy numbers of HgSLP-1 allow the nematode to grow on resistant plant PI88788.

Results are shown in FIG. 10. The QPCR assay measures the frequency of HgSLP-1 (copy number varies) in each nematode population relative to HgFAR-1 (copy number does not vary). The smaller/shorter the bars in FIG. 1 are SCN populations predicted to be the more virulent. Samples 1, 7, 9, 10 SCN were able to grow on susceptible and resistant soybean plants (PI88788) and have relatively low copies of HgSLP-1. Sample 5 SCN were also able to grow on PI88788 SCN, but had intermediate HgSLP-1 copy number. However, Sample 6 SCN, which has a relatively higher copy number of HgSLP-1, did not grow on PI88788, but did grow on a susceptible soybean plant. The other sample SCN populations did not grow on either susceptible or resistant soybean, thus their virulence level is unknown.

Example 3

Detection/Quantification of SCN Virulence in Soil

This Example provides an exemplary system for detecting the resistance-breaking tendency (virulence) of nematodes (e.g., SCN) in a field/soil area.

Nematodes (e.g., cysts or eggs) are isolated from a soil sample taken, for instance, from a field in which soybean is or may in the future be planted. By way of example, the soil sample may be an aggregated sample, taken from multiple sub-locations within a target area that are then mixed to obtain a sample more representative of a possibly heterogeneous distribution over the source location area. Nematode, egg, and cyst isolation techniques are well known to those of skill in the art. DNA is then obtained from the isolated nematode population(s), for instance using art-recognized techniques. Representative techniques are provided herein.

In one embodiment the copy number of the HgSLP-1 gene is determined. Usually, the copy number is determined relative to a gene of stable/largely non-variant copy number, and the copy number ratio is used as in Example 1 and 2 above. The lower the copy number of HgSLP-1 in the tested nematode population, the more likely the population is to be virulent (that is, capable of growth on otherwise resistant soybean plants).

In another embodiment, the sequence of the BioB gene is determined in the population of nematodes, specifically to determine the sequence at positions 70 and/or 132 (numbering as in SEQ ID NO: 44). BioB sequence containing a C at position 70, and/or a G at position 132, is expected to be from a non-virulent nematode; while BioB sequence containing a G at position 70, and/or an A at position 132, is expected to be from a virulent nematode. In a mixed population, the relative amount of each sequence can be calculated to determine a relative level of virulence in the population.

The results of such a virulence analysis can be used, for instance, in decisions regarding how to utilize or treat the field from which the soil sample(s) were obtained. By way of example, in heavily virulent fields (that is, fields with a relatively high level of virulent nematodes), the field might be aggressively treated to eradicate the SCN. Alternatively, such a field might be turned, for instance for a number of seasons or years, to a use other than growing soybean—that is, rotated to a different use—or rotated to a soybean cultivar having a different source of resistance than that found in PI88788 (e.g., distinct from the α-SNAP-mediate resistance described herein) (see, e.g., Luedders & Dropkin, *Crop Sci.* 23, 263-264, 1983).

This disclosure provides systems for analyzing nematode (e.g., soybean cyst nematode) genetics and identifying resistance/virulence and other genes, and the identification of two putative nematode virulence genes. The disclosure further provides methods of using the presence, absence, and/or sequence of these genes to detect virulent nematode populations, for instance in soil. It will be apparent that the precise details of the methods described may be varied or modified without departing from the spirit of the described invention. We claim all such modifications and variations that fall within the scope and spirit of the claims below.

The invention claimed is:

1. A method, comprising:
 isolating soybean cyst nematodes (SCN) from at least one soil sample from a source location;
 obtaining DNA from the isolated nematodes;
 measuring the relative copy number of the *Heterodera glycines* SNARE-like protein-1 gene (HgSLP-1) gene comprising the nucleic acid sequence of SEQ ID NO: 40 or SEQ ID NO: 41 in the DNA obtained from the isolated nematodes;
 detecting a low relative copy number of HgSLP-1, wherein a low relative copy number of HgSLP-1 is indicative of SCN virulence in the soil sample; and
 planting in soil at the source location a soybean cultivar having a different source of resistance than that in resistant cultivar PI88788.

2. The method of claim 1, wherein measuring the relative copy number of the HgSLP-1 gene in the nematode DNA comprises measuring the abundance of the HgSLP-1 sequence compared to the copy number of a control nematode gene using quantitative PCR.

3. The method of claim 2, wherein the control nematode gene is *Heterodera glycines* fatty acid and retinol binding protein-1 gene (HgFAR-1).

4. The method of claim 2, further comprising preparing a ratio of the copy number of HgSLP-1 to the copy number of the control nematode gene, and wherein a ratio of ≤0.3 indicates SCN virulence in the soil.

5. The method of claim 2, wherein the quantitative PCR uses primer pair SEQ ID NOs: 18 and 19 or NOs: 46 and 47 to amplify HgSLP-1 DNA.

6. The method of claim 1, wherein measuring the copy number of the HgSLP-1 gene in the nematode DNA comprises detecting HgSLP-1 DNA using a labeled probe having the sequence of SEQ ID NO: 20 or 48.

7. The method of claim 3, wherein the quantitative PCR uses primer pair SEQ ID NOs: 15 and 16 to amplify HgFAR-1 DNA.

8. The method of claim 3, wherein measuring the copy number of the HgFAR-1 gene in the nematode DNA comprises detecting the HgFAR-1 DNA using a labeled probe having the sequence of SEQ ID NO: 17.

9. A method, comprising:
 isolating soybean cyst nematodes (SCN) from at least one soil sample from a source location;
 obtaining DNA from the isolated nematodes;
 detecting the sequence of the *Heterodera glycines* bacterial-like biosynthase gene (HgBioB) gene in the DNA obtained from the isolated nematodes;
 detecting presence of C at position 70 and A at position 132 (numbered with reference to SEQ ID NO: 44) within HgBioB, wherein the presence of C at position 70 and A at position 132 (numbered with reference to SEQ ID NO: 44) within HgBioB is indicative of SCN virulence in the soil sample; and
 planting in soil at the source location a soybean cultivar having a different source of resistance than that in resistant cultivar PI88788.

* * * * *